(12) United States Patent
Neitzel et al.

(10) Patent No.: US 8,193,389 B2
(45) Date of Patent: Jun. 5, 2012

(54) N-SUBSTITUTED BENZENE SULFONAMIDES

(75) Inventors: Martin Neitzel, Pacifica, CA (US); Jennifer Marugg, San Jose, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 771 days.

(21) Appl. No.: 11/078,990

(22) Filed: Mar. 11, 2005

(65) Prior Publication Data

US 2005/0245573 A1 Nov. 3, 2005

Related U.S. Application Data

(60) Provisional application No. 60/552,555, filed on Mar. 11, 2004.

(51) Int. Cl.
*C07C 303/00* (2006.01)
*A61K 31/16* (2006.01)
(52) U.S. Cl. .......................................... 564/90; 514/604
(58) Field of Classification Search ............... 548/372.5; 514/361, 604; 564/90
See application file for complete search history.

(56) References Cited

U.S. PATENT DOCUMENTS

| | | | | |
|---|---|---|---|---|
| 4,960,897 A | * | 10/1990 | Jikihara et al. | 546/346 |
| 4,971,620 A | * | 11/1990 | Jikihara et al. | 504/333 |
| 2007/0191341 A1 | * | 8/2007 | Neitzel et al. | 514/212.02 |

FOREIGN PATENT DOCUMENTS

| | | | |
|---|---|---|---|
| CA | 2486581 | * | 6/2003 |
| CH | 246983 | | 2/1947 |
| EP | 0 326 170 | | 8/1989 |
| JP | 2002-537376 | | 8/2000 |
| WO | 9803166 | * | 1/1998 |
| WO | 01-77074 | | 10/2001 |
| WO | 02-089749 | | 11/2002 |
| WO | 03/007888 | | 1/2003 |
| WO | WO03/053912 | | 7/2003 |
| WO | WO03/103660 | | 12/2003 |
| WO | 2004-019935 | | 3/2004 |

OTHER PUBLICATIONS

Hcaplus 112:177937, "Hydrogen bonding. Part 9. Solute proton-donor and proton-acceptor scales for use in drug design", Abraham et. al., (1989).*
Hcaplus 1986:129579, "A new preparation of enamides and dienamides", Berthon et. al., 1985.*
Patani et. al., "Bioisosterism: A Rational Approach in Drug Design", Chem. Rev. 1996, 96, 3147-3176.*
Caplus 2003:363128,"Bromoallenes as Synthetic Equivalents of Allyl Dications: Synthesis of Medium-Sized Nitrogen Heterocycles through the Cyclization of Bromoallenes in the Presence of a Palladium (0) Catalyst and an Alcohol", Angew. Chem. Int. Ed. 2003.*
Ohno et. al., "Bromoallenes as Synthetic Equivalents of Allyl Dications: Synthesis of Medium-Sized Nitrogen Heterocycles through the Cyclization of Bromoallenes in the Presence of a Palladium (0) Catalyst and an Alcohol", Angew. Chem. Int. Ed. 2003, 42, pp. 1749-1753.*
Caplus 2003:363128,"Bromoallenes as Synthetic Equivalents of Allyl Dications: Synthesis of Medium-Sized Nitrogen Heterocycles through the Cyclization of Bromoallenes in the Presence of a Palladium (0) Catalyst and an Alcohol", Angew. Chem. Int. Ed. 2003, Ohno et. al.*
Parsons et. al., "Radical Cyclisation of Amino Aldehydes Leading to Hydroxy Pyrrolidines and Piperidines", Tetrahedron Letters, vol. 38, No. 33, pp. 5907-5910.*
HCAPLUS 1989:114687.*
Bottini, A. et al., J. Am. Chem. Soc. 1962, 84, 195-99.*
HCAPLUS 1989:75066.*
Bottini, A. et al., J. Org. Chem., 1962, 27, 3688-90.*
Silverman, R. "The Organic Chemistry of Drug Design and Drug Action," 2004, Elsevier, pp. 29-32.*
Ohno et al., Angew. Chem. Int. Ed. 2003, vol. 42, pp. 1749-1753.*
Caplus 2003:363128 Angew. Chem. Int. Ed. 2003.*
Parsons et al., Tetrahedron Lett. vol. 38, pp. 5907-5910, 1997.*
PCT International Search Report PCT/US2005/007811, dated Sep. 26, 2005.
Database Beilstein, Beilstein Institut zur Forderung der Chemischen Wissenschaften, Frankfurt am Main, DE, Database Accession No. BRN 2149884, XP-002343799 Abstract.
Database Beilstein, Beilstein Institut zur Forderung der Chemischen Wissenschaften, Frankfurt am Main, DE, Database Accession No. BRN 6432097, XP-002343800 Abstract.
Database Beilstein, Beilstein Institut zur Forderung der Chemischen Wissenschaften, Frankfurt am Main, DE, Database Accession No. BRN 2128431, XP-002343801 Abstract.
Database Beilstein, Beilstein Institut zur Forderung der Chemischen Wissenschaften, Frankfurt am Main, DE, Database Accession No. BRN 2136785, XP-002343802 Abstract.

(Continued)

*Primary Examiner* — Janet Andres
*Assistant Examiner* — Heidi Reese

(57) ABSTRACT

The invention provides N-substituted benzenesulfonamides for use in treating or preventing cognitive disorders, such as Alzheimer's Disease.

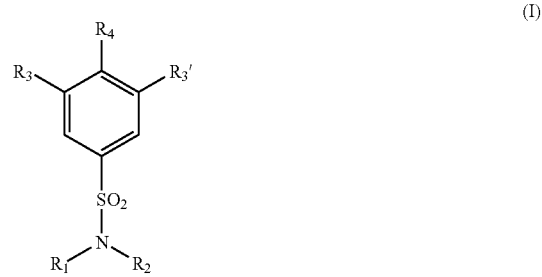

(I)

Compounds of particular interest are defined by Formula (I), wherein $R_1$, $R_2$, $R_3$, $R_4$, and $R_{3'}$ are as described in the specification. The invention also encompasses pharmaceutical compositions comprising compounds of Formula (I) as well as methods of treating cognitive disorders, including Alzheimer's disease using compounds of Formula (I).

24 Claims, No Drawings

OTHER PUBLICATIONS

Database Beilstein, Beilstein Institut zur Forderung der Chemischen Wissenschaften, Frankfurt am Main, DE, Database Accession No. BRN 2852299, XP-002343803 Abstract.
STN Search.
Journal of the American Chemical Society (2002), vol. 124(46), pp. 13856-13863.
Journal of Organic Chemistry, (1978), vol. 43(7), pp. 1337-1342.
Chemical Abstract 110:212388.
Chemical Abstract 134:289960.
Chemical Abstract 128:180310.
Chemical Abstract 119:160021.
Henry et al., "Mitsunobu reactions of N-alkyl and n-acyl sulfonamides—an efficient route to protected amines" Database Chemical Abstracts Services XP002643987.
Cope, et al., "N-methyl -N-phenylalkylaminoalkyl benzoates and p-aminobenzoates," Chemical Abstracts Services XP002643988.
Yoneda et al., "Process for preparing optically active (R)-1-(benzofuran-2-yl)-2-propylaminopentane", Chemical Abstracts Services XP002643545.

* cited by examiner

N-SUBSTITUTED BENZENE SULFONAMIDES

CROSS REFERENCE TO RELATED APPLICATIONS

This application claims priority from U.S. Provisional Application Ser. No. 60/552,555, filed Mar. 11, 2004, which is incorporated herein by reference in its entirety.

BACKGROUND OF THE INVENTION

1. Field of the Invention

The invention relates to N-substituted benzene sulfonamides. More specifically, it relates to such compounds that inhibit β-amyloid peptide release and/or its synthesis and, therefore, are useful in the prevention of cognitive disorders in patients susceptible to cognitive disorders and/or in the treatment of patients with cognitive disorders in order to inhibit further deterioration in their condition.

2. State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39-43 amino acids designated the β-amyloid peptide (βAP) or sometimes Aβ, AβP or β/A4. β-Amyloid peptide was first purified and a partial amino acid sequence was provided by Glenner et al., Biochem. Biophys. Res. Commun., 120:885-890 (1984) The isolation procedure and the sequence data for the first 28 amino acids are described in U.S. Pat. No. 4,666,829.

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). Sequential processing of the precursor protein by the enzymes referred to generically as beta- and gamma-secretases, give rise to the β-amyloid peptide fragment. Both enzymes have now been molecularly cloned, and characterized to differing levels.

Several lines of evidence indicate that progressive cerebral deposition of β-amyloid peptide plays a seminal role in the pathogenesis of AD and can precede cognitive symptoms by years or decades. See, for example, Selkoe, Neuron, 6:487-498 (1991). The most important line of evidence is the discovery that missense DNA mutations at amino acid 717 of the 770-amino acid isoform of APP can be found in affected members but not unaffected members of several families with a genetically determined (familial) form of AD (Goate et al., Nature, 349:704-706 (1990); Chartier Harlan et al., Nature, 353:844-846 (1989); and Murrell et al., Science, 254:97-99 (1991.) Another such mutation, known as the Swedish variant, is comprised of a double mutation changing lysine$^{595}$-methionine$^{596}$ to asparagine$^{595}$-leucine$^{596}$ (with reference to the 695 isoform was found in a Swedish family) was reported in 1992 (Mullan et al., Nature Genet., 1:345-347 (1992). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP metabolism, and subsequent deposition of its β-amyloid peptide fragment, can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

One approach toward inhibiting amyloid peptide synthesis in vivo is by inhibiting gamma secretase, the enzyme responsible for the carboxy-terminal cleavage resulting in production of β-amyloid peptide fragments of 40 or 42 residues in length. The immediate substrates for gamma secretase are β-cleaved, as well as α-cleaved carboxy-terminal fragments (CTF) of APP. The gamma-secretase cleavage site on β- and (α-CTF fragments occurs in the predicted transmembrane domain of APP. Inhibitors of gamma-secretase have been demonstrated to effect amyloid pathology in transgenic mouse models (Dovey, H. F., V. John, J. P. Anderson, L. Z. Chen, P. de Saint Andrieu, L. Y. Fang, S. B. Freedman, B. Folmer, E. Goldbach, E. J. Holsztynska et al. (2001). "Functional gamma-secretase inhibitors reduce beta-amyloid peptide levels in brain." J Neurochem 76(1): 173-81.)

Gamma secretase is recognized to be a multi-subunit complex comprised of the presenilins (PS1 or PS2), Nicastrin, Aph-1, and Pen 2 (De Strooper, B. (2003). "Aph-1, Pen-2, and Nicastrin with Presenilin generate an active gamma-Secretase complex." Neuron 38(1): 9-12; Edbauer, D., E. Winkler, J. T. Regula, B. Pesold, H. Steiner and C. Haass (2003). "Reconstitution of gamma-secretase activity." Nat Cell Biol 5(5): 486-8; Kimberly, W. T., M. J. LaVoie, B. L. Ostaszewski, W. Ye, M. S. Wolfe and D. J. Selkoe (2003). "Gamma-secretase is a membrane protein complex comprised of presenilin, nicastrin, Aph-1, and Pen-2." Proc Natl Acad Sci USA 100(11): 6382-7). Much evidence indicates that PS comprises the catalytic moiety of the complex, while the other identified subunits are necessary for proper maturation and sub-cellular localization of the active enzyme complex (reviewed in De Strooper, B. (2003). "Aph-1, Pen-2, and Nicastrin with Presenilin generate an active gamma-Secretase complex." Neuron 38(1): 9-12.) Consistent with this hypothesis: PS knock-out mice exhibit significant reductions in β-amyloid production (De Strooper, B., P. Saftig, K. Craessaerts, H. Vanderstichele, G. Guhde, W. Annaert, K. Von Figura and F. Van Leuven (1998). "Deficiency of presenilin-1 inhibits the normal cleavage of amyloid precursor protein." Nature 391(6665): 387-90; Haass, C. and D. J. Selkoe (1998). "Alzheimer's disease. A technical KO of amyloid-beta peptide." Nature 391(6665): 339-40; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2(7): 461-2); point mutations of putative active site aspartate residues in PS trans-membrane domains inhibit β-amyloid production in cells in a dominant negative fashion (Wolfe, M. S., W. Xia, B. L. Ostaszewski, T. S. Diehl, W. T. Kimberly and D. J. Selkoe (1999). "Two transmembrane aspartates in presenilin-1 required for presenilin endoproteolysis and gamma-secretase activity." Nature 398(6727): 513-7; Kimberly, W. T., W. Xia, T. Rahmati, M. S. Wolfe and D. J. Selkoe (2000). "The transmembrane aspartates in presenilin 1 and 2 are obligatory for gamma-secretase activity and amyloid beta-protein generation." J Biol Chem 275(5): 3173-8); active site directed substrate-based transition state isosteres designed to inhibit gamma secretase directly conjugate to PS (Esler, W. P., W. T. Kimberly, B. L. Ostaszewski, T. S. Diehl, C. L. Moore, J. Y. Tsai, T. Rahmati, W. Xia, D. J. Selkoe and M. S. Wolfe (2000). "Transition-state analogue inhibitors of gamma-secretase bind directly to presenilin-1." Nat Cell Biol 2(7): 428-34; Li, Y. M., M. Xu, M. T. Lai, Q. Huang, J. L. Castro, J. DiMuzio-Mower, T. Harrison, C. Lellis, A. Nadin, J. G. Neduvelil et al. (2000). "Photoactivated gamma-secretase inhibitors directed to the active site covalently label presenilin 1." Nature 405(6787): 689-94); finally, allosteric gamma secretase inhibitors have likewise been demonstrated to bind directly to PS (Seiffert, D., J. D. Bradley, C. M. Rominger, D. H. Rominger, F. Yang, J. E. Meredith, Jr., Q. Wang, A. H. Roach, L. A. Thompson, S. M. Spitz et al. (2000). "Presenilin-1 and -2 are molecular targets for gamma-secretase inhibitors." J Biol Chem 275(44): 34086-91.)

Current evidence indicates that in addition to APP processing leading to β-amyloid synthesis, gamma-secretase also mediates the intra-membrane cleavage of other type I transmembrane proteins (reviewed in Fortini, M. E. (2002). "Gamma-secretase-mediated proteolysis in cell-surface-receptor signaling." Nat Rev Mol Cell Biol 3(9): 673-84, see also Struhl, G. and A. Adachi (2000). "Requirements for presenilin-dependent cleavage of notch and other transmembrane proteins." Mol Cell 6(3): 625-36.) Noteworthy among the known substrates of gamma-secretase is mammalian Notch 1. The Notch 1 protein is important for cell fate determination during development, and tissue homeostasis in the adult. Upon ligand engagement via the Notch ecto-domain, Notch undergoes sequential extra-cellular and intra-membrane processing analogous to APP. The intra-membrane processing of Notch mediated by gamma secretase leads to release of the Notch intracellular domain (NICD). The NICD fragment mediates Notch signaling via translocation to the nucleus, where it regulates expression of genes mediating cellular differentiation in many tissues during development, as well as in the adult.

Disruption of Notch signaling via genetic knock-out (KO) results in embryonic lethal phenotype in mice (Swiatek, P. J., C. E. Lindsell, F. F. del Amo, G. Weinmaster and T. Gridley (1994). "Notch1 is essential for postimplantation development in mice." Genes Dev 8(6): 707-19; Conlon, R. A., A. G. Reaume and J. Rossant (1995). "Notch1 is required for the coordinate segmentation of somites." Development 121(5): 1533-45.) The Notch KO phenotype is very similar to the phenotype observed PS1 KO mice, and precisely reproduced by PS1/PS2 double KO mice (De Strooper et al. (1998). "Deficiency of presenilin-1 inhibits the normal cleavage of amyloid precursor protein." Nature 391(6665): 387-90; Donoviel, D. B., A. K. Hadjantonakis, M. Ikeda, H. Zheng, P. S. Hyslop and A. Bernstein (1999). "Mice lacking both presenilin genes exhibit early embryonic patterning defects." Genes Dev 13(21): 2801-10; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2(7): 461-2.) This convergence of phenotypes observed in knock-out mice of either the substrate (Notch) or the enzyme (PS) suggests that inhibitors of gamma secretase that also inhibit Notch function may be limited as therapeutic agents owing to the importance of Notch function in adult tissues (Fortini, M. E. (2002). "Gamma-secretase-mediated proteolysis in cell-surface-receptor signaling." Nat Rev Mol Cell Biol 3(9): 673-84.) As APP knock-out mice develop normally and without an overt phenotype Zheng, H., M. Jiang, M. E. Trumbauer, R. Hopkins, D. J. Sirinathsinghji, K. A. Stevens, M. W. Conner, H. H. Slunt, S. S. Sisodia, H. Y. Chen et al. (1996). "Mice deficient for the amyloid precursor protein gene." Ann NY Acad Sci 777: 421-6; Zheng, H., M. Jiang, M. E. Trumbauer, D. J. Sirinathsinghji, R. Hopkins, D. W. Smith, R. P. Heavens, G. R. Dawson, S. Boyce, M. W. Conner et al. (1995). "beta-Amyloid precursor protein-deficient mice show reactive gliosis and decreased locomotor activity." Cell 81(4): 525-31, the cumulative evidence, therefore, suggests that preferred gamma secretase inhibitors would have selectivity for inhibiting gamma secretase processing of APP over gamma secretase processing of Notch.

SUMMARY OF THE INVENTION

In a broad aspect, the invention provides compounds of Formula I:

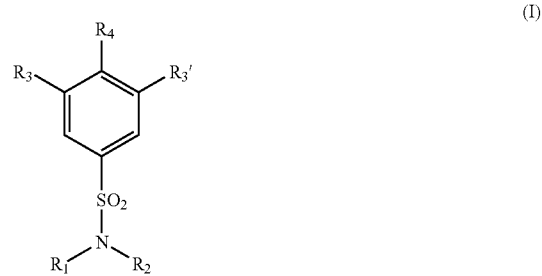

and pharmaceutically acceptable salts thereof, wherein
$R_1$ is $C_2$-$C_6$ alkynyl, $C_2$-$C_6$ alkenyl, or $C_1$-$C_8$ alkyl wherein each is optionally substituted with 1, 2, or 3 groups that are independently $C_1$-$C_6$ alkoxy, OH, halogen, CN, $C_1$-$C_6$ thioalkoxy, phenyl, naphthyl, $C_3$-$C_8$ cycloalkyl, $NH_2$, $NH(C_1-C_6)$alkyl, $N(C_1-C_6)$alkyl$(C_1-C_6$ alkyl), —C(O)$NH_2$, —C(O)$NH(C_1-C_6)$alkyl, —C(O)$N(C_1-C_6)$alkyl$(C_1-C_6)$alkyl, —C(O)phenyl, or $C_1-C_6$ alkoxycarbonyl, wherein each of the cyclic groups is optionally substituted with 1, 2, 3, or 4 groups that are independently halogen, $C_1-C_4$ alkyl, $C_1-C_4$ alkoxy, $NH_2$, $NH(C_1-C_6)$alkyl, $N(C_1-C_6)$alkyl$(C_1-C_6$ alkyl), —$SO_2$—$(C_1-C_6)$ alkyl, or OH; or $R_1$ is $C_3-C_8$ cycloalkyl optionally substituted with 1 or 2 groups that are independently $C_1-C_4$ alkyl, $C_1-C_4$ hydroxyalkyl, or OH; or $R_1$ is heterocycloalkyl or heterocycloalkyl$(C_1-C_4)$alkyl wherein the heterocycloalkyl group is piperidinyl, pyrrolidinyl, tetrahydrofuranyl, pyrazolyl, or morpholinyl, wherein the heterocycloalkyl groups are optionally substituted with 1 or 2 groups that are independently $C_1-C_4$ alkyl, $C_1-C_4$ alkoxy, phenyl, phenyl$(C_1-C_4)$alkyl, OH, halogen, $CO_2H$, $C_1-C_4$ alkoxycarbonyl, —C(O)$NH_2$, —C(O)$NH(C_1-C_4)$ alkyl, —C(O)$N(C_1-C_4)$alkyl$(C_1-C_4)$ alkyl, or $C_1-C_4$ alkoxycarbonyl; or $R_1$ is heteroaryl$(C_1-C_4)$alkyl, wherein the heteroaryl group is pyridyl, pyrimidyl, furanyl, or thienyl and the heteroaryl group is optionally substituted with 1, 2, or 3 groups that are independently halogen, $CO_2H$, $C_1-C_4$ alkoxycarbonyl, —C(O)$NH_2$, —C(O)$NH(C_1-C_4)$ alkyl, —C(O)$N(C_1-C_4)$alkyl$(C_1-C_4)$ alkyl, $C_1-C_4$ alkyl, $C_1-C_4$ alkoxy or OH;

$R_2$ is $C_1-C_8$ alkyl, $C_1-C_6$ hydroxyalkyl, or $C_2-C_8$ alkenyl, each of which is optionally substituted with 1, 2, or 3 groups that are independently phenyl, 2H-chromenyl, 1,2,3,4-tetrahydronaphthalenyl, indolyl, 3,4-dihydronaphthalenyl, phenyl, naphthyl, $C_3-C_8$ cycloalkyl, benzofuranyl, indolyl, 1,4-benzodioxanyl, 1,3-benzodioxolyl, pyridyl, pyrimidyl, $C_1-C_4$ alkyl, halogen, pyrazolyl, imidazolyl, oxazolyl, isoxazolyl, oxadiazolyl, thiazolyl, $NO_2$, thiadiazolyl, furanyl, triazolyl, or CN, wherein the cyclic portions of each of the above are optionally substituted with 1, 2, or 3 groups that are independently halogen, $CO_2H$, $C_1-C_6$ alkoxycarbonyl, —C(O)$NH_2$, —C(O)$NH(C_1-C_6)$ alkyl, —C(O)$N(C_1-C_6)$ alkyl $(C_1-C_6)$ alkyl, $C_1-C_4$ alkoxy optionally substituted with pyridyl, thiazolyl, or methyl thiazol-5-yl, $NO_2$, $C_1-C_4$ alkyl, —S(O)$_x$—$R_{25}$, —$(C_1-C_4$ alkyl)-S(O)$_x$—$R_{25}$, or OH; wherein
    x is 0, 1, or 2;
    $R_{25}$ is $C_1-C_6$ alkyl, OH, $NR_{26}R_{27}$;
    $R_{26}$ and $R_{27}$ are independently H, $C_1-C_6$ alkyl, phenyl $(C_1-C_4$ alkyl), phenyl, or pyridyl; or
    $R_{26}$, $R_{27}$ and the nitrogen to which they are attached represent pyrrolidinyl, piperidinyl, piperazinyl, morpholinyl, or imidazolidinyl;

$R_3$ is H, halogen, $C_1-C_6$ alkyl, $C_1-C_6$ alkoxy, $C_1-C_6$ haloalkyl, or CN, $R_4$ is H, halogen, $C_1-C_6$ alkyl optionally substituted with —$CO_2$—$(C_1-C_6$ alkyl), $C_1-C_6$ alkoxy, $C_1-C_6$ haloalkyl, $C_1-C_6$ haloalkoxy, CN, aryloxy, isocyanato, —$SO_2$—$(C_1-C_6$ alkyl), —NHR', —NR'R", $C_1-C_6$ alkanoyl, pyridyl, or phenyl; or $R_3$ and $R_4$ and the carbons to which they are attached form a heterocycloalkyl ring which is optionally substituted with 1, 2, or 3 groups that are independently $C_1-C_4$ alkyl, $C_1-C_4$ alkoxy, halogen, or $C_1-C_4$ alkanoyl wherein the alkanoyl group is optionally substituted with up to 3 halogen atoms;

$R_{3'}$ is H, —$SO_2$—NR'R", halogen, or $R_4$ and $R_{3'}$ and the carbons to which they are attached form a phenyl ring; or $R_4$ and $R_{3'}$ and the carbons to which they are attached form a 1-oxa-2,3-diazacyclopentyl ring;

R' is H, $C_1-C_6$ alkyl, phenyl$(C_1-C_4)$alkyl, $C_1-C_6$ alkanoyl, phenyl$(C_1-C_6)$alkanoyl, pyridyl$(C_1-C_4)$ alkyl, pyrimidyl$(C_1-C_4)$alkyl, pyridazyl$(C_1-C_4)$alkyl, pyrazinyl$(C_1-C_4)$alkyl, thienyl$(C_1-C_4)$alkyl, oxazolyl $(C_1-C_4)$alkyl, thiazolyl$(C_1-C_4)$alkyl, furanyl$(C_1-C_4)$ alkyl, —$SO_2$-alkyl, —$SO_2$-phenyl, —$SO_2$-pyridyl, —$SO_2$-pyrimidyl, —$SO_2$-pyridazyl, —$SO_2$-pyrazinyl, —$SO_2$-thienyl, —$SO_2$-oxazolyl, —$SO_2$-thiazolyl, —$SO_2$-furanyl, pyridyl$(C_1-C_6)$alkanoyl, pyrimidyl$(C_1-C_6)$alkanoyl, pyridazyl$(C_1-C_6)$alkanoyl, pyrazinyl$(C_1-C_6)$alkanoyl, thienyl$(C_1-C_6)$alkanoyl, oxazolyl$(C_1-C_6)$alkanoyl, thiazolyl$(C_1-C_6)$alkanoyl, or furanyl$(C_1-C_6)$alkanoyl, wherein the alkyl portion of the alkyl and alkanoyl groups are optionally substituted with halogen or $C_1-C_6$ alkoxy, wherein the aryl, and heteroaryl groups are optionally substituted with alkyl, alkoxy, halogen, haloalkyl, haloalkoxy, R" is H, or $C_1-C_6$ alkyl, wherein the alkyl group is optionally substituted with halogen.

The compounds of Formula I inhibit β-amyloid peptide release and/or its synthesis and, therefore, are useful in the prevention of Alzheimer's Disease (AD) in patients susceptible to AD and/or in the treatment of patients with AD in order to inhibit further deterioration in their condition. The invention also, encompasses pharmaceutical compositions containing the compounds of Formula I, and methods employing such compounds or compositions in the treatment of cognitive diseases, including Alzheimer's disease.

The invention also provides a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, age related macular degeneration or diffuse Lewy body type of Alzheimer's disease and who is in need of such treatment which comprises administration of a therapeutically effective amount of a compound of formula (I).

In another aspect, the invention provides methods of preparing the compounds of interest, as well as intermediates useful in preparing the compounds of interest.

DETAILED DESCRIPTION OF THE INVENTION

In embodiment 2, the invention provides compounds of formula I wherein $R_1$ is $C_1-C_8$ alkyl which is optionally substituted with 1, 2, or 3 groups that are independently $C_1-C_6$ alkoxy, OH, halogen, CN, $C_1-C_6$ thioalkoxy, phenyl, naphthyl, $C_3-C_8$ cycloalkyl, $NH_2$, $NH(C_1-C_6)$alkyl, $N(C_1-C_6)$alkyl$(C_1-C_6$ alkyl), —C(O)$NH_2$, —C(O)$NH(C_1-C_6)$ alkyl, —C(O)$N(C_1-C_6)$alkyl$(C_1-C_6)$alkyl, —C(O)phenyl, or $C_1-C_6$ alkoxycarbonyl, wherein each of the cyclic groups is optionally substituted with 1, 2, 3, or 4 groups that are independently halogen, $C_1$-$C_4$ alkyl, $C_1$-$C_4$ alkoxy, $NH_2$, $NH(C_1$-$C_6)$ alkyl, $N(C_1$-$C_6)$alkyl($C_1$-$C_6$ alkyl), —$SO_2$—($C_1$-$C_6$) alkyl, or OH.

In embodiment 3, the invention provides compounds according to embodiment 2, wherein $R_3$ is H, halogen, $C_1$-$C_6$ alkyl, $C_1$-$C_6$ alkoxy, $C_1$-$C_6$ haloalkyl, CN;

$R_4$ is H, halogen, $C_1$-$C_6$ alkyl optionally substituted with —$CO_2$—($C_1$-$C_6$ alkyl), $C_1$-$C_6$ alkoxy, $C_1$-$C_4$ haloalkyl, $C_1$-$C_6$ haloalkoxy, CN, aryloxy, isocyanato, —$SO_2$—($C_1$-$C_6$ alkyl), —NHR', —NR'R", $C_1$-$C_6$ alkanoyl, oxazolyl, pyrazolyl, thiazolyl, pyridyl, furanyl or thienyl, phenyl; and $R_{3'}$ is H, or halogen.

Embodiment 3A. Compounds according to embodiment 3, wherein at least one of $R_3$, $R_4$, and $R_{3'}$ is hydrogen. In another aspect, two of $R_3$, $R_4$, and $R_{3'}$ are hydrogen. In still another aspect, $R_4$ is halogen, methyl or $CF_3$. In yet still another aspect, $R_3$ and $R_{3'}$ are hydrogen while $R_4$ is halogen (preferably F or Cl, still more preferably Cl), methyl or $CF_3$. In yet another embodiment $R_4$ is Cl. In another embodiment $R_4$ is methyl. In still another embodiment $R_4$ is $CF_3$.

In embodiment 4, the invention provides compounds according to embodiment 3, wherein $R_2$ is $C_1$-$C_8$ alkyl, or $C_2$-$C_8$ alkenyl, each of which is optionally substituted with 1, 2, or 3 groups that are independently, phenyl 2H-chromenyl, 1,2,3,4-tetrahydronaphthalenyl, indolyl, 3,4-dihydronaphthalenyl, phenyl, naphthyl, $C_3$-$C_8$ cycloalkyl, benzofuranyl, indolyl, 1,4-benzodioxanyl, 1,3-benzodioxolyl, pyridyl, pyrimidyl, $C_1$-$C_4$ alkyl, halogen, —$CO_2$—($C_1$-$C_6$ alkyl), pyrazolyl, imidazolyl, oxazolyl, isoxazolyl, oxadiazolyl, thiazolyl, thiadiazolyl, triazolyl, or CN, wherein the cyclic portions of each of the above are optionally substituted with 1, 2, or 3 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$) alkyl ($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl ($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 4A. Compounds according to embodiment 4, wherein $R_1$ is $C_1$-$C_8$ alkyl which is optionally substituted with 1, 2, or 3 groups that are independently $C_1$-$C_4$ alkoxy, OH, halogen, CN, $C_1$-$C_4$ thioalkoxy, naphthyl, $C_3$-$C_8$ cycloalkyl, $NH_2$, $NH(C_1$-$C_6)$alkyl, $N(C_1$-$C_6)$alkyl($C_1$-$C_6$ alkyl), —C(O)$NH_2$, —C(O)NH($C_1$-$C_6$)alkyl, —C(O)N($C_1$-$C_6$)alkyl($C_1$-$C_6$)alkyl, —C(O)phenyl, or $C_1$-$C_6$ alkoxycarbonyl, wherein each of the cyclic groups is optionally substituted with 1, 2, or 3 groups that are independently halogen, $C_1$-$C_4$ alkyl, $C_1$-$C_4$ alkoxy, $NH_2$, $NH(C_1$-$C_6)$ alkyl, $N(C_1$-$C_6)$alkyl($C_1$-$C_6$ alkyl), —$SO_2$—($C_1$-$C_6$) alkyl, or OH.

Embodiment 4B. Compounds according to Embodiment 4, wherein $R_1$ is $C_1$-$C_8$ alkyl which is optionally substituted with 1, 2, or 3 groups that are independently $C_1$-$C_4$ alkoxy, OH, halogen, CN, $C_1$-$C_4$ thioalkoxy, $NH_2$, $NH(C_1$-$C_6)$alkyl, $N(C_1$-$C_6)$alkyl($C_1$-$C_6$ alkyl), —C(O)$NH_2$, —C(O)NH($C_1$-$C_6$)alkyl, —C(O)N($C_1$-$C_6$)alkyl($C_1$-$C_6$)alkyl, —C(O)phenyl, or $C_1$-$C_4$ alkoxycarbonyl.

Embodiment 4C. Compounds according to Embodiment 4, wherein $R_1$ is $C_1$-$C_8$ alkyl which is optionally substituted with 1, or 2 groups that are independently $C_1$-$C_4$ alkoxy, OH, halogen, CN, $C_1$-$C_4$ thioalkoxy, $NH_2$, $NH(C_1$-$C_4)$alkyl, $N(C_1$-$C_4)$alkyl($C_1$-$C_4$ alkyl), —C(O)$NH_2$, —C(O)NH($C_1$-$C_4$)alkyl, —C(O)N($C_1$-$C_4$)alkyl($C_1$-$C_4$)alkyl, or $C_1$-$C_4$ alkoxycarbonyl.

Embodiment 4D. Compounds according to Embodiment 4, wherein $R_1$ is $C_1$-$C_8$ alkyl which is optionally substituted with 1 or 2 groups that are independently $C_1$-$C_4$ alkoxy, OH, halogen, CN, $C_1$-$C_4$ thioalkoxy, $NH_2$, $NH(C_1$-$C_4)$alkyl, or $N(C_1$-$C_4)$alkyl($C_1$-$C_4$ alkyl).

Embodiment 4E. Compounds according to Embodiment 4, wherein $R_1$ is $C_1$-$C_8$ alkyl which is optionally substituted with 1, or 2 groups that are independently $C_1$-$C_4$ alkoxy, OH, halogen, CN, or $C_1$-$C_4$ thioalkoxy.

Embodiment 4F. Compounds according to Embodiment 4, wherein $R_1$ is $C_1$-$C_8$ alkyl which is optionally substituted with 1, or 2 groups that are independently $NH_2$, $NH(C_1$-$C_4)$alkyl, or $N(C_1$-$C_4)$alkyl($C_1$-$C_4$ alkyl).

Embodiment 4G. Compounds according to Embodiment 4, wherein $R_1$ is $C_1$-$C_8$ alkyl which is optionally substituted with 1, or 2 groups that are independently —C(O)$NH_2$, —C(O)NH($C_1$-$C_4$) alkyl, —C(O)N($C_1$-$C_4$)alkyl($C_1$-$C_4$)alkyl, or $C_1$-$C_4$ alkoxycarbonyl.

Embodiment 4H. Compounds according to Embodiment 4, wherein $R_1$ is $C_1$-$C_8$ alkyl substituted with $C_3$-$C_8$ cycloalkyl which is optionally substituted with 1, or 2 groups that are independently halogen, $C_1$-$C_4$ alkyl, $C_1$-$C_4$ alkoxy, $NH_2$, $NH(C_1$-$C_6)$alkyl, $N(C_1$-$C_6)$alkyl($C_1$-$C_6$ alkyl), or OH.

In embodiment 5, the invention provides compounds according to embodiment 4, wherein $R_1$ is $C_1$-$C_8$ alkyl which is optionally substituted with OH.

In embodiment 6, the invention provides compounds according to embodiment 5, wherein $R_3$ is H, halogen, $C_1$-$C_6$ alkyl, $C_1$-$C_6$ alkoxy, $CF_3$, CN;

$R_4$ is H, halogen, $C_1$-$C_6$ alkoxy, $C_1$-$C_6$ alkyl, $CF_3$, $OCF_3$, CN, phenyloxy, —$SO_2$—($C_1$-$C_6$ alkyl), —NHR', —NR'R", $C_1$-$C_4$ alkanoyl, pyridyl, furanyl or thienyl, phenyl, or $C_1$-$C_6$ alkyl optionally substituted with —$CO_2$—($C_1$-$C_6$ alkyl);

$R_{3'}$ is H, or halogen;

R' is H, $C_1$-$C_6$ alkyl, phenyl($C_1$-$C_4$)alkyl, $C_1$-$C_6$ alkanoyl, phenyl($C_1$-$C_4$)alkanoyl, pyridyl($C_1$-$C_4$) alkyl, —$SO_2$-alkyl, —$SO_2$-phenyl, —$SO_2$-pyridyl, pyridyl($C_1$-$C_6$)alkanoyl, wherein the alkyl portion of the alkyl and alkanoyl groups are optionally substituted with halogen or $C_1$-$C_4$ alkoxy, wherein the phenyl and pyridyl groups are optionally substituted with $C_1$-$C_4$ alkyl, $C_1$-$C_4$ alkoxy, halogen, $CF_3$, $OCF_3$;

R" is H or $C_1$-$C_6$ alkyl, wherein the alkyl group is optionally substituted with halogen.

Embodiment 6A. Compounds according to embodiment 6, wherein
$R_1$ is $C_1$-$C_8$ hydroxyalkyl. In one aspect, $R_1$ is $C_2$-$C_6$ hydroxyalkyl. In another aspect, $R_1$ is a $C_3$-$C_6$ hydroxyalkyl. In still another aspect, $R_1$ is a $C_5$-$C_6$ hydroxyalkyl. In another aspect, $R_1$ is a $C_7$-$C_8$ hydroxyalkyl. In yet another aspect, $R_1$ is

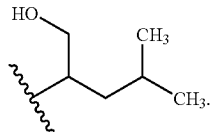

Embodiment 6B. Compounds according to embodiment 6, wherein
$R_1$ is $C_1$-$C_8$ alkyl. In another aspect, $R_1$ is a $C_3$-$C_6$ alkyl. In still another aspect, $R_1$ is a $C_5$-$C_6$ alkyl. In another aspect, $R_1$ is $C_5$-$C_8$ alkyl. In still another aspect, $R_1$ is $C_7$-$C_8$ alkyl.

Embodiment 6C. Compounds according to either Embodiment 6A or Embodiment 6B, wherein $R_2$ is $C_1$-$C_8$ alkyl. In another aspect, the $R_2$ is $C_2$-$C_8$ alkyl. In still another aspect, $R_2$ is $C_2$-$C_6$ alkyl. In yet another aspect, $R_2$ is $C_3$-$C_4$ alkyl (preferably, $C_3$ alkyl.) In another aspect, $R_2$ is $C_1$, $C_3$, or $C_5$ alkyl. In still another aspect, $R_2$ is n-propyl or isopropyl. In another aspect, $R_2$ is $C_3$-$C_8$ alkyl. In yet another aspect, $R_2$ is $C_5$-$C_8$ alkyl. In still another aspect, $R_2$ is $C_7$-$C_8$ alkyl. In still another aspect, $R_2$ is $C_5$-$C_7$ alkyl.

Embodiment 6D. Compounds according to Embodiment 6C, wherein $R_3$ is H, halogen, methyl, methoxy, or $CF_3$;
$R_4$ is H, halogen (preferably Cl or F, more preferably Cl), methoxy, methyl, or $CF_3$; and
$R_{3'}$ is H, or halogen.

Embodiment 6E. Compounds according to Embodiment 6D, wherein $R_3$ and $R_{3'}$ are both H; and $R_4$ is halogen (preferably Cl or F, more preferably Cl), methoxy, methyl, or $CF_3$. In one aspect, $R_4$ is Cl. In another aspect, $R_4$ is methyl. In still another aspect, $R_4$ is $CF_3$.

In embodiment 7, the invention provides compounds according to embodiment 6, wherein
$R_2$ is $C_1$-$C_8$ alkyl which is optionally substituted with 1 or 2 phenyl groups, 2H-chromenyl, 1,2,3,4-tetrahydronaphthalenyl, indolyl, 3,4-dihydronaphthalenyl, phenyl, naphthyl, $C_3$-$C_8$ cycloalkyl, benzofuranyl, indolyl, 1,4-benzodioxanyl, 1,3-benzodioxolyl, pyridyl, pyrimidyl, triazolyl, or CN,
wherein the cyclic portions of each of the above are optionally substituted with 1, 2, or 3 groups that are independently halogen, $CO_2H$, $C_1$-$C_6$ alkoxycarbonyl, —C(O)NH_2, —C(O)NH($C_1$-$C_6$) alkyl, —C(O)N($C_1$-$C_6$) alkyl ($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 7A. Compounds according to embodiment 7, wherein
$R_2$ is $C_1$-$C_8$ alkyl which is optionally substituted with 2 H-chromenyl, 1,2,3,4-tetrahydronaphthalenyl, indolyl, 3,4-dihydronaphthalenyl, naphthyl, $C_3$-$C_8$ cycloalkyl, benzofuranyl, indolyl, 1,4-benzodioxanyl, 1,3-benzodioxolyl, pyridyl, triazolyl, or pyrimidyl,
wherein the cyclic portions of each of the above are optionally substituted with 1, 2, or 3 groups that are independently halogen, $CO_2H$, $C_1$-$C_6$ alkoxycarbonyl, —C(O)NH_2, —C(O)NH($C_1$-$C_6$) alkyl, —C(O)N($C_1$-$C_6$) alkyl ($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 7B. Compounds according to embodiment 7, or embodiment 7A, wherein
$R_2$ is $C_1$-$C_4$ alkyl which is optionally substituted with 1,4-benzodioxanyl, or 1,3-benzodioxolyl,
wherein the cyclic portions of each of the above are optionally substituted with 1, 2, or 3 groups that are independently halogen, $CO_2H$, $C_1$-$C_6$ alkoxycarbonyl, —C(O)NH_2, —C(O)NH($C_1$-$C_6$) alkyl, —C(O)N($C_1$-$C_6$) alkyl ($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl. In another aspect, the cyclic portions are unsubstituted.

Embodiment 7C. Compounds according to embodiment 7, or Embodiment 7A, wherein
$R_2$ is $C_1$-$C_4$ alkyl which is substituted with 2H-chromenyl, 1,2,3,4-tetrahydronaphthalenyl, indolyl, 3,4-dihydronaphthalenyl, naphthyl, or $C_3$-$C_8$ cycloalkyl,
wherein the cyclic portions of each of the above are optionally substituted with 1, 2, or 3 groups that are independently halogen, $CO_2H$, $C_1$-$C_6$ alkoxycarbonyl, —C(O)NH_2, —C(O)NH($C_1$-$C_6$) alkyl, —C(O)N($C_1$-$C_6$) alkyl ($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl. In another aspect, $R_{25}$ is $C_1$-$C_6$ alkyl or OH.

Embodiment 7d. Compounds according to Embodiment 7A, wherein $R_2$ is $C_1$-$C_4$ alkyl which is substituted with 2 H-chromenyl, 1,2,3,4-tetrahydronaphthalenyl, indolyl, 3,4-dihydronaphthalenyl, naphthyl, $C_3$-$C_8$ cycloalkyl, benzofuranyl, indolyl, 1,4-benzodioxanyl, 1,3-benzodioxolyl, pyridyl, triazolyl, or pyrimidyl, each of which is unsubstituted.

Embodiment 7e. Compounds according to Embodiment 7A, wherein $R_2$ is $C_1$-$C_2$ alkyl which is substituted with 2 H-chromenyl, 1,2,3,4-tetrahydronaphthalenyl, indolyl, 3,4-dihydronaphthalenyl, naphthyl, $C_3$-$C_8$ cycloalkyl, benzofuranyl, indolyl, 1,4-benzodioxanyl, 1,3-benzodioxolyl, pyridyl, or pyrimidyl, each of which is unsubstituted.

Embodiment 7f. Compounds according to Embodiment 7A, wherein $R_2$ is $C_1$-$C_2$ alkyl which is substituted with 2 H-chromenyl, 1,2,3,4-tetrahydronaphthalenyl, indolyl, 3,4-dihydronaphthalenyl, naphthyl, benzofuranyl, indolyl, 1,4-benzodioxanyl, or 1,3-benzodioxolyl, each of which is unsubstituted.

In embodiment 8, the invention provides compounds according to embodiment 7, wherein
$R_2$ is $C_1$-$C_8$ alkyl which is optionally substituted with phenyl group, benzofuranyl, 1,4-benzodioxanyl, or 1,3-benzodioxolyl,
wherein the cyclic portions of each of the above are optionally substituted with 1, 2, or 3 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$) alkyl ($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 8A. Compounds according to embodiment 8, wherein
$R_2$ is $C_1$-$C_8$ alkyl substituted with phenyl, benzofuranyl, 1,4-benzodioxanyl, or 1,3-benzodioxolyl. In another aspect, the alkyl group is $C_1$-$C_4$ alkyl. In still another aspect, the alkyl group is $C_2$-$C_5$ alkyl. In yet still another aspect, the alkyl group is $C_3$-$C_5$ alkyl. In another aspect, $R_2$ is $C_3$-$C_8$ alkyl. In yet another aspect, $R_2$ is $C_5$-$C_8$ alkyl. In still another aspect, $R_2$ is $C_7$-$C_8$ alkyl. In still another aspect, $R_2$ is $C_5$-$C_7$ alkyl.

Embodiment 8B. Compounds according to embodiment 8, wherein
$R_2$ is $C_1$-$C_8$ alkyl substituted with 1,4-benzodioxanyl, or 1,3-benzodioxolyl. In another aspect, the alkyl group is $C_1$-$C_4$ alkyl. In still another aspect, the alkyl group is $C_2$-$C_5$ alkyl. In yet still another aspect, the alkyl group is $C_3$-$C_5$ alkyl. In another aspect, $R_2$ is $C_3$-$C_8$ alkyl. In yet another aspect, $R_2$ is $C_5$-$C_8$ alkyl. In still another aspect, $R_2$ is $C_7$-$C_8$ alkyl. In still another aspect, $R_2$ is $C_5$-$C_7$ alkyl.

In embodiment 9, the invention provides compounds according to embodiment 8, wherein
$R_2$ is $C_1$-$C_8$ alkyl substituted with phenyl, wherein the phenyl is optionally substituted with 1, 2, or 3 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$) alkyl($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 9A. Compounds according to embodiment 9, wherein
$R_2$ is $C_1$-$C_4$ alkyl (in another aspect, $C_1$-$C_2$ alkyl) substituted with phenyl, wherein the phenyl is optionally substituted with 1, 2, or 3 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$) alkyl ($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 9B. Compounds according to embodiment 9, wherein
$R_2$ is $C_3$-$C_6$ alkyl (in another aspect, $C_3$-$C_5$ alkyl) substituted with phenyl, wherein the phenyl is optionally substituted with 1, 2, or 3 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$)alkyl($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 9C. Compounds according to embodiment 9, wherein
$R_2$ is $C_5$-$C_8$ alkyl (in another aspect, $C_5$-$C_7$ alkyl) substituted with phenyl, wherein the phenyl is optionally substituted with 1, 2, or 3 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$)alkyl($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

In embodiment 10, the invention provides compounds according to embodiment 9, wherein
$R_1$ is $C_1$-$C_8$ hydroxyalkyl;
$R_3$ is H, halogen, $C_1$-$C_4$ alkyl, $C_1$-$C_4$ alkoxy, $CF_3$, CN;
$R_4$ is H, halogen, $C_1$-$C_4$ alkoxy, $CF_3$, $OCF_3$, CN, phenyloxy, —$SO_2$—($C_1$-$C_6$ alkyl), —NHR', —NR'R'', $C_1$-$C_4$ alkanoyl, pyridyl, furanyl or thienyl, phenyl, or $C_1$-$C_6$ alkyl optionally substituted with —$CO_2$—($C_1$-$C_6$ alkyl);
$R_{3'}$ is H, or halogen;

R' is H, $C_1$-$C_4$ alkyl, benzyl, $C_1$-$C_6$ alkanoyl, phenyl($C_1$-$C_4$) alkanoyl, pyridyl($C_1$-$C_4$)alkyl, —$SO_2$-alkyl, —$SO_2$-phenyl, —$SO_2$-pyridyl, pyridyl($C_1$-$C_6$)alkanoyl, wherein the alkyl portion of the alkyl and alkanoyl groups are optionally substituted with halogen or $C_1$-$C_4$ alkoxy,
  wherein the phenyl and pyridyl groups are optionally substituted with $C_1$-$C_4$ alkyl, $C_1$-$C_4$ alkoxy, halogen, $CF_3$, $OCF_3$;
R" is H or $C_1$-$C_6$ alkyl, wherein the alkyl group is optionally substituted with halogen.

In embodiment 11, the invention provides compounds according to embodiment 10, wherein
$R_1$ is

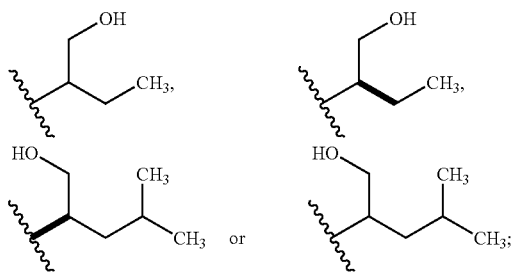

$R_3$ is H, halogen, methyl, methoxy, $CF_3$, or CN;
$R_4$ is H, halogen, methyl, methoxy, $CF_3$, $OCF_3$, CN, —NHR', or —NR'R";
$R_{3'}$ is H, or halogen;
  R' is H, or $C_1$-$C_4$ alkyl; and
  R" is H or $C_1$-$C_6$ alkyl, wherein the alkyl group is optionally substituted with halogen.

Embodiment 11A. Compounds according to embodiment 11, wherein
  $R_2$ is $C_1$-$C_2$ alkyl substituted with phenyl, wherein the phenyl is optionally substituted with 1, 2, or 3 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$)alkyl($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
  x is 0, 1, or 2;
  $R_{25}$ is $C_1$-$C_6$ alkyl, OH, $NR_{26}R_{27}$;
  $R_{26}$ and $R_{27}$ are independently H, $C_1$-$C_6$ alkyl, phenyl($C_1$-$C_4$ alkyl), phenyl, or pyridyl; or
  $R_{26}$, $R_{27}$ and the nitrogen to which they are attached represent pyrrolidinyl, piperidinyl, piperazinyl, morpholinyl, or imidazolidinyl.

Embodiment 11B. Compounds according to Embodiment 11A, wherein $R_2$ is $C_1$-$C_2$ alkyl substituted with phenyl, wherein the phenyl is unsubstituted.

Embodiment 11C. Compounds according to embodiment 11A, wherein $R_2$ is $C_1$-$C_2$ alkyl substituted with phenyl, wherein the phenyl is substituted with 1, or 2 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$) alkyl($C_1$-$C_4$) alkyl, $C_1$-$C_3$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein x is 0, 1, or 2; $R_{25}$ is $C_1$-$C_6$ alkyl, OH, $NR_{26}R_{27}$; $R_{26}$ and $R_{27}$ are independently H, $C_1$-$C_6$ alkyl, phenyl($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 11D. Compounds according to embodiment 11C, wherein $R_2$ is $C_1$-$C_2$ alkyl substituted with phenyl, wherein the phenyl is substituted with 1 or 2 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$) alkyl($C_1$-$C_4$) alkyl, $C_1$-$C_2$ alkoxy, $C_1$-$C_4$ alkyl, —S(O)$_x$—$R_{25}$, —($C_1$-$C_4$ alkyl)-S(O)$_x$—$R_{25}$, or OH; wherein x is 0, 1, or 2; $R_{25}$ is $C_1$-$C_6$ alkyl, OH, $NR_{26}R_{27}$; $R_{26}$ and $R_{27}$ are independently H, $C_1$-$C_6$ alkyl, phenyl($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 11D1. Compounds according to embodiment 11C, wherein $R_2$ is $C_1$-$C_2$ alkyl substituted with phenyl, wherein the phenyl is substituted with 1 group that is halogen (in one aspect, F, Cl or Br), $C_1$-$C_4$ alkoxy (in one aspect, methoxy), or $C_1$-$C_4$ alkyl (in one aspect, methyl.) In another embodiment, the substituent is in the para position.

Embodiment 11E. Compounds according to embodiment 11D, wherein $R_2$ is $C_1$-$C_2$ alkyl substituted with phenyl, wherein the phenyl is substituted with 2 groups, one of which is a halogen or a methoxy group. In another aspect, the second group is a halogen or a methoxy group. In still another aspect, the phenyl is substituted with two halogens or two methoxy groups.

Embodiment 11F. Compounds according to embodiment 11D, wherein $R_2$ is $C_1$-$C_2$ alkyl substituted with phenyl, wherein the phenyl is substituted with 1, or 2 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$) alkyl($C_1$-$C_6$) alkyl, methoxy, or $C_1$-$C_2$ alkoxy optionally substituted with pyridyl, thiazolyl, or methyl thiazol-5-yl. In another aspect, the phenyl is di-substituted and one of the groups is methoxy. In yet another aspect, the phenyl is di-substituted, one of the groups is methoxy and the other group is $C_1$-$C_2$ alkoxy substituted with pyridyl, thiazolyl, methyl thiazol-5-yl. In one aspect, the other group is $C_1$ alkoxy substituted with pyridyl, or methyl thiazol-5-yl. In yet another aspect, the other group is $C_2$ alkoxy substituted with pyridyl, or methyl thiazol-5-yl.

Embodiment 11G. Compounds according to Embodiment 11, wherein
  $R_2$ is $C_3$-$C_5$ alkyl substituted with phenyl, wherein the phenyl is optionally substituted with 1, 2, or 3 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$)alkyl($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
  x is 0, 1, or 2;
  $R_{25}$ is $C_1$-$C_6$ alkyl, OH, $NR_{26}R_{27}$;
  $R_{26}$ and $R_{27}$ are independently H, $C_1$-$C_6$ alkyl, phenyl ($C_1$-$C_4$ alkyl), phenyl, or pyridyl; or
  $R_{26}$, $R_{27}$ and the nitrogen to which they are attached represent pyrrolidinyl, piperidinyl, piperazinyl, morpholinyl, or imidazolidinyl.

Embodiment 11H. Compounds according to Embodiment 11G, wherein
  $R_2$ is $C_3$-$C_4$ alkyl substituted with phenyl, wherein the phenyl is optionally substituted with 1, 2, or 3 groups that are independently halogen, $CO_2H$, $C_1$-$C_6$ alkoxycarbonyl, —C(O)$NH_2$, —C(O)NH($C_1$-$C_6$) alkyl, —C(O)N($C_1$-$C_6$)alkyl($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—R$_{25}$, —($C_1$-$C_4$ alkyl)-S(O)$_x$—R$_{25}$, or OH; wherein x is 0, 1, or 2;

R$_{25}$ is $C_1$-$C_6$ alkyl, OH, NR$_{26}$R$_{27}$;

R$_{26}$ and R$_{27}$ are independently H, $C_1$-$C_6$ alkyl, phenyl ($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

Embodiment 11I. Compounds according to Embodiment 11H, wherein R$_2$ is $C_3$-$C_4$ alkyl substituted with phenyl, wherein the phenyl is unsubstituted. In one aspect, the $C_3$ alkyl group is a straight chained alkyl group. In another aspect, the $C_4$ alkyl group is a straight chained $C_3$ alkyl group substituted with a methyl group.

Embodiment 11J. Compounds according to embodiment 11H, wherein

R$_2$ is $C_3$-$C_4$ alkyl substituted with phenyl, wherein the phenyl is substituted with 1, or 2 groups that are independently halogen, CO$_2$H, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_3$ alkoxy optionally substituted with pyridyl, thiazolyl, or methyl thiazol-5-yl, $C_1$-$C_4$ alkyl, —S(O)$_x$—R$_{25}$, —($C_1$-$C_4$ alkyl)-S(O)$_x$—R$_{25}$, or OH; wherein x is 0, 1, or 2;

R$_{25}$ is $C_1$-$C_6$ alkyl, OH, NR$_{26}$R$_{27}$;

R$_{26}$ and R$_{27}$ are independently H, $C_1$-$C_6$ alkyl, phenyl ($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

Embodiment 11K. Compounds according to embodiment 11J, wherein

R$_2$ is $C_3$-$C_4$ alkyl substituted with phenyl, wherein the phenyl is substituted with 1, or 2 groups that are independently halogen, CO$_2$H, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_2$ alkoxy, $C_1$-$C_4$ alkyl, —S(O)$_x$—R$_{25}$, —($C_1$-$C_4$ alkyl)-S(O)$_x$—R$_{25}$, or OH; wherein x is 0, 1, or 2;

R$_{25}$ is $C_1$-$C_6$ alkyl, OH, NR$_{26}$R$_{27}$;

R26 and R$_{27}$ are independently H, $C_1$-$C_6$ alkyl, phenyl ($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

Embodiment 11L. Compounds according to embodiment 11K, wherein R$_2$ is $C_3$-$C_4$ alkyl substituted with phenyl, wherein the phenyl is substituted with 2 groups, one of which is a halogen or a methoxy group. In another aspect, the second group is a halogen or a methoxy group. In still another aspect, the phenyl is substituted with two halogens or two methoxy groups.

Embodiment 11M. Compounds according to embodiment 11J, wherein R$_2$ is $C_3$-$C_4$ alkyl substituted with phenyl, wherein the phenyl is substituted with 1, or 2 groups that are independently halogen, methoxy, or $C_1$-$C_2$ alkoxy optionally substituted with pyridyl, thiazolyl, or methyl thiazol-5-yl. In another aspect, the phenyl is di-substituted and one of the groups is methoxy. In yet another aspect, the phenyl is di-substituted, one of the groups is methoxy and the other group is $C_1$-$C_2$ alkoxy substituted with pyridyl, thiazolyl, methyl thiazol-5-yl. In one aspect, the other group is $C_1$ alkoxy substituted with pyridyl, or methyl thiazol-5-yl. In yet another aspect, the other group is $C_2$ alkoxy substituted with pyridyl, or methyl thiazol-5-yl.

Embodiment 11N. Compounds according to any one of embodiments 11A, 11B, 11C, 11D, 11E, 11F, 11G, 11H, 11I, 11J, 11K, or 11L wherein R$_3$ is H, or halogen; R$_4$ is halogen, methyl, CF$_3$, or methoxy; and R$_{3'}$ is H, or halogen.

Embodiment 11O. Compounds according to embodiment 11N, wherein R$_3$ is H; R$_4$ is halogen (preferably F or Cl, more preferably Cl), methyl of CF$_3$; and R$_{3'}$ is H. In another aspect, R$_4$ is methyl. In still another aspect, R$_4$ is CF$_3$. In yet another aspect, R$_4$ is Cl.

In embodiment 12, the invention provides compounds according to embodiment 5, wherein R$_1$ is $C_1$-$C_8$ alkyl;

R$_2$ is $C_1$-$C_8$ alkyl substituted with a phenyl group, benzofuranyl, 1,4-benzodioxanyl, or 1,3-benzodioxolyl, wherein the phenyl group is optionally substituted with 1, 2, or 3 groups that are independently halogen, CO$_2$H, $C_1$-$C_6$ alkoxycarbonyl, —C(O)NH$_2$, —C(O)NH($C_1$-$C_6$) alkyl, —C(O)N($C_1$-$C_6$)alkyl($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—R$_{25}$, —($C_1$-$C_4$ alkyl)-S(O)$_x$—R$_{25}$, or OH; wherein x is 0, 1, or 2;

R$_{25}$ is $C_1$-$C_6$ alkyl, OH, NR$_{26}$R$_{27}$;

R$_{26}$ and R$_{27}$ are independently H, $C_1$-$C_6$ alkyl, phenyl ($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl;

R$_3$ is H, halogen, $C_1$-$C_4$ alkyl, $C_1$-$C_4$ alkoxy, CF$_3$, CN;

R$_4$ is H, halogen, $C_1$-$C_4$ alkoxy, CF$_3$, OCF$_3$, CN, phenyloxy, —SO$_2$—($C_1$-$C_6$ alkyl), —NHR', —NR'R", $C_1$-$C_4$ alkanoyl, pyridyl, furanyl or thienyl, phenyl, or $C_1$-$C_4$ alkyl optionally substituted with —CO$_2$—($C_1$-$C_6$ alkyl);

R$_{3'}$ is H, or halogen;

R' is H, $C_1$-$C_4$ alkyl, benzyl, $C_1$-$C_6$ alkanoyl, phenyl($C_1$-$C_4$) alkanoyl, pyridyl($C_1$-$C_4$)alkyl, —SO$_2$-alkyl, —SO$_2$-phenyl, —SO$_2$-pyridyl, pyridyl($C_1$-$C_6$)alkanoyl, wherein the alkyl portion of the alkyl and alkanoyl groups are optionally substituted with halogen or $C_1$-$C_4$ alkoxy, wherein the phenyl and pyridyl groups are optionally substituted with $C_1$-$C_4$ alkyl, $C_1$-$C_4$ alkoxy, halogen, CF$_3$, OCF$_3$;

R" is H or $C_1$-$C_6$ alkyl, wherein the alkyl group is optionally substituted with halogen.

In embodiment 13, the invention provides compounds according to embodiment 12, wherein R$_1$ is $C_2$-$C_8$ alkyl;

R$_3$ is H, halogen, methyl, methoxy, CF$_3$, or CN;

R$_4$ is halogen, methyl, methoxy, CF$_3$, OCF$_3$, CN, —NHR', or —NR'R";

R$_{3'}$ is H, or halogen;

R' is H, or $C_1$-$C_4$ alkyl; and

R" is H or $C_1$-$C_6$ alkyl, wherein the alkyl group is optionally substituted with halogen.

Embodiment 13A. Compounds according to embodiment 13, wherein

R$_2$ is $C_1$-$C_2$ alkyl substituted with phenyl, wherein the phenyl is optionally substituted with 1, 2, or 3 groups that are independently halogen, CO$_2$H, $C_1$-$C_6$ alkoxycarbonyl, —C(O)NH$_2$, —C(O)NH($C_1$-$C_6$) alkyl, —C(O)N($C_1$-$C_6$)alkyl($C_1$-$C_6$) alkyl, $C_1$-$C_4$ alkoxy optionally substituted with pyridyl, thiazolyl, or methyl thiazol-5-yl, $C_1$-$C_4$ alkyl, —S(O)$_x$—R$_{25}$, —($C_1$-$C_4$ alkyl)-S(O)$_x$—R$_{25}$, or OH; wherein x is 0, 1, or 2;

R$_{25}$ is $C_1$-$C_6$ alkyl, OH, NR$_{26}$R$_{27}$;

R$_{26}$ and R$_{27}$ are independently H, $C_1$-$C_6$ alkyl, phenyl ($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

Embodiment 13B. Compounds according to Embodiment 13A, wherein R$_2$ is $C_1$-$C_2$ alkyl substituted with phenyl, wherein the phenyl is unsubstituted.

Embodiment 13C. Compounds according to embodiment 13A, wherein R$_2$ is $C_1$-$C_2$ alkyl substituted with phenyl, wherein the phenyl is substituted with 1, or 2 groups that are independently halogen, CO$_2$H, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_3$ alkoxy optionally substituted with pyridyl, thiazolyl, or methyl thiazol-5-yl, $C_1$-$C_4$ alkyl, —S(O)$_x$—R$_{25}$, —($C_1$-$C_4$ alkyl)-S(O)$_x$—R$_{25}$, or OH; wherein x is 0, 1, or 2;

R$_{25}$ is $C_1$-$C_6$ alkyl, OH, NR$_{26}$R$_{27}$;

R$_{26}$ and R$_{27}$ are independently H, $C_1$-$C_6$ alkyl, phenyl($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

Embodiment 13D. Compounds according to embodiment 13C, wherein

R$_2$ is $C_1$-$C_2$ alkyl substituted with phenyl, wherein the phenyl is substituted with 1, or 2 groups that are independently halogen, CO$_2$H, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_2$ alkoxy, $C_1$-$C_4$ alkyl, —S(O)$_x$—R$_{25}$, —($C_1$-$C_4$ alkyl)-S(O)$_x$—R$_{25}$, or OH; wherein x is 0, 1, or 2;

R$_{25}$ is $C_1$-$C_6$ alkyl, OH, NR$_{26}$R$_{27}$;

R$_{26}$ and R$_{27}$ are independently H, $C_1$-$C_6$ alkyl, phenyl ($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

Embodiment 13E. Compounds according to embodiment 13D, wherein R$_2$ is $C_1$-$C_2$ alkyl substituted with phenyl, wherein the phenyl is substituted with 2 methoxy groups.

Embodiment 13E1. Compounds according to Embodiment 13D, wherein R$_2$ is $C_1$-$C_2$ alkyl substituted with phenyl, wherein the phenyl is substituted with 1 or 2 groups that are independently CO$_2$H, $C_1$-$C_4$ alkoxycarbonyl, —C(O)NH$_2$, —C(O)NH($C_1$-$C_4$) alkyl, or —C(O)N($C_1$-$C_4$)alkyl($C_1$-$C_4$) alkyl. In another aspect, the $C_1$-$C_4$ alkoxycarbonyl is a methoxy carbonyl or ethoxycarbonyl. More preferably, it is ethoxycarbonyl.

Embodiment 13E2. Compounds according to Embodiment 13D, wherein R$_2$ is $C_1$-$C_2$ alkyl substituted with phenyl, wherein the phenyl is substituted with 1 or 2 groups that are independently CO$_2$H, —C(O)NH$_2$, —C(O)NH($C_1$-$C_4$)alkyl, or —C(O)N($C_1$-$C_4$)alkyl($C_1$-$C_4$)alkyl. In another aspect, the phenyl group is substituted with 1 group selected that is CO$_2$H, —C(O)NH$_2$, —C(O)NH($C_1$-$C_4$)alkyl, or —C(O)N ($C_1$-$C_4$)alkyl($C_1$-$C_4$)alkyl.

Embodiment 13E3. Compounds according to Embodiment 13D, wherein

R$_2$ is $C_1$-$C_2$ alkyl substituted with phenyl, wherein the phenyl is substituted with 1 or 2 groups that are independently halogen, CO$_2$H, $C_1$-$C_4$ alkoxycarbonyl, —S(O)$_x$—R$_{25}$, —($C_1$-$C_4$ alkyl)-S(O)$_x$—R$_{25}$, or OH; wherein x is 0, 1, or 2;

R$_{25}$ is $C_1$-$C_6$ alkyl, OH, NR$_{26}$R$_{27}$;

R$_{26}$ and R$_{27}$ are independently H, $C_1$-$C_6$ alkyl, phenyl ($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

Embodiment 13E4. Compounds according to embodiment 13D, wherein R$_2$ is $C_1$-$C_2$ alkyl substituted with phenyl, wherein the phenyl is substituted with 1 or 2 groups that are independently halogen, —C(O)NH$_2$, —C(O)NH($C_1$-$C_4$) alkyl, —C(O)N($C_1$-$C_4$)alkyl($C_1$-$C_4$) alkyl, or OH.

Embodiment 13E5. Compounds according to Embodiment 13D, wherein R$_2$ is $C_1$-$C_2$ alkyl substituted with phenyl, wherein the phenyl is substituted with 1 or 2 groups that are independently —S(O)$_x$—R$_{25}$, —($C_1$-$C_4$ alkyl)-S(O)$_x$—R$_{25}$, or OH; wherein x is 0, 1, or 2;

R$_{25}$ is $C_1$-$C_6$ alkyl, OH, NR$_{26}$R$_{27}$;

R$_{26}$ and R$_{27}$ are independently H, $C_1$-$C_6$ alkyl, phenyl($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

Embodiment 13E6. Compounds according to Embodiment 13D, wherein

R$_2$ is $C_1$-$C_2$ alkyl substituted with phenyl, wherein the phenyl is substituted with 1 or 2 groups that are independently —S(O)$_x$—R$_{25}$, or —($C_1$-$C_4$ alkyl)-S(O)$_x$—R$_{25}$; wherein x is 0, or 2; and R$_{25}$ is $C_1$-$C_6$ alkyl, or OH.

Embodiment 13E7. Compounds according to Embodiment 13D, wherein R$_2$ is $C_1$-$C_2$ alkyl substituted with phenyl, wherein the phenyl is substituted with NR$_{26}$R$_{27}$; wherein R$_{26}$ and R$_{27}$ are independently H, $C_1$-$C_6$ alkyl, phenyl($C_1$-$C_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

Embodiment 13E8. Compounds according to Embodiment 13D, wherein R$_2$ is $C_1$-$C_2$ alkyl substituted with phenyl, wherein the phenyl is substituted with NR$_{26}$R$_{27}$; wherein R$_{26}$ and R$_{27}$ are independently H, $C_1$-$C_6$ alkyl, phenyl($C_1$-$C_4$ alkyl), phenyl, or pyridyl.

Embodiment 13E9. Compounds according to Embodiment 13D, wherein R$_2$ is $C_1$-$C_2$ alkyl substituted with phenyl, wherein the phenyl is substituted with NR$_{26}$R$_{27}$; wherein R$_{26}$, R$_{27}$ and the nitrogen to which they are attached represent pyrrolidinyl, piperidinyl, piperazinyl, morpholinyl, or imidazolidinyl.

Embodiment 13F. Compounds according to embodiment 13D, wherein R$_2$ is $C_1$-$C_2$ alkyl substituted with phenyl, wherein the phenyl is substituted with 1, or 2 groups that are independently halogen, CO$_2$H, $C_1$-$C_4$ alkoxycarbonyl, —C(O)NH$_2$, —C(O)NH($C_1$-$C_4$) alkyl, —C(O)N($C_1$-$C_4$) alkyl($C_1$-$C_4$) alkyl, methoxy, or $C_1$-$C_2$ alkoxy optionally substituted with pyridyl, thiazolyl, methyl thiazol-5-yl. In another aspect, the phenyl is di-substituted and one of the groups is methoxy. In yet another aspect, the phenyl is di-substituted, one of the groups is methoxy and the other group is $C_1$-$C_2$ alkoxy substituted with pyridyl, thiazolyl, or methyl thiazol-5-yl. In one aspect, the other group is $C_1$ alkoxy substituted with pyridyl, or methyl thiazol-5-yl. In yet another aspect, the other group is $C_2$ alkoxy substituted with pyridyl, or methyl thiazol-5-yl.

Embodiment 13G. Compounds according to Embodiment 13, wherein
$R_2$ is $C_3$-$C_5$ alkyl substituted with phenyl, wherein the phenyl is optionally substituted with 1, 2, or 3 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$—R$_{25}$, —($C_1$-$C_4$ alkyl)-S(O)$_x$—R$_{25}$, or OH; wherein
x is 0, 1, or 2;
$R_{25}$ is $C_1$-$C_6$ alkyl, OH, NR$_{26}$R$_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 13G1. Compounds according to Embodiment 13G, wherein
$R_2$ is $C_3$-$C_5$ alkyl substituted with phenyl, wherein the phenyl is substituted with 1 or 2 groups that are independently —S(O)$_x$—R$_{25}$, —($C_1$-$C_4$ alkyl)-S(O)$_x$—R$_{25}$, or OH; wherein
x is 0, 1, or 2;
$R_{25}$ is $C_1$-$C_6$ alkyl, OH, NR$_{26}$R$_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 13G2. Compounds according to Embodiment 13G, wherein
$R_2$ is $C_3$-$C_5$ alkyl substituted with phenyl, wherein the phenyl is substituted with 1 or 2 groups that are independently —S(O)$_x$—R$_{25}$, or —($C_1$-$C_4$ alkyl)-S(O)$_x$—R$_{25}$; wherein
x is 0, or 2; and
$R_{25}$ is $C_1$-$C_6$ alkyl, or OH.

Embodiment 13G3. Compounds according to Embodiment 13G, wherein
$R_2$ is $C_3$-$C_5$ alkyl substituted with phenyl, wherein the phenyl is substituted with NR$_{26}$R$_{27}$; wherein
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 13G4. Compounds according to Embodiment 13G, wherein
$R_2$ is $C_3$-$C_5$ alkyl substituted with phenyl, wherein the phenyl is substituted with NR$_{26}$R$_{27}$; wherein
$R_{26}$ and $R_{27}$ are independently H, $C_1$-$C_6$ alkyl, phenyl ($C_1$-$C_4$ alkyl), phenyl, or pyridyl.

Embodiment 13G5. Compounds according to Embodiment 13G, wherein $R_2$ is $C_3$-$C_5$ alkyl substituted with phenyl, wherein the phenyl is substituted with NR$_{26}$R$_{27}$; wherein
$R_{26}$, $R_{27}$ and the nitrogen to which they are attached represent pyrrolidinyl, piperidinyl, piperazinyl, morpholinyl, or imidazolidinyl.

Embodiment 13H. Compounds according to Embodiment 13G, wherein $R_2$ is $C_3$-$C_4$ alkyl substituted with phenyl, wherein the phenyl is optionally substituted with 1, 2, or 3 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, or OH.

Embodiment 13I. Compounds according to Embodiment 13H, wherein $R_2$ is $C_3$-$C_4$ alkyl substituted with phenyl, wherein the phenyl is unsubstituted. In one aspect, the $C_3$ alkyl group is a straight chained alkyl group. In another aspect, the $C_4$ alkyl group is a straight chained $C_3$ alkyl group substituted with a methyl group.

Embodiment 13J. Compounds according to embodiment 13H, wherein $R_2$ is $C_3$-$C_4$ alkyl substituted with phenyl, wherein the phenyl is substituted with 1, or 2 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$) alkyl($C_1$-$C_4$) alkyl, $C_1$-$C_3$ alkoxy optionally substituted with pyridyl, thiazolyl, or methyl thiazol-5-yl, $C_1$-$C_4$ alkyl, or OH.

Embodiment 13K. Compounds according to embodiment 13J, wherein $R_2$ is $C_3$-$C_4$ alkyl substituted with phenyl, wherein the phenyl is substituted with 1 or 2 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$) alkyl($C_1$-$C_4$) alkyl, $C_1$-$C_2$ alkoxy, $C_1$-$C_4$ alkyl, or OH.

Embodiment 13L. Compounds according to embodiment 13J, wherein $R_2$ is $C_3$-$C_4$ alkyl substituted with phenyl, wherein the phenyl is substituted with 2 methoxy groups.

Embodiment 13L1. Compounds according to Embodiment 13K, wherein $R_2$ is $C_3$-$C_4$ alkyl substituted with phenyl, wherein the phenyl is substituted with 1 or 2 groups that are independently $CO_2H$, $C_1$-$C_4$ alkoxycarbonyl, —C(O)NH$_2$, —C(O)NH($C_1$-$C_4$) alkyl, or —C(O)N($C_1$-$C_4$)alkyl($C_1$-$C_4$) alkyl. In another aspect, the $C_1$-$C_4$ alkoxycarbonyl is a methoxy carbonyl or ethoxycarbonyl. More preferably, it is ethoxycarbonyl.

Embodiment 13L2. Compounds according to Embodiment 13K, wherein $R_2$ is $C_3$-$C_4$ alkyl substituted with phenyl, wherein the phenyl is substituted with 1 or 2 groups that are independently $CO_2H$, —C(O)NH$_2$, —C(O)NH($C_1$-$C_4$) alkyl, or —C(O)N($C_1$-$C_4$)alkyl($C_1$-$C_4$)alkyl. In another aspect, the phenyl group is substituted with 1 group selected that is $CO_2H$, —C(O)NH$_2$, —C(O)NH($C_1$-$C_4$)alkyl, or —C(O)N ($C_1$-$C_4$)alkyl($C_1$-$C_4$)alkyl.

Embodiment 13L3. Compounds according to Embodiment 13K, wherein $R_2$ is $C_3$-$C_4$ alkyl substituted with phenyl, wherein the phenyl is substituted with 1 or 2 groups that are independently halogen, $CO_2H$, $C_1$-$C_4$ alkoxycarbonyl, or OH.

Embodiment 13L4. Compounds according to Embodiment 13K, wherein $R_2$ is $C_3$-$C_4$ alkyl substituted with phenyl, wherein the phenyl is substituted with 1 or 2 groups that are independently halogen, —C(O)NH$_2$, —C(O)NH($C_1$-$C_4$) alkyl, —C(O)N($C_1$-$C_4$)alkyl($C_1$-$C_4$) alkyl, or OH.

Embodiment 13M. Compounds according to embodiment 13J, wherein $R_2$ is $C_3$-$C_4$ alkyl substituted with phenyl, wherein the phenyl is substituted with 1, or 2 groups that are independently halogen, methoxy, or $C_1$-$C_2$ alkoxy optionally substituted with pyridyl, thiazolyl, methyl thiazol-5-yl. In another aspect, the phenyl is di-substituted and one of the groups is methoxy. In yet another aspect, the phenyl is di-substituted, one of the groups is methoxy and the other group is $C_1$-$C_2$ alkoxy substituted with pyridyl, thiazolyl, methyl thiazol-5-yl. In one aspect, the other group is $C_1$ alkoxy substituted with pyridyl, or methyl thiazol-5-yl. In yet another aspect, the other group is $C_2$ alkoxy substituted with pyridyl, or methyl thiazol-5-yl.

Embodiment 13N. Compounds according to embodiment 12, wherein $R_2$ is $C_1$-$C_6$ alkyl substituted with benzofuranyl, 1,4-benzodioxanyl, or 1,3-benzodioxolyl. In another aspect, the alkyl group is $C_1$-$C_4$ alkyl. In still another aspect, the alkyl group is $C_2$-$C_5$ alkyl. In yet still another aspect, the alkyl group is $C_3$-$C_5$ alkyl.

Embodiment 13O. Compounds according to any one of embodiments 13A, 13B, 13C, 13D, 13E, 13E1, 13E2, 13E3, 13E4, 13E5, 13E6, 13E7, 13E8, 13E9, 13F, 13G, 13H, 13H1, 13H2, 13H3, 13H4, 13H5, 13I, 13J, 13K, 13L, 13L1, 13L2, 13L3, 13L4, 13M, or 13N wherein
$R_3$ is H, or halogen;
$R_4$ is halogen, methyl, $CF_3$, or methoxy; and
$R_{3'}$ is H, or halogen.

Embodiment 13P. Compounds according to embodiment 13O, wherein $R_3$ is H; $R_4$ is halogen (preferably F or Cl, more preferably Cl), methyl, or $CF_3$; and $R_{3'}$ is H. In another aspect, $R_4$ is methyl. In still another aspect, $R_4$ is $CF_3$. In yet another aspect, $R_4$ is Cl.

In embodiment 14, the invention provides compounds according to embodiment 6, wherein
$R_2$ is $C_3$-$C_8$ alkenyl, optionally substituted with 1 or 2 groups that are independently phenyl, halogen, 2H-chromenyl, 1,2,3,4-tetrahydronaphthalenyl, indolyl, 3,4-dihydronaphthalenyl, naphthyl, $C_3$-$C_8$ cycloalkyl, benzofuranyl, indolyl, 1,4-benzodioxanyl, 1,3-benzodioxolyl, pyridyl, $C_1$-$C_4$ alkyl, halogen, —$CO_2$—($C_1$-$C_4$ alkyl), pyrazolyl, imidazolyl, oxazolyl, isoxazolyl, oxadiazolyl, thiazolyl, thiadiazolyl, triazolyl, or pyrimidyl;
wherein the cyclic portions of each of the above are optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 14A. Compounds according to embodiment 14, wherein $R_2$ is $C_3$-$C_8$ alkenyl, which is optionally substituted with 2H-chromenyl, 1,2,3,4-tetrahydronaphthalenyl, indolyl, 3,4-dihydronaphthalenyl, naphthyl, $C_3$-$C_8$ cycloalkyl, benzofuranyl, indolyl, 1,4-benzodioxanyl, 1,3-benzodioxolyl, pyridyl, triazolyl, or pyrimidyl; wherein the cyclic portions of each of the above are optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

In another aspect, $R_2$ is $C_3$-$C_6$ alkenyl, which is optionally substituted as above. In yet another aspect, $R_2$ is $C_3$-$C_5$ alkenyl, which is optionally substituted as above. In another aspect, $R_2$ is $C_4$-$C_7$ alkenyl, which is optionally substituted as above.

Embodiment 14B. Compounds according to embodiment 14, wherein $R_2$ is $C_3$-$C_8$ alkenyl, which is substituted with 1 or 2 groups which are independently $C_1$-$C_4$ alkyl, halogen, —$CO_2$—($C_1$-$C_4$ alkyl), pyrazolyl, imidazolyl, oxazolyl, isoxazolyl, oxadiazolyl, thiazolyl, thiadiazolyl, pyridyl, triazolyl, or pyrimidyl; wherein the cyclic portions of each of the above are optionally substituted with 1, or 2 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$) alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

In another aspect, $R_2$ is $C_3$-$C_6$ alkenyl, which is optionally substituted as above. In yet another aspect, $R_2$ is $C_3$-$C_5$ alkenyl, which is optionally substituted as above. In another aspect, the $C_3$-$C_5$ alkenyl is substituted with a halogen (preferably Cl or Br.) In still another aspect, $R_2$ is $C_4$-$C_7$ alkenyl, which is optionally substituted as above. In another aspect, the $C_4$-$C_7$ alkenyl is substituted with a halogen (preferably Cl or Br.)

Embodiment 14C. Compounds according to embodiment 14, wherein $R_2$ is $C_3$-$C_6$ alkenyl, which is substituted with 2 H-chromenyl, 1,2,3,4-tetrahydronaphthalenyl, 3,4-dihydronaphthalenyl, naphthyl, or $C_3$-$C_8$ cycloalkyl, wherein the cyclic portions of each of the above are optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 14D. Compounds according to embodiment 14, wherein $R_2$ is $C_3$-$C_4$ alkenyl, which is substituted with 2 H-chromenyl, 1,2,3,4-tetrahydronaphthalenyl, 3,4-dihydronaphthalenyl, naphthyl, or $C_3$-$C_8$ cycloalkyl.

Embodiment 14E. Compounds according to embodiment 14, wherein $R_2$ is $C_3$-$C_4$ alkenyl, which substituted with 1,2,3,4-tetrahydronaphthalenyl, 3,4-dihydronaphthalenyl, or naphthyl.

Embodiment 14F. Compounds according to embodiment 14, wherein $R_2$ is $C_3$-$C_6$ alkenyl, substituted with $C_3$-$C_8$ cycloalkyl. In another aspect, the $C_3$-$C_8$ cycloalkyl group is substituted with one or two methyl groups. In still another aspect, the $C_3$-$C_8$ cycloalkyl group is substituted with only —$CH_2$—OH. In yet still another aspect, the $C_3$-$C_8$ cycloalkyl group is substituted with one methyl group and one —$CH_2$—OH.

Embodiment 14G. Compounds according to embodiment 14, wherein $R_2$ is $C_3$-$C_6$ alkenyl, substituted with $C_3$-$C_6$ cycloalkyl. In another aspect, the $C_3$-$C_6$ cycloalkyl group is substituted with one or two methyl groups. In still another aspect, the $C_3$-$C_6$ cycloalkyl group is substituted with only —CH$_2$—OH. In yet still another aspect, the C$_3$-C$_6$ cycloalkyl group is substituted with one methyl group and one —CH$_2$—OH.

Embodiment 14H. Compounds according to embodiment 14, wherein R$_2$ is C$_3$-C$_4$ alkenyl, substituted with C$_5$-C$_6$ cycloalkyl. In another aspect, the C$_5$-C$_6$ cycloalkyl group is substituted with one or two methyl groups. In still another aspect, the C$_5$-C$_6$ cycloalkyl group is substituted with only —CH$_2$—OH. In yet still another aspect, the C$_5$-C$_6$ cycloalkyl group is substituted with one methyl group and one —CH$_2$—OH. In one aspect, the methyl group and the —CH$_2$—OH group are in a 1, 2 relationship relative to each other. In another aspect, the methyl group and the —CH$_2$—OH group are in a 1, 3 relationship relative to each other.

Embodiment 14I. Compounds according to embodiment 14, wherein R$_2$ is C$_3$-C$_4$ alkenyl, substituted with C$_6$ cycloalkyl. In another aspect, the C$_6$ cycloalkyl group is substituted with one or two methyl groups. In still another aspect, the C$_6$ cycloalkyl group is substituted with only —CH$_2$—OH. In yet still another aspect, the C$_6$ cycloalkyl group is substituted with one methyl group and one —CH$_2$—OH. In one aspect, the methyl group and the —CH$_2$—OH group are in a 1, 2 relationship relative to each other. In another aspect, the methyl group and the —CH$_2$—OH group are in a 1, 3 relationship relative to each other.

Embodiment 14J. Compounds according to embodiment 14, wherein R$_2$ is C$_3$-C$_6$ alkenyl, substituted with 2H-chromenyl, indolyl, benzofuranyl, 1,4-benzodioxanyl, 1,3-benzodioxolyl, pyridyl, triazolyl, or pyrimidyl; wherein the cyclic portions of each of the above are optionally substituted with 1, 2, or 3 groups that are independently halogen, CO$_2$H, C$_1$-C$_4$ alkoxycarbonyl, —C(O)NH$_2$, —C(O)NH(C$_1$-C$_4$) alkyl, —C(O)N(C$_1$-C$_4$)alkyl(C$_1$-C$_4$) alkyl, C$_1$-C$_4$ alkoxy optionally substituted with pyridyl, thiazolyl, or methyl thiazol-5-yl, C$_1$-C$_4$ alkyl, —S(O)$_x$—R$_{25}$, —(C$_1$-C$_4$ alkyl)-S(O)$_x$—R$_{25}$, or OH; wherein x is 0, 1, or 2;

R$_{25}$ is C$_1$-C$_6$ alkyl, OH, NR$_{26}$R$_{27}$;

R$_{26}$ and R$_{27}$ are independently H, C$_1$-C$_6$ alkyl, phenyl(C$_1$-C$_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

In another aspect, the cyclic portion of R$_2$ is not substituted.

Embodiment 14K. Compounds according to embodiment 14, wherein R$_2$ is C$_3$-C$_6$ alkenyl, substituted with 2H-chromenyl, indolyl, benzofuranyl, 1,4-benzodioxanyl, or 1,3-benzodioxolyl; wherein the cyclic portions of each of the above are optionally substituted with 1, 2, or 3 groups that are independently halogen, CO$_2$H, C$_1$-C$_4$ alkoxycarbonyl, —C(O)NH$_2$, —C(O)NH(C$_1$-C$_4$) alkyl, —C(O)N(C$_1$-C$_4$)alkyl(C$_1$-C$_4$) alkyl, C$_1$-C$_4$ alkoxy optionally substituted with pyridyl, thiazolyl, or methyl thiazol-5-yl, C$_1$-C$_4$ alkyl, —S(O)$_x$—R$_{25}$, —(C$_1$-C$_4$ alkyl)-S(O)$_x$—R$_{25}$, or OH; wherein x is 0, 1, or 2;

R$_{25}$ is C$_1$-C$_6$ alkyl, OH, NR$_{26}$R$_{27}$;

R$_{26}$ and R$_{27}$ are independently H, C$_1$-C$_6$ alkyl, phenyl(C$_1$-C$_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl.

In another aspect, the cyclic portion of R$_2$ is not substituted.

Embodiment 14L. Compounds according to embodiment 14, wherein R$_2$ is C$_3$-C$_6$ alkenyl, substituted with pyridyl, or pyrimidyl; wherein the cyclic portions of each of the above are optionally substituted with 1, 2, or 3 groups that are independently halogen, CO$_2$H, C$_1$-C$_4$ alkoxycarbonyl, —C(O)NH$_2$, —C(O)NH(C$_1$-C$_4$) alkyl, —C(O)N(C$_1$-C$_4$) alkyl(C$_1$-C$_4$) alkyl, C$_1$-C$_4$ alkoxy optionally substituted with pyridyl, thiazolyl, or methyl thiazol-5-yl, C$_1$-C$_4$ alkyl, —S(O)$_x$—R$_{25}$, —(C$_1$-C$_4$ alkyl)-S(O)$_x$—R$_{25}$, or OH; wherein x is 0, 1, or 2; R$_{25}$ is C$_1$-C$_6$ alkyl, OH, NR$_{26}$R$_{27}$;

R$_{26}$ and R$_{27}$ are independently H, C$_1$-C$_6$ alkyl, phenyl(C$_1$-C$_4$ alkyl), phenyl, or pyridyl; or R$_{26}$, R$_{27}$ and the nitrogen to which they are attached represent pyrrolidinyl, piperidinyl, piperazinyl, morpholinyl, or imidazolidinyl. In another aspect, the cyclic portion of R$_2$ is not substituted. In still another aspect, the pyridyl group is pyrid-2-yl, pyrid-3-yl, which is optionally substituted with one group that is methyl, methoxy, or halogen.

Embodiment 14M. Compounds according to embodiment 14, wherein

R$_2$ is C$_3$-C$_8$ alkenyl. In another aspect, R$_2$ is C$_3$-C$_6$ alkenyl. In still another aspect, R$_2$ is C$_3$-C$_5$ alkenyl. In yet still another aspect, R$_2$ is C$_4$-C$_6$ alkenyl.

Embodiment 14N. Compounds according to embodiment 14, wherein R$_2$ is C$_3$-C$_6$ alkenyl, substituted with benzofuranyl, 1,4-benzodioxanyl, or 1,3-benzodioxolyl.

Embodiment 14N1. Compounds according to Embodiment 14N, wherein R$_2$ is C$_3$-C$_6$ alkenyl, substituted with 1,4-benzodioxanyl, or 1,3-benzodioxolyl.

Embodiment 14N2. Compounds according to Embodiment 14, wherein R$_2$ is C$_3$-C$_6$ alkenyl, substituted with halogen or —CO$_2$—(C$_1$-C$_3$ alkyl).

Embodiment 14N3. Compounds according to embodiment 14, wherein R$_2$ is C$_3$-C$_6$ alkenyl, substituted with at least one triazolyl, which is optionally substituted as described in embodiment 14. In another aspect, the triazolyl group is unsubstituted. In still another aspect, the triazolyl group is substituted with only one group.

Embodiment 14O. Compounds according to embodiments 14 14A, 14B, 14C, 14D, 14E, 14F, 14, G, 14H, 14I, 14J, 14K, 14L, 14M, 14N, 14N1, 14N2, or 14N3, wherein R$_1$ is C$_1$-C$_8$ alkyl. In another aspect, R$_1$ is C$_2$-C$_8$ alkyl. In still another aspect, R$_1$ is C$_3$-C$_6$ alkyl. In yet still another aspect, R$_1$ is C$_3$-C$_5$ alkyl. In another aspect, R$_1$ is C$_6$-C$_8$ alkyl. In still another aspect, C$_7$-C$_8$ alkyl.

Embodiment 14P. Compounds according to embodiments 14 14A, 14B, 14C, 14D, 14E, 14F, 14, G, 14H, 14I, 14J, 14K, 14L, 14M, or 14N wherein R$_1$ is C$_1$-C$_8$ hydroxyalkyl. In another aspect, R$_1$ is C$_2$-C$_6$ hydroxyalkyl. In still another aspect, R$_1$ is C$_3$-C$_6$ hydroxyalkyl. In yet still another aspect, R$_1$ is C$_4$-C$_6$ hydroxyalkyl. In yet still another aspect, R$_1$ is C$_5$-C$_6$ hydroxyalkyl. In another aspect, R$_1$ is C$_7$-C$_8$ hydroxyalkyl.

Embodiment 14Q. Compounds according to Embodiment 14N, wherein

R$_1$ is

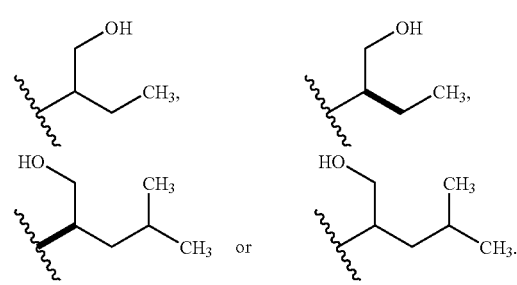

Embodiment 14R. Compounds according to Embodiment 14O, Embodiment 14P, or Embodiment 14Q wherein $R_3$ is H, or halogen;

$R_4$ is halogen, methyl, $CF_3$, or methoxy; and $R_{3'}$ is H, or halogen.

Embodiment 14S. Compounds according to Embodiment 14O Embodiment 14P, or Embodiment 14Q wherein $R_3$ is H; $R_4$ is halogen (preferably F or Cl, more preferably Cl), methyl or $CF_3$; and $R_{3'}$ is H. In another aspect, $R_4$ is methyl. In still another aspect, $R_4$ is $CF_3$. In yet another aspect, $R_4$ is Cl.

In embodiment 15, the invention provides compounds according to embodiment 14, wherein $R_2$ is $C_3$-$C_6$ alkenyl, optionally substituted with 1 or 2 groups that are phenyl, halogen, pyrazolyl, imidazolyl, oxazolyl, isoxazolyl, oxadiazolyl, thiazolyl, thiadiazolyl, triazolyl, or pyrimidyl; wherein the phenyl group is optionally substituted with 1, 2, or 3 groups that are independently halogen, $CO_2H$, $C_1$-$C_4$ alkoxycarbonyl, —$C(O)NH_2$, —$C(O)NH(C_1$-$C_4)$ alkyl, —$C(O)N(C_1$-$C_4)$alkyl$(C_1$-$C_4)$ alkyl, $C_1$-$C_4$ alkoxy optionally substituted with pyridyl, thiazolyl, or methyl thiazol-5-yl, $C_1$-$C_4$ alkyl, —$S(O)_x$—$R_{25}$, —$(C_1$-$C_4$ alkyl)-$S(O)_x$—$R_{25}$, or OH; wherein x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl$(C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 15A. Compounds according to embodiment 15, wherein $R_2$ is $C_3$-$C_6$ alkenyl substituted with phenyl; wherein the phenyl group is optionally substituted with 1, 2, or 3 groups that are independently halogen (in one aspect, F or Cl), $CO_2H$, $C_1$-$C_4$ alkoxycarbonyl, —$C(O)NH_2$, —$C(O)NH(C_1$-$C_4)$ alkyl, —$C(O)N(C_1$-$C_4)$alkyl$(C_1$-$C_4)$ alkyl, $C_1$-$C_4$ alkoxy, $C_1$-$C_4$ alkyl, or OH.

Embodiment 15B. Compounds according to embodiment 15, wherein $R_2$ is $C_3$-$C_6$ alkenyl.

Embodiment 15C. Compounds according to embodiment 15, wherein $R_2$ is $C_3$-$C_5$ alkenyl substituted with phenyl; wherein the phenyl group is optionally substituted with 1 or 2 groups that are independently halogen (in one aspect, F or Cl), $CO_2H$, $C_1$-$C_4$ alkoxycarbonyl, —$C(O)NH_2$, —$C(O)NH(C_1$-$C_4)$ alkyl, —$C(O)N(C_1$-$C_4)$alkyl$(C_1$-$C_4)$ alkyl, $C_1$-$C_4$ alkoxy, or $C_1$-$C_4$ alkoxy substituted with pyridyl, thiazolyl, methyl thiazol-5-yl, —$S(O)_x$—$R_{25}$, or —$(C_1$-$C_4$ alkyl)-$S(O)_x$—$R_{25}$; wherein x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl$(C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 15D. Compounds according to embodiment 15, wherein $R_2$ is $C_3$-$C_5$ alkenyl substituted with phenyl; wherein the phenyl group is substituted with 2 methoxy groups. In one aspect, the methoxy groups are in a 1, 2 relationship relative to each other. In another aspect, the methoxy groups are in a 1, 3 relationship relative to each other.

Embodiment 15D1. Compounds according to Embodiment 15C, wherein $R_2$ is $C_3$-$C_5$ alkenyl substituted with phenyl, wherein the phenyl is substituted with 1 or 2 groups that are independently $CO_2H$, $C_1$-$C_4$ alkoxycarbonyl, —$C(O)NH_2$, —$C(O)NH(C_1$-$C_4)$ alkyl, or —$C(O)N(C_1$-$C_4)$alkyl$(C_1$-$C_4)$alkyl. In another aspect, the $C_1$-$C_4$ alkoxycarbonyl is a methoxy carbonyl or ethoxycarbonyl. More preferably, it is ethoxycarbonyl.

Embodiment 15D2. Compounds according to Embodiment 15C, wherein $R_2$ is $C_3$-$C_5$ alkenyl substituted with phenyl, wherein the phenyl is substituted with 1 or 2 groups that are independently $CO_2H$, —$C(O)NH_2$, —$C(O)NH(C_1$-$C_4)$ alkyl, or —$C(O)N(C_1$-$C_4)$alkyl$(C_1$-$C_4)$alkyl. In another aspect, the phenyl group is substituted with 1 group selected that is $CO_2H$, —$C(O)NH_2$, —$C(O)NH(C_1$-$C_4)$alkyl, or —$C(O)N(C_1$-$C_4)$alkyl$(C_1$-$C_4)$alkyl.

Embodiment 15D3. Compounds according to embodiment 15C, wherein $R_2$ is $C_3$-$C_5$ alkenyl substituted with phenyl, wherein the phenyl is substituted with 1 or 2 groups that are independently halogen (in one aspect, F, Cl, or Br in another aspect, Br or F), $CO_2H$, $C_1$-$C_4$ alkoxycarbonyl, or OH. In one aspect, the halogen is meta relative to the point of attachment of the alkenyl group to the phenyl group. In another aspect, the halogen is ortho relative to the point of attachment of the alkenyl group to the phenyl group.

Embodiment 15D4. Compounds according to embodiment 15C, wherein $R_2$ is $C_3$-$C_5$ alkenyl substituted with phenyl, wherein the phenyl is substituted with 1 or 2 groups that are independently halogen (in one aspect, F, Cl, or Br in another aspect, Br or F), —$C(O)NH_2$, —$C(O)NH(C_1$-$C_4)$alkyl, —$C(O)N(C_1$-$C_4)$alkyl$(C_1$-$C_4)$ alkyl, or OH. In one aspect, the halogen is meta relative to the point of attachment of the alkenyl group to the phenyl group. In another aspect, the halogen is ortho relative to the point of attachment of the alkenyl group to the phenyl group.

Embodiment 15D5. Compounds according to embodiment 15C, wherein $R_2$ is $C_3$-$C_5$ alkenyl substituted with phenyl, wherein the phenyl is substituted with 1 or 2 groups that are independently —$S(O)_x$—$R_{25}$, —$(C_1$-$C_4$ alkyl)-$S(O)_x$—$R_{25}$, or OH; wherein x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl$(C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 15D6. Compounds according to embodiment 15C, wherein $R_2$ is $C_3$-$C_5$ alkenyl substituted with phenyl, wherein the phenyl is substituted with 1 or 2 groups that are independently —$S(O)_x$—$R_{25}$, —$(C_1$-$C_4$ alkyl)-$S(O)_x$—$R_{25}$, or OH; wherein x is 0, 1, or 2;

$R_{25}$ is $C_1$-$C_6$ alkyl, or OH.

Embodiment 15D7. Compounds according to embodiment 15C, wherein $R_2$ is $C_3$-$C_5$ alkenyl substituted with phenyl, wherein the phenyl is substituted with 1 group that is $NR_{26}R_{27}$; wherein $R_{26}$ and $R_{27}$ are independently H, $C_1$-$C_6$ alkyl, phenyl$(C_1$-$C_4$ alkyl), phenyl, or pyridyl.

Embodiment 15D8. Compounds according to embodiment 15C, wherein $R_2$ is $C_3$-$C_5$ alkenyl substituted with phenyl, wherein the phenyl is substituted with 1 group that is $NR_{26}R_{27}$; wherein $R_{26}$, $R_{27}$ and the nitrogen to which they are attached represent pyrrolidinyl, piperidinyl, piperazinyl, morpholinyl, or imidazolidinyl.

Embodiment 15E. Compounds according to embodiment 15, wherein $R_2$ is $C_3$-$C_5$ alkenyl substituted with phenyl; wherein the phenyl group is substituted with 1 methoxy group. In another aspect, the phenyl group is substituted with 1 methoxy group and $C_2$-$C_3$ alkoxy substituted with pyridyl, thiazolyl, methyl thiazol-5-yl.

Embodiment 15F. Compounds according to embodiment 15, wherein $R_2$ is $C_3$-$C_5$ alkenyl substituted with phenyl, which is unsubstituted.

Embodiment 15G. Compounds according to embodiment 15, wherein $R_2$ is $C_3$-$C_5$ alkenyl substituted with phenyl; wherein the phenyl group is substituted with 1 halogen and 1 methoxy group.

Embodiment 15G1. Compounds according to embodiment 15, wherein $R_2$ is $C_3$-$C_5$ alkenyl substituted with phenyl, wherein the phenyl is substituted with 1 or 2 groups that are independently halogen, $CO_2H$, or $C_1$-$C_4$ alkoxycarbonyl.

Embodiment 15H. Compounds according to embodiment 15, wherein
$R_2$ is

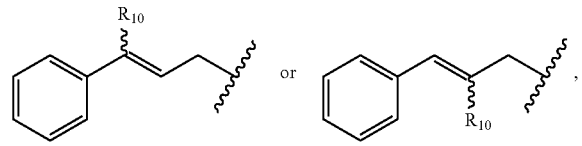

wherein
$R_{10}$ is $C_1$-$C_4$ alkyl (in one aspect, methyl), halogen (in one aspect, Cl or Br), phenyl, pyridyl, pyrazolyl, imidazolyl, oxazolyl, isoxazolyl, oxadiazolyl, thiazolyl, thiadiazolyl; and the phenyl group is unsubstituted or substituted as in any one of Embodiments 15A, 15C, 15D, 15D1, 15D2, 15D3, 15D4, 15D5, 15D6, 15D7, 15D8, 15E, or 15G. In one aspect, $R_{10}$ is methyl chloro or bromo. In another aspect, $R_{10}$ is phenyl or pyridyl. In still another aspect, $R_{10}$ is pyrazolyl, oxazolyl, isoxazolyl, oxadiazolyl, thiazolyl, or thiadiazolyl. In yet another aspect, $R_{10}$ is pyrazolyl or imidazolyl. In another aspect, $R_{10}$ is oxazolyl, isoxazolyl, or oxadiazolyl. In another aspect, $R_{10}$ is thiazolyl or thiadiazolyl.

Embodiment 15I. Compounds according to any one of embodiments 15, 15A, 15B, 15C, 15D, 15D1, 15D2, 15D3, 15D4, 15D5, 15D6, 15D7, 15D8, 15E, 15F, 15G, 15G1, or 15H wherein $R_1$ is $C_1$-$C_8$ hydroxyalkyl. In another aspect, $R_1$ is a $C_3$-$C_6$ hydroxyalkyl. In still another aspect, $R_1$ is a $C_5$-$C_6$ hydroxyalkyl. In another aspect, $R_1$ is $C_7$-$C_8$ hydroxyalkyl.

Embodiment 15J. Compounds according to Embodiment 15I,
wherein
$R_1$ is

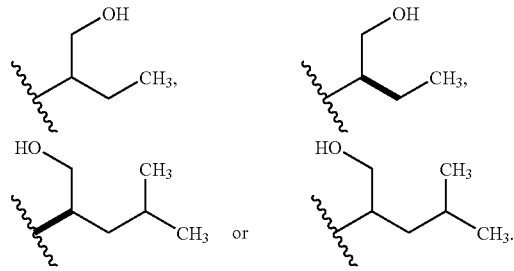

Embodiment 15K. Compounds according to any one of embodiments 15, 15A, 15B, 15C, 15D, 15E, 15F, 15G, 15G1, or 15H wherein $R_1$ is $C_1$-$C_8$ alkyl. In another aspect, $R_1$ is a $C_3$-$C_6$ alkyl. In still another aspect, $R_1$ is a $C_5$-$C_6$ alkyl. In another aspect, $R_1$ is $C_7$-$C_8$ alkyl.

Embodiment 15L. Compounds according to any one of embodiments 15, 15A, 15B, 15C, 15D, 15D1, 15D2, 15D3, 15D4, 15E, 15F, 15G, 15G1, 15H, 15I, 15J, or 15K, wherein
$R_3$ is H, halogen, $C_1$-$C_4$ alkyl, $C_1$-$C_4$ alkoxy, $CF_3$, CN;
$R_4$ is H, halogen, $C_1$-$C_4$ alkoxy, $CF_3$, $OCF_3$, CN, phenyloxy, —$SO_2$—($C_1$-$C_6$ alkyl), —NHR', —NR'R", $C_1$-$C_4$ alkanoyl, pyridyl, furanyl or thienyl, phenyl, or $C_1$-$C_4$ alkyl optionally substituted with —$CO_2$—($C_1$-$C_6$ alkyl);
$R_{3'}$ is H, or halogen;
R' is H, $C_1$-$C_4$ alkyl, benzyl, $C_1$-$C_6$ alkanoyl, phenyl($C_1$-$C_4$)alkanoyl, pyridyl($C_1$-$C_4$)alkyl, —$SO_2$-alkyl, —$SO_2$-phenyl, —$SO_2$-pyridyl, pyridyl($C_1$-$C_6$)alkanoyl, wherein the alkyl portion of the alkyl and alkanoyl groups are optionally substituted with halogen or $C_1$-$C_4$ alkoxy,
wherein the phenyl and pyridyl groups are optionally substituted with $C_1$-$C_4$ alkyl, $C_1$-$C_4$ alkoxy, halogen, $CF_3$, $OCF_3$;
R" is H or $C_1$-$C_6$ alkyl, wherein the alkyl group is optionally substituted with halogen.

Embodiment 15M. Compounds according to Embodiment 15L, wherein
$R_3$ is H., halogen, methyl, methoxy, $CF_3$, or CN;
$R_4$ is halogen, methyl, methoxy, $CF_3$, $OCF_3$, CN, —NHR', or —NR'R"; and
$R_{3'}$ is H, or halogen;
R' is H, or $C_1$-$C_4$ alkyl; and
R" is H or $C_1$-$C_6$ alkyl, wherein the alkyl group is optionally substituted with halogen.

Embodiment 15N. Compounds according to Embodiment 15M wherein $R_3$ is H, or halogen; $R_4$ is halogen, methyl, $CF_3$, or methoxy; and $R_{3'}$ is H, or halogen.

Embodiment 15O. Compounds according to Embodiment 15N wherein $R_3$ is H; $R_4$ is halogen (preferably F or Cl, more preferably Cl), methyl or $CF_3$; and $R_{3'}$ is H. In another aspect, $R_4$ is methyl. In still another aspect, $R_4$ is $CF_3$. In yet another aspect, $R_4$ is Cl.

In embodiment 16, the invention provides compounds according to Formula I, wherein
$R_1$ is $C_3$-$C_8$ cycloalkyl optionally substituted with 1 or 2 groups that are independently $C_1$-$C_4$ alkyl, $C_1$-$C_4$ hydroxyalkyl, or OH; or
$R_1$ is heterocycloalkyl or heterocycloalkyl($C_1$-$C_4$)alkyl wherein the heterocycloalkyl group is piperidinyl, pyrrolidinyl, tetrahydrofuranyl, pyrazolyl, or morpholinyl, wherein the heterocycloalkyl groups are optionally substituted with 1 or 2 groups that are independently $C_1$-$C_4$ alkyl, $C_1$-$C_4$ alkoxy, phenyl, phenyl($C_1$-$C_4$)alkyl, OH, halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or $C_1$-$C_4$ alkoxycarbonyl; or
$R_1$ is heteroaryl($C_1$-$C_4$)alkyl, wherein the heteroaryl group is pyridyl, pyrimidyl, furanyl, or thienyl and the heteroaryl group is optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkyl, $C_1$-$C_4$ alkoxy or OH.

Embodiment 16A. Compounds according to any one of embodiments 15H, 15I, 15J, 15K, 15L, 15M, 15N, 15O, or 16, wherein $R_{10}$ is methyl, chloro, or bromo.

In embodiment 17, the invention provides compounds according to embodiment 16, wherein $R_2$ is $C_1$-$C_8$ alkyl, or $C_2$-$C_8$ alkenyl, each of which is optionally substituted with 1 or 2 groups that are independently, 2H-chromenyl, 1,2,3,4-tetrahydronaphthalenyl, indolyl, 3,4-dihydronaphthalenyl, phenyl, naphthyl, $C_3$-$C_8$ cycloalkyl, benzofuranyl, indolyl, 1,4-benzodioxanyl, 1,3-benzodioxolyl, pyridyl, pyrimidyl, $C_1$-$C_4$ alkyl, halogen, pyrazolyl, imidazolyl, oxazolyl, isoxazolyl, oxadiazolyl, thiazolyl, thiadiazolyl, furanyl, triazolyl, or CN, wherein the cyclic portions of each of the above are optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_4$ alkoxy optionally substituted with pyridyl, thiazolyl, or methyl thiazol-5-yl, $NO_2$, $C_1$-$C_4$ alkyl, —S(O)$_x$—$R_{25}$, —($C_1$-$C_4$ alkyl)-S(O)$_x$—$R_{25}$, or OH; wherein x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl ($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 17A. Compounds according to embodiment 17, wherein $R_2$ is $C_1$-$C_2$ alkyl substituted with phenyl, wherein the phenyl is optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl ($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 17B. Compounds according to Embodiment 17A, wherein $R_2$ is $C_1$-$C_2$ alkyl substituted with phenyl, wherein the phenyl is unsubstituted.

Embodiment 17C. Compounds according to embodiment 17A, wherein $R_2$ is $C_1$-$C_2$ alkyl substituted with phenyl, wherein the phenyl is substituted with 1, or 2 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_3$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein x is 0, 1, or 2;

$R_{25}$ is $C_1$-$C_6$ alkyl, OH, $NR_{26}R_{27}$;

$R_{26}$ and R27 are independently H, $C_1$-$C_6$ alkyl, phenyl ($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 17C1. Compounds according to embodiment 17C, wherein $R_2$ is $C_1$-$C_2$ alkyl substituted with phenyl, wherein the phenyl is substituted with 1, or 2 groups that are independently —S(O)$_x$—$R_{25}$, —($C_1$-$C_4$ alkyl)-S(O)$_x$—$R_{25}$, or OH; wherein x is 0, 1, or 2;

$R_{25}$ is $C_1$-$C_6$ alkyl, OH, $NR_{26}R_{27}$;

R26 and $R_{27}$ are independently H, $C_1$-$C_6$ alkyl, phenyl ($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 17C2. Compounds according to embodiment 17C, wherein $R_2$ is $C_1$-$C_2$ alkyl substituted with phenyl, wherein the phenyl is substituted with 1, or 2 groups that are independently —S(O)$_x$—$R_{25}$, —($C_1$-$C_4$ alkyl)-S(O)$_x$—$R_{25}$, or OH; wherein x is 0, 1, or 2; $R_{25}$ is $C_1$-$C_6$ alkyl, or OH.

Embodiment 17C3. Compounds according to embodiment 17C, wherein $R_2$ is $C_1$-$C_2$ alkyl substituted with phenyl, wherein the phenyl is substituted with 1 group that is $NR_{26}R_{27}$; wherein $R_{26}$ and $R_{27}$ are independently H, $C_1$-$C_6$ alkyl, phenyl($C_1$-$C_4$ alkyl), phenyl, or pyridyl.

Embodiment 17C4. Compounds according to embodiment 17C, wherein $R_2$ is $C_1$-$C_2$ alkyl substituted with phenyl, wherein the phenyl is substituted with 1 group that is $NR_{26}R_{27}$; wherein $R_{26}$, $R_{27}$ and the nitrogen to which they are attached represent pyrrolidinyl, piperidinyl, piperazinyl, morpholinyl, or imidazolidinyl.

Embodiment 17D. Compounds according to embodiment 17C, wherein $R_2$ is $C_1$-$C_2$ alkyl substituted with phenyl, wherein the phenyl is substituted with 1, or 2 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_2$ alkoxy, $C_1$-$C_4$ alkyl, or OH.

Embodiment 17E. Compounds according to embodiment 17D, wherein $R_2$ is $C_1$-$C_2$ alkyl substituted with phenyl, wherein the phenyl is substituted with 2 methoxy groups.

Embodiment 17E1. Compounds according to Embodiment 17D, wherein $R_2$ is $C_1$-$C_2$ alkyl substituted with phenyl, wherein the phenyl is substituted with 1 or 2 groups that are independently $CO_2H$, $C_1$-$C_4$ alkoxycarbonyl, —C(O)$NH_2$, —C(O)NH($C_1$-$C_4$) alkyl, or —C(O)N($C_1$-$C_4$)alkyl($C_1$-$C_4$) alkyl. In another aspect, the $C_1$-$C_4$ alkoxycarbonyl is a methoxy carbonyl or ethoxycarbonyl. More preferably, it is ethoxycarbonyl.

Embodiment 17E2. Compounds according to Embodiment 17D, wherein $R_2$ is $C_1$-$C_2$ alkyl substituted with phenyl, wherein the phenyl is substituted with 1 or 2 groups that are independently $CO_2H$, —C(O)$NH_2$, —C(O)NH($C_1$-$C_4$)alkyl, or —C(O)N($C_1$-$C_4$)alkyl($C_1$-$C_4$)alkyl. In another aspect, the phenyl group is substituted with 1 group selected that is $CO_2H$, —C(O)$NH_2$, —C(O)NH($C_1$-$C_4$)alkyl, or —C(O)N($C_1$-$C_4$)alkyl($C_1$-$C_4$)alkyl.

Embodiment 17E3. Compounds according to embodiment 17D, wherein $R_2$ is $C_1$-$C_2$ alkyl substituted with phenyl, wherein the phenyl is substituted with 1 or 2 groups that are independently halogen, $CO_2H$, $C_1$-$C_4$ alkoxycarbonyl, or OH.

Embodiment 17E4. Compounds according to embodiment 17D, wherein $R_2$ is $C_1$-$C_2$ alkyl substituted with phenyl, wherein the phenyl is substituted with 1 or 2 groups that are independently halogen, —C(O)$NH_2$, —C(O)NH($C_1$-$C_4$) alkyl, —C(O)N($C_1$-$C_4$)alkyl($C_1$-$C_4$) alkyl, or OH.

Embodiment 17F. Compounds according to embodiment 17D, wherein $R_2$ is $C_1$-$C_2$ alkyl substituted with phenyl, wherein the phenyl is substituted with 1, or 2 groups that are independently halogen, methoxy, or $C_1$-$C_2$ alkoxy optionally substituted with pyridyl, thiazolyl, methyl thiazol-5-yl.

In another aspect, the phenyl is di-substituted and one of the groups is methoxy. In yet another aspect, the phenyl is di-substituted, one of the groups is methoxy and the other group is $C_1$-$C_2$ alkoxy substituted with pyridyl, thiazolyl, methyl thiazol-5-yl. In one aspect, the other group is $C_1$ alkoxy substituted with pyridyl, or methyl thiazol-5-yl. In yet another aspect, the other group is $C_2$ alkoxy substituted with pyridyl, or methyl thiazol-5-yl.

Embodiment 17G. Compounds according to Embodiment 17, wherein
- $R_2$ is $C_3$-$C_5$ alkyl substituted with phenyl, wherein the phenyl is optionally substituted with 1, 2, or 3 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
  x is 0, 1, or 2;
  $R_{25}$ is $C_1$-$C_6$ alkyl, OH, $NR_{26}R_{27}$;
  $R_{26}$ and $R_{27}$ are independently H, $C_1$-$C_6$ alkyl, phenyl($C_1$-$C_4$ alkyl), phenyl, or pyridyl; or
  $R_{26}$, $R_{27}$ and the nitrogen to which they are attached represent pyrrolidinyl, piperidinyl, piperazinyl, morpholinyl, or imidazolidinyl.

Embodiment 17H. Compounds according to Embodiment 17G, wherein
- $R_2$ is $C_3$-$C_4$ alkyl substituted with phenyl, wherein the phenyl is optionally substituted with 1, 2, or 3 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
  x is 0, 1, or 2;
  $R_{25}$ is $C_1$-$C_6$ alkyl, OH, $NR_{26}R_{27}$;
  $R_{26}$ and $R_{27}$ are independently H, $C_1$-$C_6$ alkyl, phenyl($C_1$-$C_4$ alkyl), phenyl, or pyridyl; or
  $R_{26}$, $R_{27}$ and the nitrogen to which they are attached represent pyrrolidinyl, piperidinyl, piperazinyl, morpholinyl, or imidazolidinyl.

Embodiment 17H1. Compounds according to embodiment 17H, wherein $R_2$ is $C_3$-$C_4$ alkyl substituted with phenyl, wherein the phenyl is substituted with 1, or 2 groups that are independently
—S(O)$_x$—$R_{25}$, —($C_1$-$C_4$ alkyl)-S(O)$_x$—$R_{25}$, or OH; wherein
  x is 0, 1, or 2;
  $R_{25}$ is $C_1$-$C_6$ alkyl, OH, $NR_{26}R_{27}$;
  $R_{26}$ and $R_{27}$ are independently H, $C_1$-$C_6$ alkyl, phenyl($C_1$-$C_4$ alkyl), phenyl, or pyridyl; or
  $R_{26}$, $R_{27}$ and the nitrogen to which they are attached represent pyrrolidinyl, piperidinyl, piperazinyl, morpholinyl, or imidazolidinyl.

Embodiment 17H2. Compounds according to embodiment 17H, wherein $R_2$ is $C_3$-$C_4$ alkyl substituted with phenyl, wherein the phenyl is substituted with 1, or 2 groups that are independently
—S(O)$_x$—$R_{25}$, —($C_1$-$C_4$ alkyl)-S(O)$_x$—$R_{25}$, or OH; wherein
  x is 0, 1, or 2;
  $R_{25}$ is $C_1$-$C_6$ alkyl, or OH.

Embodiment 17H3. Compounds according to embodiment 17H, wherein $R_2$ is $C_3$-$C_4$ alkyl substituted with phenyl, wherein the phenyl is substituted with 1 group that is $NR_{26}R_{27}$; wherein $R_{26}$ and $R_{27}$ are independently H, $C_1$-$C_6$ alkyl, phenyl($C_1$-$C_4$ alkyl), phenyl, or pyridyl.

Embodiment 17H4. Compounds according to embodiment 17H, wherein $R_2$ is $C_3$-$C_4$ alkyl substituted with phenyl, wherein the phenyl is substituted with 1 group that is $NR_{26}R_{27}$; wherein
  $R_{26}$, $R_{27}$ and the nitrogen to which they are attached represent pyrrolidinyl, piperidinyl, piperazinyl, morpholinyl, or imidazolidinyl.

Embodiment 17I. Compounds according to Embodiment 17H, wherein $R_2$ is $C_3$-$C_4$ alkyl substituted with phenyl, wherein the phenyl is unsubstituted. In one aspect, the $C_3$ alkyl group is a straight chained alkyl group. In another aspect, the $C_4$ alkyl group is a straight chained $C_3$ alkyl group substituted with a methyl group.

Embodiment 17J. Compounds according to embodiment 17H, wherein
- $R_2$ is $C_3$-$C_4$ alkyl substituted with phenyl, wherein the phenyl is substituted with 1, or 2 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_3$ alkoxy optionally substituted with pyridyl, thiazolyl, or methyl thiazol-5-yl, $C_1$-$C_4$ alkyl, or OH.

Embodiment 17K. Compounds according to embodiment 17J, wherein
- $R_2$ is $C_3$-$C_4$ alkyl substituted with phenyl, wherein the phenyl is substituted with 1, or 2 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_2$ alkoxy, $C_1$-$C_4$ alkyl, or OH.

Embodiment 17K1. Compounds according to Embodiment 17K, wherein $R_2$ is $C_3$-$C_4$ alkyl substituted with phenyl, wherein the phenyl is substituted with 1 or 2 groups that are independently $CO_2H$, $C_1$-$C_4$ alkoxycarbonyl, —C(O)NH$_2$, —C(O)NH($C_1$-$C_4$) alkyl, or —C(O)N($C_1$-$C_4$)alkyl($C_1$-$C_4$) alkyl. In another aspect, the $C_1$-$C_4$ alkoxycarbonyl is a methoxy carbonyl or ethoxycarbonyl. More preferably, it is ethoxycarbonyl.

Embodiment 17K2. Compounds according to Embodiment 17K, wherein $R_2$ is $C_3$-$C_4$ alkyl substituted with phenyl, wherein the phenyl is substituted with 1 or 2 groups that are independently $CO_2H$, —C(O)NH$_2$, —C(O)NH($C_1$-$C_4$) alkyl, or —C(O)N($C_1$-$C_4$)alkyl($C_1$-$C_4$)alkyl. In another aspect, the phenyl group is substituted with 1 group selected that is $CO_2H$, —C(O)NH$_2$, —C(O)NH($C_1$-$C_4$)alkyl, or —C(O)N($C_1$-$C_4$)alkyl($C_1$-$C_4$)alkyl.

Embodiment 17K3. Compounds according to embodiment 17K, wherein $R_2$ is $C_3$-$C_4$ alkyl substituted with phenyl, wherein the phenyl is substituted with 1 or 2 groups that are independently halogen, $CO_2H$, $C_1$-$C_4$ alkoxycarbonyl, or OH.

Embodiment 17K4. Compounds according to embodiment 17K, wherein $R_2$ is $C_3$-$C_4$ alkyl substituted with phenyl, wherein the phenyl is substituted with 1 or 2 groups that are independently halogen, —C(O)NH$_2$, —C(O)NH($C_1$-$C_4$) alkyl, —C(O)N($C_1$-$C_4$)alkyl($C_1$-$C_4$) alkyl, or OH.

Embodiment 17L. Compounds according to embodiment 17J, wherein
- $R_2$ is $C_3$-$C_4$ alkyl substituted with phenyl, wherein the phenyl is substituted with 2 methoxy groups.

Embodiment 17M. Compounds according to embodiment 17J, wherein $R_2$ is $C_3$-$C_4$ alkyl substituted with phenyl, wherein the phenyl is substituted with 1, or 2 groups that are independently halogen, $CO_2H$, $C_1$-$C_4$ alkoxycarbonyl, —C(O) NH$_2$, —C(O)NH($C_1$-$C_4$) alkyl, —C(O)N($C_1$-$C_4$)

alkyl($C_1$-$C_4$) alkyl, methoxy, or $C_1$-$C_2$ alkoxy optionally substituted with pyridyl, thiazolyl, methyl thiazol-5-yl. In another aspect, the phenyl is di-substituted and one of the groups is methoxy. In yet another aspect, the phenyl is di-substituted, one of the groups is methoxy and the other group is $C_1$-$C_2$ alkoxy substituted with pyridyl, thiazolyl, methyl thiazol-5-yl. In one aspect, the other group is $C_1$ alkoxy substituted with pyridyl, or methyl thiazol-5-yl. In yet another aspect, the other group is $C_2$ alkoxy substituted with pyridyl, or methyl thiazol-5-yl.

Embodiment 17N. Compounds according to embodiment 17, wherein $R_2$ is $C_1$-$C_6$ alkyl substituted with 1,4-benzodioxanyl, or 1,3-benzodioxolyl. In another aspect, the alkyl group is $C_1$-$C_4$ alkyl. In still another aspect, the alkyl group is $C_2$-$C_5$ alkyl. In yet still another aspect, the alkyl group is $C_3$-$C_5$ alkyl. In another aspect, $R_2$ is $C_3$-$C_8$ alkyl. In yet another aspect, $R_2$ is $C_5$-$C_8$ alkyl. In still another aspect, $R_2$ is $C_7$-$C_8$ alkyl. In still another aspect, $R_2$ is $C_5$-$C_7$ alkyl.

Embodiment 17O. Compounds according to embodiment 17, wherein $R_2$ is $C_3$-$C_8$ alkenyl, which is optionally substituted with 2H-chromenyl, 1,2,3,4-tetrahydronaphthalenyl, indolyl, 3,4-dihydronaphthalenyl, naphthyl, $C_3$-$C_8$ cycloalkyl, benzofuranyl, indolyl, 1,4-benzodioxanyl, 1,3-benzodioxolyl, pyridyl, or pyrimidyl; wherein the cyclic portions of each of the above are optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein x is 0, 1, or 2; $R_{25}$ is $C_1$-$C_6$ alkyl, OH, $NR_{26}R_{27}$; $R_{26}$ and $R_{27}$ are independently H, $C_1$-$C_6$ alkyl, phenyl($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 17P. Compounds according to embodiment 17, wherein $R_2$ is $C_3$-$C_8$ alkenyl, which is substituted with 2H-chromenyl, 1,2,3,4-tetrahydronaphthalenyl, indolyl, 3,4-dihydronaphthalenyl, naphthyl, $C_3$-$C_8$ cycloalkyl, benzofuranyl, indolyl, 1,4-benzodioxanyl, 1,3-benzodioxolyl, pyridyl, or pyrimidyl; wherein the cyclic portions of each of the above are optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$) alkyl($C_1$-$C_4$) alkyl, $C_1$-$C_4$ alkoxy optionally substituted with pyridyl, thiazolyl, or methyl thiazol-5-yl, $C_1$-$C_4$ alkyl, or OH.

Embodiment 17Q. Compounds according to embodiment 17, wherein $R_2$ is $C_3$-$C_6$ alkenyl, which is substituted with 2H-chromenyl, 1,2,3,4-tetrahydronaphthalenyl, 3,4-dihydronaphthalenyl, naphthyl, or $C_3$-$C_8$ cycloalkyl, wherein the cyclic portions of each of the above are optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$; $R_{26}$ and $R_{27}$ are independently H, $C_1$-$C_6$ alkyl, phenyl($C_1$-$C_4$ alkyl), phenyl, or pyridyl; or R26, $R_{27}$ and the nitrogen to which they are attached represent pyrrolidinyl, piperidinyl, piperazinyl, morpholinyl, or imidazolidinyl.

Embodiment 17Q1. Compounds according to embodiment 17Q, wherein $R_2$ is $C_3$-$C_5$ alkenyl which is substituted with 2 H-chromenyl, 1,2,3,4-tetrahydronaphthalenyl, 3,4-dihydronaphthalenyl, naphthyl, or $C_3$-$C_8$ cycloalkyl, wherein the cyclic portions of each of the above are optionally substituted with 1 or 2 groups that are independently
—S(O)$_x$—$R_{25}$, —($C_1$-$C_4$ alkyl)-S(O)$_x$—$R_{25}$, or OH;
wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 17Q2. Compounds according to embodiment 17Q, wherein $R_2$ is $C_3$-$C_5$ alkenyl which is substituted with 2 H-chromenyl, 1,2,3,4-tetrahydronaphthalenyl, 3,4-dihydronaphthalenyl, naphthyl, or $C_3$-$C_8$ cycloalkyl, wherein the cyclic portions of each of the above are optionally substituted with 1 or 2 groups that are independently
—S(O)$_x$—$R_{25}$, —($C_1$-$C_4$ alkyl)-S(O)$_x$—$R_{25}$, or OH;
wherein
x is 0, 1, or 2;
$R_{25}$ is $C_1$-$C_6$ alkyl, or OH.

Embodiment 17Q3. Compounds according to embodiment 17Q, wherein $R_2$ is $C_3$-$C_5$ alkenyl which is substituted with 2 H-chromenyl, 1,2,3,4-tetrahydronaphthalenyl, 3,4-dihydronaphthalenyl, naphthyl, or $C_3$-$C_8$ cycloalkyl, wherein the cyclic portions of each of the above are optionally substituted with 1 group that is $NR_{26}R_{27}$; wherein
$R_{26}$ and $R_{27}$ are independently H, $C_1$-$C_6$ alkyl, phenyl($C_1$-$C_4$ alkyl), phenyl, or pyridyl.

Embodiment 17Q4. Compounds according to embodiment 17Q, wherein $R_2$ is $C_3$-$C_5$ alkenyl which is substituted with 2 H-chromenyl, 1,2,3,4-tetrahydronaphthalenyl, 3,4-dihydronaphthalenyl, naphthyl, or $C_3$-$C_8$ cycloalkyl, wherein the cyclic portions of each of the above are optionally substituted with 1 group that is $NR_{26}R_{27}$; wherein $R_{26}$, $R_{27}$ and the nitrogen to which they are attached represent pyrrolidinyl, piperidinyl, piperazinyl, morpholinyl, or imidazolidinyl.

Embodiment 17R. Compounds according to embodiment 17, wherein $R_2$ is $C_3$-$C_4$ alkenyl, which is substituted with 2 H-chromenyl, 1,2,3,4-tetrahydronaphthalenyl, 3,4-dihydronaphthalenyl, naphthyl, or $C_3$-$C_8$ cycloalkyl.

Embodiment 17S. Compounds according to embodiment 17, wherein $R_2$ is $C_3$-$C_4$ alkenyl, which is substituted with 1,2,3,4-tetrahydronaphthalenyl, 3,4-dihydronaphthalenyl, or naphthyl.

Embodiment 17S1. Compounds according to embodiment 17, wherein $R_2$ is $C_3$-$C_5$ alkenyl, substituted with naphthyl, which is optionally substituted with two groups that are independently $C_1$-$C_4$ alkyl, $C_1$-$C_4$ alkoxy, or halogen. In another aspect, the naphthyl is unsubstituted.

Embodiment 17T. Compounds according to embodiment 17, wherein $R_2$ is $C_3$-$C_6$ alkenyl, substituted with $C_3$-$C_8$ cycloalkyl. In another aspect, the $C_3$-$C_8$ cycloalkyl group is substituted with one or two methyl groups. In still another aspect, the $C_3$-$C_8$ cycloalkyl group is substituted with only —$CH_2$—OH. In yet still another aspect, the $C_3$-$C_8$ cycloalkyl group is substituted with one methyl group and one —$CH_2$—OH.

Embodiment 17U. Compounds according to embodiment 17, wherein $R_2$ is $C_3$-$C_6$ alkenyl, substituted with $C_3$-$C_6$ cycloalkyl. In another aspect, the $C_3$-$C_6$ cycloalkyl group is substituted with one or two methyl groups. In still another aspect, the $C_3$-$C_6$ cycloalkyl group is substituted with only —$CH_2$—OH. In yet still another aspect, the $C_3$-$C_6$ cycloalkyl group is substituted with one methyl group and one —$CH_2$—OH.

Embodiment 17V. Compounds according to embodiment 17, wherein $R_2$ is $C_3$-$C_4$ alkenyl, substituted with $C_5$-$C_6$ cycloalkyl. In another aspect, the $C_5$-$C_6$ cycloalkyl group is substituted with one or two methyl groups. In still another aspect, the $C_5$-$C_6$ cycloalkyl group is substituted with only —$CH_2$—OH. In yet still another aspect, the $C_5$-$C_6$ cycloalkyl group is substituted with one methyl group and one —$CH_2$—OH. In one aspect, the methyl group and the —$CH_2$—OH group are in a 1, 2 relationship relative to each other. In another aspect, the methyl group and the —$CH_2$—OH group are in a 1, 3 relationship relative to each other.

Embodiment 17W. Compounds according to embodiment 17, wherein $R_2$ is $C_3$-$C_4$ alkenyl, substituted with $C_6$ cycloalkyl. In another aspect, the $C_6$ cycloalkyl group is substituted with one or two methyl groups. In still another aspect, the $C_6$ cycloalkyl group is substituted with only —$CH_2$—OH. In yet still another aspect, the $C_6$ cycloalkyl group is substituted with one methyl group and one —$CH_2$—OH. In one aspect, the methyl group and the —$CH_2$—OH group are in a 1, 2 relationship relative to each other. In another aspect, the methyl group and the —$CH_2$—OH group are in a 1, 3 relationship relative to each other.

Embodiment 17X. Compounds according to embodiment 17, wherein $R_2$ is $C_3$-$C_6$ alkenyl, substituted with 2H-chromenyl, indolyl, benzofuranyl, 1,4-benzodioxanyl, 1,3-benzodioxolyl, pyridyl, or pyrimidyl; wherein the cyclic portions of each of the above are optionally substituted with 1, 2, or 3 groups that are independently halogen, $CO_2H$, $C_1$-$C_4$ alkoxycarbonyl, —$C(O)NH_2$, —$C(O)NH(C_1$-$C_4)$ alkyl, —$C(O)N(C_1$-$C_4)$alkyl$(C_1$-$C_4)$ alkyl, $C_1$-$C_4$ alkoxy optionally substituted with pyridyl, thiazolyl, or methyl thiazol-5-yl, $C_1$-$C_4$ alkyl, —$S(O)_x$—$R_{25}$, —$(C_1$-$C_4$ alkyl)-$S(O)_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

In another aspect, the cyclic portion of $R_2$ is not substituted.

Embodiment 17Y. Compounds according to embodiment 17, wherein $R_2$ is $C_3$-$C_6$ alkenyl, substituted with 2H-chromenyl, indolyl, benzofuranyl, 1,4-benzodioxanyl, or 1,3-benzodioxolyl; wherein the cyclic portions of each of the above are optionally substituted with 1, 2, or 3 groups that are independently halogen, $CO_2H$, $C_1$-$C_4$ alkoxycarbonyl, —$C(O)NH_2$, —$C(O)NH(C_1$-$C_4)$ alkyl, —$C(O)N(C_1$-$C_4)$alkyl$(C_1$-$C_4)$ alkyl, $C_1$-$C_4$ alkoxy optionally substituted with pyridyl, thiazolyl, or methyl thiazol-5-yl, $C_1$-$C_4$ alkyl, —$S(O)_x$—$R_{25}$, —$(C_1$-$C_4$ alkyl)-$S(O)_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

In another aspect, the cyclic portion of $R_2$ is not substituted.

Embodiment 17Y1. Compounds according to embodiment 17Y, wherein $R_2$ is $C_3$-$C_5$ alkenyl which is substituted with 2 H-chromenyl, indolyl, benzofuranyl, 1,4-benzodioxanyl, or 1,3-benzodioxolyl; wherein the cyclic portions of each of the above are optionally substituted with 1 or 2 groups that are independently —$S(O)_x$—$R_{25}$, —$(C_1$-$C_4$ alkyl)-$S(O)_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

Embodiment 17Y2. Compounds according to embodiment 17Y, wherein $R_2$ is $C_3$-$C_5$ alkenyl which is substituted with 2 H-chromenyl, indolyl, benzofuranyl, 1,4-benzodioxanyl, or 1,3-benzodioxolyl; wherein the cyclic portions of each of the above are optionally substituted with 1 or 2 groups that are independently —$S(O)_x$—$R_{25}$, —$(C_1$-$C_4$ alkyl)-$S(O)_x$—$R_{25}$, or OH; wherein
x is 0, 1, or 2;
$R_{25}$ is $C_1$-$C_6$ alkyl, or OH.

Embodiment 17Y3. Compounds according to embodiment 17Y, wherein $R_2$ is $C_3$-$C_5$ alkenyl which is substituted with 2 H-chromenyl, indolyl, benzofuranyl, 1,4-benzodioxanyl, or 1,3-benzodioxolyl; wherein the cyclic portions of each of the above are optionally substituted with 1 group that is $NR_{26}R_{27}$; wherein
$R_{26}$ and $R_{27}$ are independently H, $C_1$-$C_6$ alkyl, phenyl($C_1$-$C_4$ alkyl), phenyl, or pyridyl.

Embodiment 17Y4. Compounds according to embodiment 17Y, wherein $R_2$ is $C_3$-$C_5$ alkenyl which is substituted with 2 H-chromenyl, indolyl, benzofuranyl, 1,4-benzodioxanyl, or 1,3-benzodioxolyl; wherein the cyclic portions of each of the above are optionally substituted with 1 group that is $NR_{26}R_{27}$; wherein
$R_{26}$, $R_{27}$ and the nitrogen to which they are attached represent pyrrolidinyl, piperidinyl, piperazinyl, morpholinyl, or imidazolidinyl.

Embodiment 17Z. Compounds according to embodiment 17, wherein $R_2$ is $C_3$-$C_6$ alkenyl, substituted with pyridyl, or pyrimidyl, wherein the cyclic portions of each of the above are optionally substituted with 1, 2, or 3 groups that are independently halogen, $CO_2H$, $C_1$-$C_4$ alkoxycarbonyl, —$C(O)NH_2$, —$C(O)NH(C_1$-$C_4)$ alkyl, —$C(O)N(C_1$-$C_4)$alkyl$(C_1$-$C_4)$ alkyl, $C_1$-$C_4$ alkoxy optionally substituted with pyridyl, thiazolyl, or methyl thiazol-5-yl, $C_1$-$C_4$ alkyl, —$S(O)_x$—$R_{25}$, —$(C_1$-$C_4$ alkyl)-$S(O)_x$—$R_{25}$, or OH; wherein x is 0, 1, or 2; $R_{25}$ is $C_1$-$C_6$ alkyl, OH, $NR_{26}R_{27}$; $R_{26}$ and $R_{27}$ are independently H, $C_1$-$C_6$ alkyl, phenyl($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl. In another aspect, the cyclic portion of $R_2$ is not substituted.

Embodiment 17Z1. Compounds according to embodiment 17Z, wherein $R_2$ is $C_3$-$C_5$ alkenyl which is substituted with pyridyl, or pyrimidyl, wherein the cyclic portions of each of the above are optionally substituted with 1 or 2 groups that are independently —$S(O)_x$—$R_{25}$, —$(C_1$-$C_4$ alkyl)-$S(O)_x$—$R_{25}$, or OH; wherein x is 0, 1, or 2; $R_{25}$ is $C_1$-$C_6$ alkyl, OH, $NR_{26}R_{27}$; $R_{26}$ and $R_{27}$ are independently H, $C_1$-$C_6$ alkyl, phenyl($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 17Z2. Compounds according to embodiment 17Z, wherein $R_2$ is $C_3$-$C_5$ alkenyl which is substituted with pyridyl, or pyrimidyl, wherein the cyclic portions of each of the above are optionally substituted with 1 or 2 groups that are independently —$S(O)_x$—$R_{25}$, —$(C_1$-$C_4$ alkyl)-$S(O)_x$—$R_{25}$, or OH; wherein x is 0, 1, or 2; $R_{25}$ is $C_1$-$C_6$ alkyl, or OH.

Embodiment 17Z3. Compounds according to embodiment 17Z, wherein $R_2$ is $C_3$-$C_5$ alkenyl which is substituted with pyridyl, or pyrimidyl, wherein the cyclic portions of each of the above are optionally substituted with 1 group that is $NR_{26}R_{27}$; wherein $R_{26}$ and $R_{27}$ are independently H, $C_1$-$C_6$ alkyl, phenyl($C_1$-$C_4$ alkyl), phenyl, or pyridyl.

Embodiment 17Z4. Compounds according to embodiment 17Z, wherein $R_2$ is $C_3$-$C_5$ alkenyl which is substituted with pyridyl, or pyrimidyl, wherein the cyclic portions of each of the above are optionally substituted with 1 group that is $NR_{26}R_{27}$; wherein $R_{26}$, $R_{27}$ and the nitrogen to which they are attached represent pyrrolidinyl, piperidinyl, piperazinyl, morpholinyl, or imidazolidinyl.

Embodiment 17Z5. Compounds according to embodiment 17Z, wherein $R_2$ is $C_3$-$C_5$ alkenyl which is substituted with pyridyl, or pyrimidyl, wherein the cyclic portions of each of the above are optionally substituted with one halogen.

Embodiment 17AA. Compounds according to embodiment 17, wherein $R_2$ is $C_3$-$C_8$ alkenyl. In another aspect, $R_2$ is $C_3$-$C_7$ alkenyl. In still another aspect, $R_2$ is $C_3$-$C_5$ alkenyl. In yet still another aspect, $R_2$ is $C_4$-$C_6$ alkenyl.

Embodiment 17BB. Compounds according to embodiment 17, wherein $R_2$ is $C_3$-$C_6$ alkenyl, substituted with 1,4-benzodioxanyl, or 1,3-benzodioxolyl.

Embodiment 17CC. Compounds according to embodiment 17, wherein $R_2$ is $C_3$-$C_6$ alkenyl substituted with phenyl; wherein the phenyl group is optionally substituted with 1, 2, or 3 groups that are independently halogen, $C_1$-$C_4$ alkoxy, $C_1$-$C_4$ alkyl, —S(O)$_x$—$R_{25}$, —($C_1$-$C_4$ alkyl)-S(O)$_x$—$R_{25}$, or OH; wherein x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

In another aspect, the cyclic portion of $R_2$ is not substituted.

Embodiment 17CC1. Compounds according to embodiment 17CC, wherein $R_2$ is $C_3$-$C_5$ alkenyl substituted with phenyl, wherein the cyclic portions of each of the above are optionally substituted with 1 or 2 groups that are independently —S(O)$_x$—$R_{25}$, —($C_1$-$C_4$ alkyl)-S(O)$_x$—$R_{25}$, or OH; wherein x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl ($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 17CC2. Compounds according to embodiment 17CC, wherein $R_2$ is $C_3$-$C_5$ alkenyl substituted with phenyl, wherein the cyclic portions of each of the above are optionally substituted with 1 or 2 groups that are independently —S(O)$_x$—$R_{25}$, —($C_1$-$C_4$ alkyl)-S(O)$_x$—$R_{25}$, or OH; wherein x is 0, 1, or 2;

$R_{25}$ is $C_1$-$C_6$ alkyl, or OH.

Embodiment 17CC3. Compounds according to embodiment 17CC, wherein $R_2$ is $C_3$-$C_5$ alkenyl substituted with phenyl, wherein the cyclic portions of each of the above are optionally substituted with 1 group that is $NR_{26}R_{27}$; wherein $R_{26}$ and $R_{27}$ are independently H, $C_1$-$C_6$ alkyl, phenyl($C_1$-$C_4$ alkyl), phenyl, or pyridyl.

Embodiment 17CC4. Compounds according to embodiment 17CC, wherein $R_2$ is $C_3$-$C_5$ alkenyl substituted with phenyl, wherein the cyclic portions of each of the above are optionally substituted with 1 group that is $NR_{26}R_{27}$; wherein $R_{26}$, $R_{27}$ and the nitrogen to which they are attached represent pyrrolidinyl, piperidinyl, piperazinyl, morpholinyl, or imidazolidinyl.

Embodiment 17DD. Compounds according to embodiment 17, wherein $R_2$ is $C_3$-$C_6$ alkenyl.

Embodiment 17EE. Compounds according to embodiment 17, wherein $R_2$ is $C_3$-$C_5$ alkenyl substituted with phenyl; wherein the phenyl group is optionally substituted with 1 or 2 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_4$ alkoxy substituted with pyridyl, thiazolyl, or methyl thiazol-5-yl.

Embodiment 17FF. Compounds according to embodiment 17, wherein $R_2$ is $C_3$-$C_5$ alkenyl substituted with phenyl; wherein the phenyl group is substituted with 2 methoxy groups. In one aspect, the methoxy groups are in a 1, 2 relationship relative to each other. In another aspect, the methoxy groups are in a 1, 3 relationship relative to each other.

Embodiment 17GG. Compounds according to embodiment 17, wherein $R_2$ is $C_3$-$C_5$ alkenyl substituted with phenyl; wherein the phenyl group is substituted with 1 methoxy group. In another aspect, the phenyl group is substituted with 1 methoxy group and $C_2$-$C_3$ alkoxy substituted with pyridyl, thiazolyl, or methyl thiazol-5-yl.

Embodiment 17HH. Compounds according to embodiment 17, wherein $R_2$ is $C_3$-$C_5$ alkenyl substituted with phenyl.

Embodiment 17II. Compounds according to embodiment 17, wherein $R_2$ is $C_3$-$C_5$ alkenyl substituted with phenyl; wherein the phenyl group is substituted with 1 halogen and 1 methoxy group.

Embodiment 17JJ. Compounds according to embodiment 17, wherein $R_2$ is

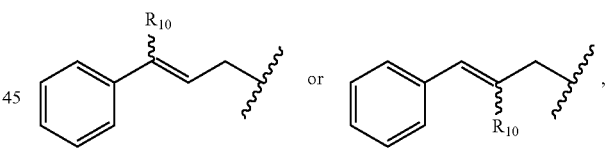

wherein $R_{10}$ is $C_1$-$C_4$ alkyl (in one aspect, methyl), halogen (in one aspect, Cl or Br), phenyl, pyridyl, pyrazolyl, imidazolyl, oxazolyl, isoxazolyl, oxadiazolyl, thiazolyl, thiadiazolyl; and the phenyl group is unsubstituted or substituted as in any one of Embodiments 17CC, 17CC1, 17CC2, 17CC3, 17CC4, 17EE, 17FF, 17GG, 17HH, or 17II. In one aspect, $R_{10}$ is methyl chloro or bromo. In another aspect, $R_{10}$ is phenyl or pyridyl. In still another aspect, $R_{10}$ is pyrazolyl, oxazolyl, isoxazolyl, oxadiazolyl, thiazolyl, or thiadiazolyl. In yet another aspect, $R_{10}$ is pyrazolyl or imidazolyl. In another aspect, $R_{10}$ is oxazolyl, isoxazolyl, or oxadiazolyl. In another aspect, $R_{10}$ is thiazolyl or thiadiazolyl.

Embodiment 17KK. Compounds according to any one of embodiments 15, 17A, 17B, 17C, 17C1, 17C2, 17C3, 17C4, 17D, 17E, 17E1, 17E2, 17E3, 17E4, 17F, 17G, 17H, 17H1, 17H2, 17H3, 17H4, 17I, 17J, 17K, 17L, 17M, 17N, 17O, 17P, 17Q, 17Q1, 17Q2, 17Q3, 17Q4, 17R, 17S, 17T, 17U, 17V, 17W, 17X, 17Y, 17Y1, 17Y2, 17Y3, 17Y4, 17Z, 17Z1, 17Z2, 17Z3, 17Z4, 17Z5, 17AA, 17BB, 17CC, 17CC1, 17CC2, 17CC3, 17CC4, 17DD, 17EE, 17FF, 17GG, 17HH, 17II, or 17JJ wherein
$R_3$ is H, halogen, $C_1$-$C_4$ alkyl, $C_1$-$C_4$ alkoxy, $CF_3$, CN;
$R_4$ is H, halogen, $C_1$-$C_4$ alkoxy, $CF_3$, $OCF_3$, CN, phenyloxy, —$SO_2$—($C_1$-$C_6$ alkyl), —NHR', —NR'R", $C_1$-$C_4$ alkanoyl, pyridyl, furanyl or thienyl, phenyl, or $C_1$-$C_4$ alkyl optionally substituted with —$CO_2$—($C_1$-$C_6$ alkyl);
$R_{3'}$ is H, or halogen;
R' is H, $C_1$-$C_4$ alkyl, benzyl, $C_1$-$C_6$ alkanoyl, phenyl($C_1$-$C_4$)alkanoyl, pyridyl($C_1$-$C_4$)alkyl, —$SO_2$-alkyl, —$SO_2$-phenyl, —$SO_2$-pyridyl, pyridyl($C_1$-$C_6$)alkanoyl, wherein the alkyl portion of the alkyl and alkanoyl groups are optionally substituted with halogen or $C_1$-$C_4$ alkoxy,
wherein the phenyl and pyridyl groups are optionally substituted with $C_1$-$C_4$ alkyl, $C_1$-$C_4$ alkoxy, halogen, $CF_3$, $OCF_3$;
R" is H or $C_1$-$C_6$ alkyl, wherein the alkyl group is optionally substituted with halogen.

Embodiment 17LL. Compounds according to Embodiment 17KK, wherein
$R_3$ is H, halogen, methyl, methoxy, $CF_3$, or CN;
$R_4$ is halogen, methyl, methoxy, $CF_3$, $OCF_3$, CN, —NHR', or —NR'R";
$R_{3'}$ is H, or halogen;
R' is H, or $C_1$-$C_4$ alkyl; and
R" is H or $C_1$-$C_6$ alkyl, wherein the alkyl group is optionally substituted with halogen.

Embodiment 17MM. Compounds according to Embodiment 17LL wherein $R_3$ is H, or halogen; $R_4$ is halogen, methyl, $CF_3$, or methoxy; and $R_{3'}$ is H, or halogen.

Embodiment 17NN. Compounds according to Embodiment 17MM wherein $R_3$ is H; $R_4$ is halogen (preferably F or Cl, more preferably Cl), methyl, or $CF_3$; and $R_{3'}$ is H. In another aspect, $R_4$ is methyl. In still another aspect, $R_4$ is $CF_3$. In yet another aspect, $R_4$ is Cl.

Embodiment 18. Compounds according to any one of Embodiments 17A, 17B, 17C, 17C1, 17C2, 17C3, 17C4, 17D, 17E, 17E1, 17E2, 17E3, 17E4, 17F, 17G, 17H, 17H1, 17H2, 17H3, 17H4, 17I, 17J, 17K, 17L, 17M, 17N, 17O, 17P, 17Q, 17Q1, 17Q2, 17Q3, 17Q4, 17R, 17S, 17T, 17U, 17V, 17W, 17X, 17Y, 17Y1, 17Y2, 17Y3, 17Y4, 17Z, 17Z1, 17Z2, 17Z3, 17Z4, 17AA, 17BB, 17CC, 17CC1, 17CC2, 17CC3, 17CC4, 17DD, 17EE, 17FF, 17GG, 17HH, 17II, 17JJ, 17KK, 17LL, 17MM, or 17NN, wherein $R_1$ is $C_3$-$C_8$ cycloalkyl optionally substituted with 1 or 2 groups that are independently $C_1$-$C_4$ alkyl, $C_1$-$C_4$ hydroxyalkyl, or OH.

Embodiment 18A. Compounds according to Embodiment 18, wherein the $C_3$-$C_8$ cycloalkyl group is substituted with one or two methyl groups. In still another aspect, the $C_3$-$C_8$ cycloalkyl group is substituted with only —$CH_2$—OH. In yet still another aspect, the $C_3$-$C_8$ cycloalkyl group is substituted with one methyl group and one —$CH_2$—OH.

Embodiment 18B. Compounds according to Embodiment 18, wherein the cycloalkyl group is a $C_3$-$C_6$ cycloalkyl group. In another aspect, the cycloalkyl group is substituted with one or two methyl groups. In still another aspect, the $C_3$-$C_6$ cycloalkyl group is substituted with only —$CH_2$—OH. In yet still another aspect, the $C_3$-$C_6$ cycloalkyl group is substituted with one methyl group and one —$CH_2$—OH. In another aspect, the cycloalkyl group is substituted with at least one OH group. In still another aspect, the cycloalkyl group is substituted with only one OH group. In still another aspect, the cycloalkyl group is a cyclopropyl group.

Embodiment 18C. Compounds according to Embodiment 18, wherein the cycloalkyl group is a $C_5$-$C_6$ cycloalkyl. In another aspect, the $C_5$-$C_6$ cycloalkyl group is substituted with one or two methyl groups. In one aspect, the cycloalkyl group is substituted with one methyl group. In another aspect, the cycloalkyl group is substituted with two methyl groups. In still another aspect, the $C_5$-$C_6$ cycloalkyl group is substituted with only —$CH_2$—OH. In yet still another aspect, the $C_5$-$C_6$ cycloalkyl group is substituted with one methyl group and one —$CH_2$—OH or one OH group. In another aspect, the cycloalkyl group is substituted with at least one OH group. In still another aspect, the cycloalkyl group is substituted with only one OH group. In one aspect, the methyl group and (the —$CH_2$—OH group or the OH group) are in a 1, 2 relationship relative to each other. In another aspect, the methyl group and (the —$CH_2$—OH group or the OH group) are in a 1, 3 relationship relative to each other. In still another aspect, the methyl group and (the —$CH_2$—OH group or the OH group) are in a 1,4 relationship relative to each other.

Embodiment 18D. Compounds according to Embodiment 18, wherein the cycloalkyl group is a $C_6$ cycloalkyl. In another aspect, the $C_6$ cycloalkyl group is substituted with one or two methyl groups. In one aspect, the cycloalkyl group is substituted with one methyl group. In still another aspect, the $C_6$ cycloalkyl group is substituted with only —$CH_2$—OH. In yet still another aspect, the $C_6$ cycloalkyl group is substituted with one methyl group and one —$CH_2$—OH. In another aspect, the cycloalkyl group is substituted with at least one OH group. In one aspect, the methyl group and (the —$CH_2$—OH group or the OH group) are in a 1, 2 relationship relative to each other. In another aspect, the methyl group and (the —$CH_2$—OH group or the OH group) are in a 1, 3 relationship relative to each other. In still another aspect, the methyl group and (the —$CH_2$—OH group or the OH group) are in a 1,4 relationship relative to each other.

Embodiment 18E. Compounds according to Embodiment 18D, wherein
$R_1$ is

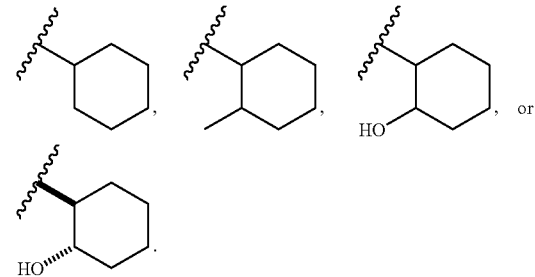

Embodiment 18E1. Compounds according to embodiment 18E, wherein
$R_1$ is

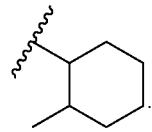

Embodiment 18F. Compounds according to Embodiment 18, wherein the cycloalkyl group is a $C_7$-$C_8$ cycloalkyl.

Embodiment 19. Compounds according to any one of Embodiments 17A, 17B, 17C, 17C1, 17C2, 17C3, 17C4, 17D, 17E, 17E1, 17E2, 17E3, 17E4, 17F, 17G, 17H, 17H1, 17H2, 17H3, 17H4, 17I, 17J, 17K, 17L, 17M, 17N, 17O, 17P, 17Q, 17Q1, 17Q2, 17Q3, 17Q4, 17R, 17S, 17T, 17U, 17V, 17W, 17X, 17Y, 17Y1, 17Y2, 17Y3, 17Y4, 17Z, 17Z1, 17Z2, 17Z3, 17Z4, 17Z5, 17AA, 17BB, 17CC, 17CC1, 17CC2, 17CC3, 17CC4, 17DD, 17EE, 17FF, 17GG, 17HH, 17II, 17JJ, 17KK, 17LL, 17MM, or 17NN, wherein $R_1$ is heterocycloalkyl or heterocycloalkyl($C_1$-$C_4$)alkyl wherein the heterocycloalkyl group is piperidinyl, pyrrolidinyl, tetrahydrofuranyl, pyrazolyl, or morpholinyl, wherein the heterocycloalkyl groups are optionally substituted with 1 or 2 groups that are independently $C_1$-$C_4$ alkyl, $C_1$-$C_4$ alkoxy, phenyl, phenyl($C_1$-$C_4$)alkyl, OH, halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or $C_1$-$C_4$ alkoxycarbonyl.

Embodiment 19A. Compounds according to Embodiment 19, wherein $R_1$ is heterocycloalkyl, which is piperidin-3-yl, piperidin-4-yl, pyrrolidin-2-yl, tetrahydrofuranyl, pyrazolyl, or morpholinyl, wherein the heterocycloalkyl groups are optionally substituted with 1 or 2 groups that are independently $C_1$-$C_4$ alkyl, $C_1$-$C_4$ alkoxy, phenyl, phenyl($C_1$-$C_4$) alkyl, OH, halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or $C_1$-$C_4$ alkoxycarbonyl.

Embodiment 19B. Compounds according to Embodiment 19, wherein $R_1$ is heterocycloalkyl, which is piperidin-3-yl, piperidin-4-yl, pyrrolidinyl, pyrazolyl, or morpholinyl, wherein the heterocycloalkyl groups are optionally substituted with 1 or 2 groups that are independently $C_1$-$C_4$ alkyl, $C_1$-$C_4$ alkoxy, phenyl, phenyl($C_1$-$C_4$)alkyl, OH, halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or $C_1$-$C_4$ alkoxycarbonyl.

Embodiment 19C. Compounds according to Embodiment 19, wherein the heterocycloalkyl groups are optionally substituted with 1 or 2 groups that are independently methyl, methoxy, phenyl, benzyl, OH, halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or tert-butylcarbonyl. In another embodiment, the heterocycloalkyl group is substituted with methyl.

Embodiment 19D. Compounds according to Embodiment 19, wherein $R_1$ is tetrahydrofuranyl, which is optionally substituted with a methyl group.

Embodiment 19E. Compounds according to Embodiment 19, wherein
$R_1$ is heterocycloalkyl($C_1$-$C_4$)alkyl, which is piperidinyl, pyrrolidinyl, tetrahydrofuranyl, pyrazolyl, or morpholinyl, wherein the heterocycloalkyl groups are optionally substituted with 1 or 2 groups that are independently $C_1$-$C_4$ alkyl, $C_1$-$C_4$ alkoxy, phenyl, phenyl($C_1$-$C_4$)alkyl, halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or $C_1$-$C_4$ alkoxycarbonyl.

Embodiment 19F. Compounds according to Embodiment 19, wherein
$R_1$ is heterocycloalkyl($C_1$-$C_4$)alkyl, which is piperidinyl, pyrrolidinyl, pyrazolyl, or morpholinyl, wherein the heterocycloalkyl groups are optionally substituted with 1 or 2 groups that are independently $C_1$-$C_4$ alkyl, $C_1$-$C_4$ alkoxy, phenyl, phenyl($C_1$-$C_4$)alkyl, halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or $C_1$-$C_4$ alkoxycarbonyl.

Embodiment 19G. Compounds according to Embodiment 19, wherein the heterocycloalkyl groups are optionally substituted with 1 or 2 groups that are independently methyl, methoxy, phenyl, benzyl, halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or tert-butylcarbonyl.

Embodiment 19H. Compounds according to Embodiment 19, wherein $R_1$ is tetrahydrofuranyl($C_1$-$C_4$)alkyl, which is optionally substituted with a methyl group.

Embodiment 19I. Compounds according to any one of Embodiments 19, 19B, 19D, 19E, 19F, or 19H, wherein the heterocycloalkyl groups are unsubstituted.

Embodiment 19J. Compounds according to any one of Embodiments 19, 19E, 19F, 19G, 19H, or 19I, wherein the alkyl group is a $C_1$-$C_2$ alkyl group. In another aspect, the alkyl group is a $C_1$ alkyl group.

Embodiment 20. Compounds according to any one of Embodiments 17A, 17B, 17C, 17C1, 17C2, 17C3, 17C4, 17D, 17E, 17E1, 17E2, 17E3, 17E4, 17F, 17G, 17H, 17H1, 17H2, 17H3, 17H4, 17I, 17J, 17K, 17L, 17M, 17N, 17O, 17P, 17Q, 17Q1, 17Q2, 17Q3, 17Q4, 17R, 17S, 17T, 17U, 17V, 17W, 17X, 17Y, 17Y1, 17Y2, 17Y3, 17Y4, 17Z, 17Z1, 17Z2, 17Z3, 17Z4, 17AA, 17BB, 17CC, 17CC1, 17CC2, 17CC3, 17CC4, 17DD, 17EE, 17FF, 17GG, 17HH, 17II 17JJ, 17KK, 17LL, 17MM, or 17NN, wherein $R_1$ is heteroaryl($C_1$-$C_4$) alkyl, wherein the heteroaryl group is pyridyl, pyrimidyl, furanyl, or thienyl and the heteroaryl group is optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkyl, $C_1$-$C_4$ alkoxy or OH.

Embodiment 20A. Compounds according to Embodiment 20, wherein $R_1$ is heteroaryl($C_1$-$C_4$)alkyl, wherein the heteroaryl group is pyridyl, or pyrimidyl, each of which is optionally substituted with 1, or 2 groups that are independently halogen, $CO_2H$, $C_1$-$C_4$ alkoxycarbonyl, $C_1$-$C_4$ alkyl, $C_1$-$C_4$ alkoxy or OH.

Embodiment 20B. Compounds according to Embodiment 20A, wherein the heteroaryl group is substituted with 1, or 2 groups that are independently halogen, methyl, methoxy, or OH.

Embodiment 20C. Compounds according to Embodiment 20A, wherein $R_1$ is heteroaryl($C_1$-$C_4$)alkyl, wherein the heteroaryl group is furanyl, or thienyl each is optionally substituted with 1, 2, or 3 groups that are independently halogen, $C_1$-$C_4$ alkyl, $C_1$-$C_4$ alkoxy or OH.

Embodiment 20D. Compounds according to any one of Embodiments 20, 20A, 20B, or 20C, wherein the alkyl group is a $C_1$-$C_2$ alkyl group. In another aspect, the alkyl group is a $C_1$ alkyl group.

Embodiment 20E. Compounds according to any one of Embodiments 20, 20A, 20B, 20C, or 20D, wherein the heteroaryl group is un-substituted.

Embodiment 21. In another aspect, the invention provides compounds of Formula X

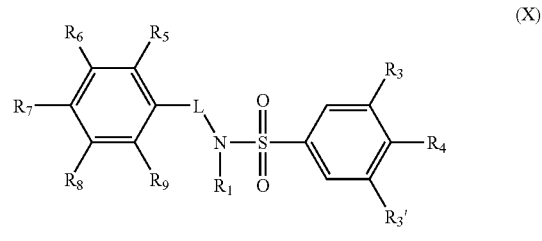

or pharmaceutically acceptable salts thereof, wherein

L is $C_1$-$C_6$ alkylene or $C_2$-$C_6$ alkenylene;

$R_1$ is $C_2$-$C_6$ alkynyl, $C_2$-$C_6$ alkenyl, or $C_1$-$C_8$ alkyl wherein each is optionally substituted with 1, 2, or 3 groups that are independently $C_1$-$C_6$ alkoxy, OH, halogen, CN, $C_1$-$C_6$ thioalkoxy, phenyl, naphthyl, pyridyl, pyrimidyl, furanyl, thienyl, $C_3$-$C_8$ cycloalkyl, $NH_2$, $NH(C_1$-$C_6)$ alkyl, $N(C_1$-$C_6)$alkyl$(C_1$-$C_6$ alkyl), —C(O)$NH_2$, —C(O)NH($C_1$-$C_6$) alkyl, —C(O)N($C_1$-$C_6$)alkyl($C_1$-$C_6$)alkyl, —C(O)phenyl, or $C_1$-$C_6$ alkoxycarbonyl, wherein each of the cyclic groups is optionally substituted with 1, 2, 3, or 4 groups that are independently halogen, $C_1$-$C_4$ alkyl, $C_1$-$C_4$ alkoxy, $NH_2$, NH($C_1$-$C_6$) alkyl, N($C_1$-$C_6$)alkyl($C_1$-$C_6$ alkyl), —$SO_2$—($C_1$-$C_6$) alkyl, or OH;

or $R_1$ is $C_3$-$C_8$ cycloalkyl optionally substituted with 1 or 2 groups that are independently $C_1$-$C_4$ alkyl, $C_1$-$C_4$ hydroxyalkyl, or OH; or $R_1$ is heterocycloalkyl or heterocycloalkyl($C_1$-$C_4$)alkyl wherein the heterocycloalkyl group is piperidinyl, pyrrolidinyl, tetrahydrofuranyl, pyrazolyl, or morpholinyl, wherein the heterocycloalkyl groups are optionally substituted with $C_1$-$C_4$ alkyl, $C_1$-$C_4$ alkoxy, phenyl, phenyl ($C_1$-$C_4$)alkyl, halogen or $C_1$-$C_4$ alkoxycarbonyl; or $R_1$ is heteroaryl($C_1$-$C_4$)alkyl, wherein the heteroaryl group is pyridyl, pyrimidyl, furanyl, or thienyl and the heteroaryl group is optionally substituted with 1, 2, or 3 groups that are independently halogen, $C_1$-$C_4$ alkyl, $C_1$-$C_4$ alkoxy or OH;

$R_3$ is H, halogen, $C_1$-$C_6$ alkyl, $C_1$-$C_6$ alkoxy, $C_1$-$C_6$ haloalkyl, CN, $R_4$ is H, halogen, $C_1$-$C_4$ alkyl optionally substituted with —$CO_2$—($C_1$-$C_6$ alkyl), $C_1$-$C_6$ alkoxy, $C_1$-$C_6$ haloalkyl, $C_1$-$C_6$ haloalkoxy, CN, aryloxy, isocyanato, —$SO_2$—($C_1$-$C_6$ alkyl), —NHR', —NR'R", $C_1$-$C_6$ alkanoyl, pyridyl, phenyl, or $R_3$ and $R_4$ and the carbons to which they are attached form a heterocycloalkyl ring which is optionally substituted with 1, 2, or 3 groups that are independently $C_1$-$C_4$ alkyl, $C_1$-$C_4$ alkoxy, halogen, or $C_1$-$C_4$ alkanoyl wherein the alkanoyl group is optionally substituted with up to 3 halogen atoms;

$R_{3'}$ is H, —$SO_2$—NR'R", halogen, or $R_4$ and $R_{3'}$ and the carbons to which they are attached form a phenyl ring; or $R_4$ and $R_{3'}$ and the carbons to which they are attached form a 1-oxa-2,3-diazacyclopentyl ring;

$R_5$ is H, halogen, $C_1$-$C_6$ alkoxy, $CF_3$, $CO_2H$, $C_1$-$C_4$ alkoxycarbonyl, —O—($C_1$-$C_4$ alkyl)-$CO_2$—($C_1$-$C_4$ alkyl), —C(O)$NH_2$, —C(O)NH($C_1$-$C_4$) alkyl, —C(O)N($C_1$-$C_4$)alkyl($C_1$-$C_4$)alkyl, morpholinyl, oxazolyl, pyrazolyl, thiomorpholinyl, thiomorpholinyl S,S-dioxide, piperidinyl, pyrrolidinyl, halogen, $C_1$-$C_6$ alkyl, phenyl optionally substituted with 1, 2, 3, 4 or 5 groups that are independently halogen, $C_1$-$C_6$ alkyl, or $C_1$-$C_4$ alkoxy, CN, or —($C_1$-$C_4$ alkyl)-$SO_2$-phenyl, $R_6$ is H, $C_1$-$C_6$ alkoxy, halogen, $C_1$-$C_6$ alkyl, $CF_3$, $OCF_3$, phenyl($C_1$-$C_4$)alkoxy, phenyloxy, $CO_2H$, $C_1$-$C_6$ alkoxycarbonyl, —C(O) $NH_2$, —C(O)NH($C_1$-$C_6$) alkyl, —C(O)N($C_1$-$C_6$)alkyl($C_1$-$C_6$) alkyl, CN, $C_2$-$C_6$ alkenyl, or $C_1$-$C_6$ alkyl, wherein the above phenyl groups are optionally substituted with 1, 2, 3, 4 or 5 groups that are independently halogen, $C_1$-$C_6$ alkyl, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or $C_1$-$C_4$ alkoxy, or $R_5$, $R_6$, and the carbons to which they are attached form a phenyl ring, which is optionally substituted with 1 or 2 groups that are independently halogen, $C_1$-$C_4$ alkyl, $C_1$-$C_4$ alkoxy, $CF_3$, or $OCF_3$;

$R_7$ is H, OH, $C_1$-$C_6$ alkoxy, —O—$SO_2$-phenyl where the phenyl is optionally substituted with halogen, halogen, $C_1$-$C_6$ alkyl, phenyloxy, benzyloxy, $CF_3$, $CO_2H$, OH, —O—C(O)—($C_1$-$C_4$ alkyl), $C_1$-$C_6$ alkoxycarbonyl, —C(O)NR$_{30}$R$_{31}$, —NHR', —NR'R", —N(R$_{16}$)C(O)—R$_{17}$, thiazolyl, thiazolyl($C_1$-$C_6$)alkoxy, pyridyl($C_1$-$C_6$) alkoxy, oxazolyl($C_1$-$C_4$)alkoxy, pyrazolyl($C_1$-$C_4$) alkoxy, wherein the thiazolyl, pyridyl, oxazolyl, and pyrazolyl groups are optionally substituted with 1, 2, or 3 groups that are independently $C_1$-$C_6$ alkyl, $C_1$-$C_6$ alkoxy, or halogen, phenyl optionally substituted with 1, 2, 3, 4 or 5 groups that are independently halogen, $C_1$-$C_6$ alkyl, $C_1$-$C_4$ alkoxy, $OCF_3$, CN, or $C_1$-$C_6$ thioalkoxy, —S(O)$_x$—R$_{25}$, or —($C_1$-$C_4$ alkyl)-S(O)$_x$—R$_{25}$;

wherein x is 0, 1, or 2;

$R_{25}$ is $C_1$-$C_6$ alkyl, OH, NR$_{26}$R$_{27}$;

$R_{26}$ and $R_{27}$ are independently H, $C_1$-$C_6$ alkyl, phenyl ($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl;

$R_{30}$ and $R_{31}$ are independently H, $C_1$-$C_6$ alkyl, phenyl, benzyl, pyridyl, imidazolyl, thiazolyl, oxazolyl, or indolyl, or $R_{30}$, $R_{31}$, and the nitrogen to which they are attached form a heterocycloalkyl ring containing from 3 to 7 ring members;

$R_{16}$ is H or $C_1$-$C_6$ alkyl;

$R_{17}$ is $C_1$-$C_6$ alkyl, phenyl, pyridyl, pyrimidyl, pyridazyl, pyrazinyl, thienyl, $C_1$-$C_6$ alkoxy, OH, phenyloxy, pyridyloxy, pyrimidyloxy, pyridazyloxy, pyrazinyloxy, thienyloxy, phenyl($C_1$-$C_4$)alkoxy, or —NR$_{18}$R$_{19}$;

$R_{18}$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$) alkyl; or $R_6$, $R_7$, and the carbons to which they are attached form a phenyl ring, which is optionally substituted with 1 or 2 groups that are independently halogen, $C_1$-$C_4$ alkyl, $C_1$-$C_4$ alkoxy, $CF_3$, or $OCF_3$; or $R_6$ and $R_7$ are —O—$CH_2CH_2$—O—, or —O—$CH_2$—O—;

$R_8$ is H, halogen, $C_1$-$C_6$ alkoxy, $C_1$-$C_6$ alkyl, cyano, —O-phenyl wherein the phenyl group is optionally substituted with halogen, $C_2$-$C_4$ alkenyl, $C_1$-$C_4$ alkoxycarbonyl, benzyloxy, —S(O)$_x$—R$_{25}$, —($C_1$-$C_4$ alkyl)-S(O)$_x$—R$_{25}$, or $CO_2H$, or $R_7$ and $R_8$ are —O—$CH_2CH_2$—O—, or —O—$CH_2$—O—;

$R_9$ is H, halogen, $C_1$-$C_6$ alkyl optionally substituted with —SO2-phenyl, cyano, $C_1$-$C_6$ alkoxy, or phenyl;

R' is H, $C_1$-$C_6$ alkyl, or $C_1$-$C_6$ alkanoyl, wherein the alkyl portion of the alkyl and alkanoyl groups are optionally substituted with halogen, R" is H or $C_1$-$C_6$ alkyl, wherein the alkyl group is optionally substituted with halogen.

Embodiment 21A. Compounds according to Embodiment 21, wherein $R_5$, $R_6$, $R_7$, $R_8$, and $R_9$ are independently hydrogen, halogen, $C_1$-$C_4$ alkyl, $C_1$-$C_4$ alkoxy, $NH_2$, $NH(C_1$-$C_6)$ alkyl, $N(C_1$-$C_6)$alkyl$(C_1$-$C_6$ alkyl), —$SO_2$—$(C_1$-$C_6)$alkyl, or OH.

Embodiment 21B. Compounds according to either Embodiment 21 or Embodiment 21A wherein
$R_1$ is

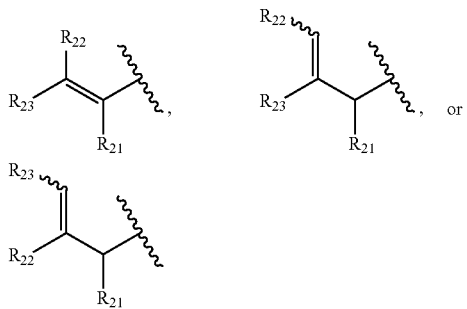

wherein
$R_{21}$ and $R_{22}$ are independently H or $C_1$-$C_6$ alkyl;
$R_{23}$ is H, —C(O)$NR_{30}R_{31}$, $C_1$-$C_6$ alkyl, $CO_2H$, halogen, $C_1$-$C_6$ alkoxycarbonyl, phenyl, naphthyl, benzyl, pyridyl, pyrimidyl, furanyl, or thienyl;
$R_{30}$ and $R_{31}$ are independently H, $C_1$-$C_6$ alkyl, phenyl, benzyl, pyridyl, thiazolyl, oxazolyl, or indolyl, or
$R_{30}$, $R_{31}$, and the nitrogen to which they are attached form a azepanyl, piperidinyl, pyrrolidinyl, morpholinyl, thiomorpholinyl, or thiomorpholinyl 1,1-dioxide.

Embodiment 21B1. Compounds according to Embodiment 21B, wherein $R_{23}$ is H, or —C(O)$NR_{30}R_{31}$, and $R_{30}$ and $R_{31}$ are independently H, $C_1$-$C_6$ alkyl, phenyl, or benzyl.

Embodiment 21B2. Compounds according to Embodiment 21B, wherein $R_{23}$ is H, or —C(O)$NR_{30}R_{31}$, and $R_{30}$ and $R_{31}$ are independently H, methyl, pyridyl, thiazolyl, oxazolyl, or indolyl.

Embodiment 21B2. Compounds according to Embodiment 21B, wherein $R_{23}$ is H, or —C(O)$NR_{30}R_{31}$, and $R_{30}$, $R_{31}$, and the nitrogen to which they are attached form a azepanyl, piperidinyl, pyrrolidinyl, morpholinyl, thiomorpholinyl, or thiomorpholinyl 1,1-dioxide.

Embodiment 21B3. Compounds according to any one of Embodiments 21B, 21B1, or 21B2, wherein $R_{23}$ is H, $C_1$-$C_6$ alkyl, $CO_2H$, or $C_1$-$C_6$ alkoxycarbonyl.

Embodiment 21B4. Compounds according to any one of Embodiments 21B, 21B1, or 21B2, wherein $R_{23}$ is H, phenyl, naphthyl, benzyl, pyridyl, pyrimidyl, furanyl, or thienyl.

Embodiment 21C. Compounds according to either Embodiment 21 or Embodiment 21A wherein
$R_1$ is

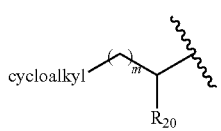

wherein
m is 0, 1, 2, or 3;
$R_{20}$ is H or methyl; and
cycloalkyl is $C_3$-$C_7$ cycloalkyl wherein the cyclic portion is optionally substituted with 1, 2, 3, 4, or 5 groups that are independently halogen, $C_1$-$C_6$ alkyl, OH, or $C_1$-$C_6$ alkoxy.

Embodiment 21D. Compounds according to Embodiment 21, wherein cycloalkyl is cyclopropyl, cyclopentyl, or cyclohexyl, wherein the cyclic portion is optionally substituted with 1, or 2 groups that are independently halogen, $C_1$-$C_4$ alkyl, OH, or $C_1$-$C_4$ alkoxy.

Embodiment 21E. Compounds according to either Embodiment 21 or Embodiment 21A wherein
$R_1$ is of the formula:

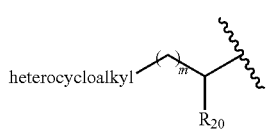

wherein
m is 0, 1, 2, or 3;
$R_{20}$ is H or methyl; and
heterocycloalkyl is 4-oxo-4H-chromen-3-yl, 2H-chromen-3-yl, pyrrolidinonyl dione, isoindol-2-yl dione, 1,3-dioxolan-2-yl, dioxanyl, or tetrahydropyran-2-yl, wherein the cyclic portion of each is optionally substituted with 1, 2, 3, 4, or 5 groups that are independently $C_1$-$C_4$ alkyl, $C_1$-$C_4$ alkoxy, or halogen.

Embodiment 21F. Compounds according to Embodiment 21E, wherein m is 0 or 1. In another aspect, m is 0 or 1 and heterocycloalkyl is isoindol-2-yl dione, 4-oxo-4H-chromen-3-yl, or 2H-chromen-3-yl.

Embodiment 21G. Compounds according to Embodiment 21E, wherein m is 1 or 2. In another aspect, m is 1 or 2 and heterocycloalkyl is isoindol-2-yl dione, 4-oxo-4H-chromen-3-yl, or 2H-chromen-3-yl.

Embodiment 21H. Compounds according to any one of Embodiments 21, 21A, 21B, 21C, 21D, 21E, 21F, or 21G, wherein
$R_5$ is H, $C_1$-$C_6$ alkoxy, $CF_3$, $CO_2H$, $C_1$-$C_4$ alkoxycarbonyl, —C(O)$NH_2$, —C(O)NH($C_1$-$C_4$)alkyl, —C(O)N($C_1$-$C_4$)alkyl($C_1$-$C_4$)alkyl, morpholinyl, oxazolyl, pyrazolyl, thiomorpholinyl, thiomorpholinyl S,S-dioxide, piperidinyl, pyrrolidinyl, halogen, $C_1$-$C_6$ alkyl, phenyl optionally substituted with 1, 2, 3, 4 or 5 groups that are independently halogen, $C_1$-$C_6$ alkyl, or $C_1$-$C_4$ alkoxy, CN, —($C_1$-$C_4$ alkyl)-$SO_2$-phenyl,
$R_6$ is H, $C_1$-$C_6$ alkoxy, halogen, $C_1$-$C_6$ alkyl, $CF_3$, $OCF_3$, phenyl($C_1$-$C_4$)alkoxy, phenyloxy, $CO_2H$, $C_1$-$C_6$ alkoxycarbonyl, —C(O)$NH_2$, —C(O)NH($C_1$-$C_6$) alkyl, —C(O)N($C_1$-$C_6$)alkyl($C_1$-$C_6$) alkyl, CN, $C_2$-$C_6$ alkenyl, wherein the above phenyl groups are optionally substituted with 1, 2, 3, 4 or 5 groups that are independently halogen, $C_1$-$C_6$ alkyl, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or $C_1$-$C_4$ alkoxy;
$R_7$ is H, OH, $C_1$-$C_6$ alkoxy, —O—$SO_2$-phenyl, halogen, $C_1$-$C_6$ alkyl, phenyloxy, $CF_3$, $CO_2H$, $C_1$-$C_6$ alkoxycarbonyl, —C(O)$NR_{30}R_{31}$, —NHR', —NR'R", —N($R_{16}$)C(O)—$R_{17}$, thiazolyl($C_1$-$C_6$)alkoxy, pyridyl($C_1$-$C_6$) alkoxy, oxazolyl($C_1$-$C_4$)alkoxy, pyrazolyl($C_1$-$C_4$) alkoxy, wherein the thiazolyl, pyridyl, oxazolyl, and pyrazolyl groups are optionally substituted with 1, 2, or 3 groups that are independently $C_1$-$C_6$ alkyl, $C_1$-$C_6$ alkoxy, or halogen, phenyl optionally substituted with 1, 2, 3, 4 or 5 groups that are independently halogen, $C_1$-$C_6$ alkyl, $C_1$-$C_4$ alkoxy, $OCF_3$, CN, $CO_2H$, $C_1$-$C_6$ alkoxycarbonyl, —C(O)$NH_2$, —C(O)NH($C_1$-$C_4$) alkyl, —C(O)N($C_1$-$C_4$)alkyl($C_1$-$C_4$) alkyl, —S(O)$_x$—$R_{25}$, or —($C_1$-$C_4$ alkyl)-S(O)$_x$—$R_{25}$ or $C_1$-$C_6$ thioalkoxy, wherein $R_{30}$ and $R_{31}$ are independently H, $C_1$-$C_6$ alkyl, phenyl, benzyl, pyridyl, imidazolyl, thiazolyl, oxazolyl, or indolyl, or $R_{30}$, $R_{31}$, and the nitrogen to which they are attached form a heterocycloalkyl ring containing from 3 to 7 ring members;

$R_{16}$ is H or $C_1$-$C_6$ alkyl;

$R_{17}$ is $C_1$-$C_6$ alkyl, phenyl, pyridyl, pyrimidyl, pyridazyl, pyrazinyl, thienyl, $C_1$-$C_6$ alkoxy, OH, phenyloxy, pyridyloxy, pyrimidyloxy, pyridazyloxy, pyrazinyloxy, thienyloxy, phenyl($C_1$-$C_4$)alkoxy, or —$NR_{18}R_{19}$;

$R_{18}$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$) alkyl;

$R_8$ is H, halogen, $C_1$-$C_6$ alkoxy, $C_1$-$C_6$ alkyl, —S(O)$_x$—$R_{25}$, —($C_1$-$C_4$ alkyl)-S(O)$_x$—$R_{25}$ or $CO_2H$;

$R_9$ is H, halogen, $C_1$-$C_6$ alkoxy, $C_1$-$C_6$ alkyl,

R' is H, $C_1$-$C_6$ alkyl, or $C_1$-$C_6$ alkanoyl, wherein the alkyl portion of the alkyl and alkanoyl groups are optionally substituted with halogen, R" is H or $C_1$-$C_6$ alkyl, wherein the alkyl group is optionally substituted with halogen.

Embodiment 21I. Compounds according to Embodiment 21H, wherein $R_5$ is H, $C_1$-$C_4$ alkoxy, $CF_3$, $CO_2H$, $C_1$-$C_4$ alkoxycarbonyl, —C(O)$NH_2$, —C(O)NH($C_1$-$C_4$) alkyl, or —C(O)N($C_1$-$C_4$)alkyl($C_1$-$C_4$)alkyl;

$R_6$ is H, $C_1$-$C_4$ alkoxy, halogen, $C_1$-$C_4$ alkyl, $CF_3$, $OCF_3$, $CO_2H$, $C_1$-$C_4$ alkoxycarbonyl, —C(O)$NH_2$, —C(O)NH ($C_1$-$C_4$) alkyl, —C(O)N($C_1$-$C_4$)alkyl($C_1$-$C_4$) alkyl, CN, or $C_2$-$C_6$ alkenyl;

$R_8$ is H, halogen, $C_1$-$C_4$ alkoxy, $C_1$-$C_4$ alkyl, or $CO_2H$; and $R_9$ is H, halogen, $C_1$-$C_4$ alkoxy, or $C_1$-$C_4$ alkyl.

Embodiment 21J. Compounds according to Embodiment 21I, wherein $R_3$ is H, halogen, methyl, methoxy, $CF_3$, or CN; $R_4$ is halogen, methoxy, methyl, $CF_3$, $OCF_3$, or CN; $R_{3'}$ is H, or halogen.

Embodiment 21K. Compounds according to Embodiment 21J, wherein $R_7$ is H, OH, $C_1$-$C_4$ alkoxy, halogen, $C_1$-$C_4$ alkyl, $CF_3$, $CO_2H$, $C_1$-$C_6$ alkoxycarbonyl, —C(O)$NR_{30}R_{31}$, thiazolyl($C_1$-$C_6$)alkoxy, pyridyl($C_1$-$C_6$)alkoxy, oxazolyl($C_1$-$C_4$)alkoxy, pyrazolyl($C_1$-$C_4$)alkoxy, wherein the thiazolyl, pyridyl, oxazolyl, and pyrazolyl groups are optionally substituted with 1, 2, or 3 groups that are independently $C_1$-$C_6$ alkyl, $C_1$-$C_6$ alkoxy, or halogen, or phenyl optionally substituted with 1, 2, 3, 4 or 5 groups that are independently halogen, $C_1$-$C_6$ alkyl, $C_1$-$C_4$ alkoxy, $OCF_3$, $CO_2H$, $C_1$-$C_6$ alkoxycarbonyl, CN, or $C_1$-$C_6$ thioalkoxy; and $R_{30}$ and $R_{31}$ are independently H, $C_1$-$C_6$ alkyl, phenyl, or benzyl.

Embodiment 21K1. Compounds according to Embodiment 21J, wherein $R_7$ is —S(O)$_x$—$R_{25}$, or —($C_1$-$C_4$ alkyl)-S(O)$_x$—$R_{25}$ $R_{25}$ is $C_1$-$C_6$ alkyl, OH, $NR_{26}R_{27}$;

$R_{26}$ and $R_{27}$ are independently H, $C_1$-$C_6$ alkyl, phenyl($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 21K2. Compounds according to Embodiment 21K1, wherein $R_{25}$ is $C_1$-$C_6$ alkyl or OH.

Embodiment 21K3. Compounds according to Embodiment 21K1, wherein $R_{25}$ is $C_1$-$C_4$ alkyl or $NR_{26}R_{27}$; and $R_{26}$ and $R_{27}$ are independently H, $C_1$-$C_6$ alkyl, phenyl($C_1$-$C_4$ alkyl), phenyl, or pyridyl.

Embodiment 21K4. Compounds according to Embodiment 21K1, wherein $R_{25}$ is $C_1$-$C_4$ alkyl or $NR_{26}R_{27}$; and $R_{26}$, $R_{27}$ and the nitrogen to which they are attached represent pyrrolidinyl, piperidinyl, piperazinyl, morpholinyl, or imidazolidinyl.

Embodiment 21L. Compounds according to Embodiment 21K, wherein $R_7$ is H, OH, $C_1$-$C_4$ alkoxy, halogen, $C_1$-$C_4$ alkyl, $CF_3$, $CO_2H$, —C(O) $NR_{30}R_{31}$, or $C_1$-$C_4$ alkoxycarbonyl; and $R_{30}$ and $R_{31}$ are independently H or $C_1$-$C_6$ alkyl.

Embodiment 21M. Compounds according to Embodiment 21L, wherein $R_7$ is H, OH, methoxy, halogen, methyl, $CF_3$, $CO_2H$, —C(O)$NR_{30}R_{31}$, or $C_1$-$C_2$ alkoxycarbonyl; and $R_{30}$ and $R_{31}$ are independently H or $C_1$-$C_4$ alkyl.

Embodiment 21N. Compounds according to Embodiment 21M, wherein $R_7$ is $CO_2H$, —C(O)$NR_{30}R_{31}$, or $C_1$-$C_2$ alkoxycarbonyl.

Embodiment 21O. Compounds according to Embodiment 21M, wherein $R_7$ is OH, methoxy, halogen, methyl, or $CF_3$.

Embodiment 21P. Compounds according to any one of Embodiments 21K, 21K1, 21K2, 21K3, 21K4, 21L, 21M, 21N or 21O, wherein $R_3$ is H, or halogen;

$R_4$ is halogen, methyl, $CF_3$, or methoxy; and $R_{3'}$ is H or halogen.

Embodiment 21Q. Compounds according to Embodiment 21P, wherein $R_5$ is H, methoxy, $CF_3$, $CO_2H$, $C_1$-$C_2$ alkoxycarbonyl, —C(O)$NH_2$, —C(O)NH($C_1$-$C_4$)alkyl, or —C(O)N($C_1$-$C_4$)alkyl($C_1$-$C_4$)alkyl;

$R_6$ is H, $C_1$-$C_2$ alkoxy, halogen, $C_1$-$C_2$ alkyl, $CF_3$, $OCF_3$, $CO_2H$, $C_1$-$C_2$ alkoxycarbonyl, —C(O)$NH_2$, —C(O)NH ($C_1$-$C_4$)alkyl, or —C(O)N($C_1$-$C_4$)alkyl($C_1$-$C_4$) alkyl;

$R_8$ is H or halogen (preferred halogens are F or Cl); and $R_9$ is H or halogen (preferred halogens are F or Cl).

Embodiment 21R. Compounds according to Embodiment 21Q wherein $R_3$ is H; $R_4$ is halogen (preferably F or Cl, more preferably Cl); and $R_{3'}$ is H. In another aspect, $R_4$ is methyl. In still another aspect, $R_4$ is $CF_3$. In yet another aspect, $R_4$ is Cl.

Embodiment 21S. Compounds according to Embodiment 21R, wherein $R_5$ is H, methoxy, $CF_3$, $CO_2H$, or $C_1$-$C_2$ alkoxycarbonyl; $R_6$ is H, methoxy, halogen, methyl, $CF_3$, $OCF_3$, $CO_2H$, or $C_1$-$C_2$ alkoxycarbonyl (in one aspect, $C_2$ alkoxycarbonyl); $R_8$ is H, F or Cl; and $R_9$ is H, F or Cl.

Embodiment 21T. Compounds according to Embodiment 21J, wherein $R_7$ is H, —NHR', —NR'R" or —N($R_{16}$) C(O)— $R_{17}$; $R_{16}$ is H or $C_1$-$C_4$ alkyl; $R_{17}$ is $C_1$-$C_6$ alkyl, phenyl, pyridyl, pyrimidyl, pyridazyl, pyrazinyl, thienyl, $C_1$-$C_6$ alkoxy, phenyloxy, pyridyloxy, pyrimidyloxy, pyridazyloxy, pyrazinyloxy, thienyloxy, phenyl($C_1$-$C_4$)alkoxy, or —$NR_{18}R_{19}$; and $R_{18}$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$) alkyl; wherein R' is H, $C_1$-$C_4$ alkyl, or $C_1$-$C_4$ alkanoyl; R" is $C_1$-$C_4$ alkyl, wherein the alkyl group is optionally substituted with halogen.

Embodiment 21U. Compounds according to Embodiment 21T, wherein $R_3$ is H, or halogen; $R_4$ is halogen, methyl, $CF_3$, or methoxy; and $R_{3'}$ is H or halogen. In another aspect, $R_4$ is methyl. In still another aspect, $R_4$ is $CF_3$. In yet another aspect, $R_4$ is Cl.

Embodiment 21V. Compounds according to Embodiment 21U, wherein $R_5$ is H, methoxy, $CF_3$, $CO_2H$, $C_1$-$C_2$ alkoxycarbonyl, —C(O)$NH_2$, —C(O)NH($C_1$-$C_4$)alkyl, or —C(O)N ($C_1$-$C_4$)alkyl($C_1$-$C_4$)alkyl;

$R_6$ is H, $C_1$-$C_2$ alkoxy, halogen, $C_1$-$C_2$ alkyl, $CF_3$, $OCF_3$, $CO_2H$, $C_1$-$C_2$ alkoxycarbonyl, —C(O)$NH_2$, —C(O)NH ($C_1$-$C_4$)alkyl, or —C(O)N($C_1$-$C_4$)alkyl($C_1$-$C_4$)alkyl;

$R_8$ is H or halogen (preferred halogens are F or Cl); and $R_9$ is H or halogen (preferred halogens are F or Cl).

Embodiment 21W. Compounds according to Embodiment 21V wherein $R_3$ is H; $R_4$ is halogen (preferably F or Cl, more preferably Cl), methyl, or $CF_3$; and $R_{3'}$ is H.

Embodiment 21X. Compounds according to Embodiment 21W, wherein $R_5$ is H, methoxy, $CF_3$, $CO_2H$, or $C_1$-$C_2$ alkoxycarbonyl;

$R_6$ is H, methoxy, halogen, methyl, $CF_3$, $OCF_3$, $CO_2H$, or $C_1$-$C_2$ alkoxycarbonyl (in one aspect, $C_2$ alkoxycarbonyl);

$R_8$ is H, F or Cl; and $R_9$ is H, F or Cl.

Embodiment 21Y. Compounds according to any one of Embodiments 21U, 21V, 21W, or 21X, wherein $R_7$ is H or —N($R_{16}$)C(O)—$R_{17}$; wherein $R_{16}$ is H or $C_1$-$C_4$ alkyl; $R_{17}$ is $C_1$-$C_6$ alkyl, phenyl, pyridyl, pyrimidyl, pyridazyl, pyrazinyl, thienyl, $C_1$-$C_6$ alkoxy, phenyloxy, pyridyloxy, pyrimidyloxy, pyridazyloxy, pyrazinyloxy, thienyloxy, phenyl($C_1$-$C_4$)alkoxy, or —$NR_{18}R_{19}$; and $R_{18}$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$) alkyl.

Embodiment 21Z. Compounds according to Embodiment 21Y, wherein $R_{17}$ is $C_1$-$C_4$ alkyl, phenyl, pyridyl, pyrimidyl, pyridazyl, pyrazinyl, thienyl, $C_1$-$C_4$ alkoxy, phenyloxy, pyridyloxy, pyrimidyloxy, pyridazyloxy, pyrazinyloxy, thienyloxy, phenyl($C_1$-$C_4$) alkoxy.

Embodiment 21AA. Compounds according to Embodiment 21Z, wherein $R_{17}$ is $C_1$-$C_4$ alkyl, $C_1$-$C_4$ alkoxy, phenyl, phenyloxy, or phenyl($C_1$-$C_2$)alkoxy.

Embodiment 21BB. Compounds according to Embodiment 21Z, wherein $R_{17}$ is pyridyl, pyrimidyl, pyridazyl, pyrazinyl, thienyl, pyridyloxy, pyrimidyloxy, pyridazyloxy, pyrazinyloxy, or thienyloxy.

Embodiment 21BB. Compounds according to Embodiment 21Z, wherein $R_{17}$ is —$NR_{18}R_{19}$; and $R_{18}$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$) alkyl.

Embodiment 21CC. Compounds according to Embodiment 21Y, wherein $R_{17}$ is —$NR_{18}R_{19}$; and $R_{18}$ and $R_{19}$ are independently H, $C_1$-$C_6$ alkyl, phenyl, pyridyl, thienyl, piperidinyl, pyrrolidinyl, morpholinyl, or phenyl($C_1$-$C_4$) alkyl.

Embodiment 21DD. Compounds according to Embodiment 21CC, wherein $R_{18}$ and $R_{19}$ are independently H, $C_1$-$C_4$ alkyl, phenyl, or phenyl($C_1$-$C_2$) alkyl.

Embodiment 21EE. Compounds according to Embodiment 21CC, wherein $R_{18}$ and $R_{19}$ are independently H, pyridyl, thienyl, piperidinyl, pyrrolidinyl, morpholinyl, thiomorpholinyl, thiomorpholinyl 1,1-dioxide, or tetrahydro-thiopyranyl 1,1-dioxide. In another aspect, one of $R_{18}$ and $R_{19}$ is H.

Embodiment 21EE1. Compounds according to Embodiment 21CC, wherein $R_{18}$ and $R_{19}$ are independently H, pyridyl, piperidinyl, pyrrolidinyl, or morpholinyl. In another aspect, one of $R_{18}$ and $R_{19}$ is H. In another aspect, only one of $R_{18}$ and $R_{19}$ is H.

Embodiment 21EE2. Compounds according to Embodiment 21CC, wherein $R_{18}$ and $R_{19}$ are independently H, thienyl, thiomorpholinyl, thiomorpholinyl 1,1-dioxide, or tetrahydro-thiopyranyl 1,1-dioxide. In another aspect, one of $R_{18}$ and $R_{19}$ is H. In another aspect, only one of $R_{18}$ and $R_{19}$ is H.

Embodiment 21FF. Compounds according to any one of Embodiments 21U, 21V, 21W, or 21X, wherein $R_7$ is H, —NHR', or —NR'R"; wherein R' is H, $C_1$-$C_4$ alkyl, or $C_1$-$C_4$ alkanoyl; R" is $C_1$-$C_4$ alkyl, wherein the alkyl group is optionally substituted with halogen.

Embodiment 21GG. Compounds according to Embodiment 21K, wherein $R_7$ is thiazolyl($C_1$-$C_4$)alkoxy, pyridyl($C_1$-$C_4$)alkoxy, oxazolyl($C_1$-$C_4$)alkoxy, pyrazolyl($C_1$-$C_4$)alkoxy, wherein the thiazolyl, pyridyl, oxazolyl, and pyrazolyl groups are optionally substituted with 1, 2, or 3 groups that are independently $C_1$-$C_4$ alkyl, $C_1$-$C_4$ alkoxy, or halogen.

Embodiment 21HH. Compounds according to Embodiment 21GG, wherein $R_7$ is thiazolyl($C_1$-$C_2$)alkoxy, pyridyl($C_1$-$C_2$)alkoxy, oxazolyl($C_1$-$C_2$)alkoxy, or pyrazolyl($C_1$-$C_2$) alkoxy, wherein the thiazolyl, pyridyl, oxazolyl, and pyrazolyl groups are optionally substituted with 1, or 2 groups that are independently methyl, methoxy, or halogen.

Embodiment 21II. Compounds according to Embodiment 21K, wherein $R_7$ is phenyl optionally substituted with 1, 2, 3, 4 or 5 groups that are independently halogen, $C_1$-$C_4$ alkyl, $C_1$-$C_4$ alkoxy, $OCF_3$, CN, $CO_2H$, $C_1$-$C_4$ alkoxycarbonyl, $C(O)NH_2$, —$C(O)NH(C_1$-$C_4)$ alkyl, —$C(O)N(C_1$-$C_4)$alkyl($C_1$-$C_4)$alkyl, or $C_1$-$C_4$ thioalkoxy. In another aspect, the phenyl is optionally substituted with 1, 2, or 3 groups, which are independently halogen, $C_1$-$C_4$ alkyl, $C_1$-$C_4$ alkoxy, $OCF_3$, CN, $CO_2H$, $C_1$-$C_4$ alkoxycarbonyl, $C(O)NH_2$, —$C(O)NH$ ($C_1$-$C_4$)alkyl, or —$C(O)N(C_1$-$C_4)$alkyl($C_1$-$C_4)$alkyl.

Embodiment 21II1. Compounds according to Embodiment 21K, wherein $R_7$ is phenyl optionally substituted with 1, 2, or 3 groups that are independently halogen, $C_1$-$C_2$ alkyl, $C_1$-$C_2$ alkoxy, $OCF_3$, CN, $CO_2H$, $C_1$-$C_2$ alkoxycarbonyl, $C(O)NH_2$, —$C(O)NH(C_1$-$C_4)$ alkyl, or —$C(O)N(C_1$-$C_4)$ alkyl($C_1$-$C_4$)alkyl. In another aspect, the phenyl is optionally substituted with 1 or 2 groups, which are independently halogen, methyl, methoxy, $CO_2H$, $C_1$-$C_2$ alkoxycarbonyl, $C(O)NH_2$, —$C(O)NH(C_1$-$C_4)$alkyl, or —$C(O)N(C_1$-$C_4)$alkyl($C_1$-$C_4)$alkyl.

Embodiment 21JJ. Compounds according to any one of Embodiments 21, 21A, 21B, 21C, 21D, 21E, 21F, or 21G, wherein $R_5$, $R_6$, and the carbons to which they are attached form a phenyl ring, which is optionally substituted with 1 or 2 groups that are independently halogen, $C_1$-$C_4$ alkyl, $C_1$-$C_4$ alkoxy, $CF_3$, or $OCF_3$; and $R_7$, $R_8$, and $R_9$ are H.

Embodiment 21KK. Compounds according to any one of Embodiments 21, 21A, 21B, 21C, 21D, 21E, 21F, or 21G, wherein $R_5$, $R_8$, and $R_9$ are H; and $R_6$, $R_7$, and the carbons to which they are attached form a phenyl ring, which is optionally substituted with 1 or 2 groups that are independently halogen, $C_1$-$C_4$ alkyl, $C_1$-$C_4$ alkoxy, $CF_3$, or $OCF_3$;

Embodiment 21LL. Compounds according to any one of Embodiments 21, 21A, 21B, 21C, 21D, 21E, 21F, or 21G, wherein $R_5$, $R_6$, and $R_9$ are H; and $R_7$ and $R_8$ are —O—$CH_2CH_2$—O—, or —O—$CH_2$—O—.

Embodiment 21MM. Compounds according to any one of Embodiments 21JJ, 21KK, or 21LL wherein $R_3$ is H, halogen, methyl, methoxy, $CF_3$, or CN; $R_4$ is halogen, methoxy, methyl, $CF_3$, $OCF_3$, or CN; $R_{3'}$ is H, or halogen.

Embodiment 21NN. Compounds according to Embodiment 21MM, wherein $R_3$ is H, or halogen (in one aspect F or Cl); $R_4$ is halogen (in one aspect F or Cl), methyl, $CF_3$, or methoxy; and $R_{3'}$ is H or halogen (in one aspect F or Cl). In another aspect, $R_4$ is methyl. In still another aspect, $R_4$ is $CF_3$. In yet another aspect, $R_4$ is Cl.

Embodiment 21OO. Compounds according to either Embodiment 21MM or Embodiment 21NN, wherein L is a $C_1$-$C_4$ alkyl. In another aspect, L is $C_1$-$C_2$ alkyl. In yet another aspect, L is $C_3$-$C_4$ alkyl.

Embodiment 21PP. Compounds according to either Embodiment 21MM or Embodiment 21NN, wherein L is a $C_2$-$C_5$ alkenyl. In another aspect, L is $C_2$-$C_4$ alkenyl. In yet another aspect, L is $C_3$-$C_4$ alkenyl.

Embodiment 22. Compounds according to either Embodiment 21 or 21A, of the formula:

wherein $R_{20}$ is H or methyl;

$R_{50}$ is H, or $C_1$-$C_6$ alkyl; and $R_{55}$ is H, $C_1$-$C_4$ alkyl, phenyl, heteroaryl selected from the group consisting of pyridyl, pyrimidyl, benzofuranyl, furanyl or indolyl, or $C_3$-$C_6$ cycloalkyl.

Embodiment 22A. Compounds according to Embodiment 22, wherein $R_5$ is H, $C_1$-$C_6$ alkoxy, $CF_3$, $CO_2H$, $C_1$-$C_4$ alkoxycarbonyl, —C(O)$NH_2$, —C(O)NH($C_1$-$C_4$)alkyl, —C(O)N($C_1$-$C_4$)alkyl($C_1$-$C_4$)alkyl, morpholinyl, oxazolyl, pyrazolyl, thiomorpholinyl, thiomorpholinyl S,S-dioxide, piperidinyl, pyrrolidinyl, halogen, $C_1$-$C_6$ alkyl, phenyl optionally substituted with 1, 2, 3, 4 or 5 groups that are independently halogen, $C_1$-$C_6$ alkyl, or $C_1$-$C_4$ alkoxy, CN, —($C_1$-$C_4$ alkyl)-$SO_2$-phenyl, $R_6$ is H, $C_1$-$C_6$ alkoxy, halogen, $C_1$-$C_6$ alkyl, $CF_3$, $OCF_3$, phenyl($C_1$-$C_4$)alkoxy, phenyloxy, $CO_2H$, $C_1$-$C_6$ alkoxycarbonyl, —C(O)$NH_2$, —C(O)NH($C_1$-$C_6$) alkyl, —C(O)N($C_1$-$C_6$)alkyl($C_1$-$C_6$) alkyl, CN, $C_2$-$C_6$ alkenyl, wherein the above phenyl groups are optionally substituted with 1, 2, 3, 4 or 5 groups that are independently halogen, $C_1$-$C_6$ alkyl, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, or $C_1$-$C_4$ alkoxy;

$R_7$ is H, OH, $C_1$-$C_6$ alkoxy, —O—$SO_2$-phenyl, halogen, $C_1$-$C_6$ alkyl, phenyloxy, $CF_3$, $CO_2H$, $C_1$-$C_6$ alkoxycarbonyl, —C(O)$NR_{30}R_{31}$, —NHR', —NR'R'', —N($R_{16}$)C(O)—$R_{17}$, thiazolyl($C_1$-$C_6$)alkoxy, pyridyl($C_1$-$C_6$) alkoxy, oxazolyl($C_1$-$C_4$)alkoxy, pyrazolyl($C_1$-$C_4$) alkoxy, wherein the thiazolyl, pyridyl, oxazolyl, and pyrazolyl groups are optionally substituted with 1, 2, or 3 groups that are independently $C_1$-$C_6$ alkyl, $C_1$-$C_6$ alkoxy, or halogen, phenyl optionally substituted with 1, 2, 3, 4 or 5 groups that are independently halogen, $C_1$-$C_6$ alkyl, $C_1$-$C_4$ alkoxy, $OCF_3$, CN, $CO_2H$, $C_1$-$C_6$ alkoxycarbonyl, C(O)$NH_2$, —C(O)NH($C_1$-$C_4$), —C(O)N($C_1$-$C_4$)alkyl($C_1$-$C_4$) alkyl, $C_1$-$C_6$ thioalkoxy, —S(O)$_x$—$R_{25}$, or —($C_1$-$C_4$ alkyl)-S(O)$_x$—$R_{25}$; wherein x is 0, 1, or 2;

$R_{25}$ is $C_1$-$C_6$ alkyl, OH, $NR_{26}R_{27}$;

$R_{26}$ and $R_{27}$ are independently H, $C_1$-$C_6$ alkyl, phenyl($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl $R_{30}$ and $R_{31}$ are independently H, $C_1$-$C_6$ alkyl, phenyl, benzyl, pyridyl, imidazolyl, thiazolyl, oxazolyl, or indolyl, or $R_{30}$, $R_{31}$, and the nitrogen to which they are attached form a heterocycloalkyl ring containing from 3 to 7 ring members;

$R_{16}$ is H or $C_1$-$C_6$ alkyl;

$R_{17}$ is $C_1$-$C_6$ alkyl, phenyl, pyridyl, pyrimidyl, pyridazyl, pyrazinyl, thienyl, $C_1$-$C_6$ alkoxy, OH, phenyloxy, pyridyloxy, pyrimidyloxy, pyridazyloxy, pyrazinyloxy, thienyloxy, phenyl($C_1$-$C_4$)alkoxy, or —$NR_{18}R_{19}$;

$R_{18}$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$) alkyl;

$R_8$ is H, halogen, $C_1$-$C_6$ alkoxy, $C_1$-$C_6$ alkyl, —S(O)$_x$—$R_{25}$, —($C_1$-$C_4$ alkyl)-S(O)$_x$—$R_{25}$, or $CO_2H$;

$R_9$ is H, halogen, $C_1$-$C_6$ alkoxy, $C_1$-$C_6$ alkyl,

R' is H, $C_1$-$C_6$ alkyl, or $C_1$-$C_6$ alkanoyl, wherein the alkyl portion of the alkyl and alkanoyl groups are optionally substituted with halogen, R'' is H or $C_1$-$C_6$ alkyl, wherein the alkyl group is optionally substituted with halogen.

Embodiment 22B. Compounds according to Embodiment 22A, wherein $R_5$ is H, $C_1$-$C_4$ alkoxy, $CF_3$, $CO_2H$, $C_1$-$C_4$ alkoxycarbonyl, —C(O)$NH_2$, —C(O)NH($C_1$-$C_4$)alkyl, or —C(O)N($C_1$-$C_4$)alkyl($C_1$-$C_4$)alkyl;

$R_6$ is H, $C_1$-$C_4$ alkoxy, halogen, $C_1$-$C_4$ alkyl, $CF_3$, $OCF_3$, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, CN, or $C_2$-$C_6$ alkenyl;

$R_8$ is H, halogen, $C_1$-$C_4$ alkoxy, $C_1$-$C_4$ alkyl, —S(O)$_x$—$R_{25}$, or —($C_1$-$C_4$ alkyl)-S(O)$_x$—$R_{25}$ or $CO_2H$; and $R_9$ is H, halogen, $C_1$-$C_4$ alkoxy, or $C_1$-$C_4$ alkyl.

Embodiment 22C. Compounds according to Embodiment 22B, wherein $R_3$ is H, halogen, methyl, methoxy, $CF_3$, or CN; $R_4$ is halogen, methoxy, methyl, $CF_3$, $OCF_3$, or CN; $R_{3'}$ is H, or halogen.

Embodiment 22D. Compounds according to Embodiment 22C, wherein $R_7$ is H, OH, $C_1$-$C_4$ alkoxy, halogen, $C_1$-$C_4$ alkyl, $CF_3$, $CO_2H$, $C_1$-$C_6$ alkoxycarbonyl, —C(O)$NR_{30}R_{31}$, thiazolyl($C_1$-$C_6$)alkoxy, pyridyl($C_1$-$C_6$)alkoxy, oxazolyl($C_1$-$C_4$)alkoxy, pyrazolyl($C_1$-$C_4$)alkoxy, wherein the thiazolyl, pyridyl, oxazolyl, and pyrazolyl groups are optionally substituted with 1, 2, or 3 groups that are independently $C_1$-$C_6$ alkyl, $C_1$-$C_6$ alkoxy, or halogen, or phenyl optionally substituted with 1, 2, 3, 4 or 5 groups that are independently halogen, $C_1$-$C_6$ alkyl, $C_1$-$C_4$ alkoxy, $OCF_3$, $CO_2H$, $C_1$-$C_6$ alkoxycarbonyl, CN, or $C_1$-$C_6$ thioalkoxy; and $R_{30}$ and $R_{31}$ are independently H, $C_1$-$C_6$ alkyl, phenyl, or benzyl.

Embodiment 22D1. Compounds according to Embodiment 22C, wherein $R_7$ is —S(O)$_x$—$R_{25}$, or —($C_1$-$C_4$ alkyl)-S(O)$_x$—$R_{25}$ $R_{25}$ is $C_1$-$C_6$ alkyl, OH, $NR_{26}R_{27}$;

$R_{26}$ and $R_{27}$ are independently H, $C_1$-$C_6$ alkyl, phenyl($C_1$-$C_4$ alkyl), phenyl, or pyridyl; or $R_{26}$, $R_{27}$ and the nitrogen to which they are attached represent pyrrolidinyl, piperidinyl, piperazinyl, morpholinyl, or imidazolidinyl.

Embodiment 22D2. Compounds according to Embodiment 21D1, wherein $R_{25}$ is $C_1$-$C_6$ alkyl or OH.

Embodiment 22D3. Compounds according to Embodiment 21D1, wherein $R_{25}$ is $C_1$-$C_4$ alkyl or $NR_{26}R_{27}$; and $R_{26}$ and $R_{27}$ are independently H, $C_1$-$C_6$ alkyl, phenyl($C_1$-$C_4$ alkyl), phenyl, or pyridyl.

Embodiment 22D4. Compounds according to Embodiment 22D1, wherein
$R_{25}$ is $C_1$-$C_4$ alkyl or $NR_{26}R_{27}$; and $R_{26}$, $R_{27}$ and the nitrogen to which they are attached represent pyrrolidinyl, piperidinyl, piperazinyl, morpholinyl, or imidazolidinyl;
$R_5$ is H, $C_1$-$C_4$ alkoxy, $CF_3$, $CO_2H$, $C_1$-$C_4$ alkoxycarbonyl;
$R_6$ is H, $C_1$-$C_4$ alkoxy, halogen, $C_1$-$C_4$ alkyl, $CF_3$, $OCF_3$, $CO_2H$, $C_1$-$C_4$ alkoxycarbonyl, CN, or $C_2$-$C_6$ alkenyl;
$R_8$ is H, halogen, $C_1$-$C_4$ alkoxy, $C_1$-$C_4$ alkyl, —S(O)$_x$—$R_{25}$, or —($C_1$-$C_4$ alkyl)-S(O)$_x$—$R_{25}$; and
$R_9$ is H, halogen, $C_1$-$C_3$ alkoxy, or $C_1$-$C_3$ alkyl.

Embodiment 22E. Compounds according to Embodiment 22D, wherein $R_7$ is H, OH, $C_1$-$C_4$ alkoxy, halogen, $C_1$-$C_4$ alkyl, $CF_3$, $CO_2H$, —C(O)$NR_{30}R_{31}$, or $C_1$-$C_4$ alkoxycarbonyl; and $R_{30}$ and $R_{31}$ are independently H or $C_1$-$C_6$ alkyl.

Embodiment 22F. Compounds according to Embodiment 22E, wherein $R_7$ is H, OH, methoxy, halogen, methyl, $CF_3$, $CO_2H$, —C(O) $NR_{30}R_{31}$, or $C_1$-$C_2$ alkoxycarbonyl; and $R_{30}$ and $R_{31}$ are independently H or $C_1$-$C_4$ alkyl.

Embodiment 22G. Compounds according to Embodiment 22F, wherein $R_7$ is $CO_2H$, —C(O)$NR_{30}R_{31}$, or $C_1$-$C_2$ alkoxycarbonyl.

Embodiment 22H. Compounds according to Embodiment 22F, wherein $R_7$ is OH, methoxy, halogen, methyl, or $CF_3$.

Embodiment 22I. Compounds according to any one of Embodiments 22E, 22F, 22G or 22H, wherein $R_3$ is H, or halogen; $R_4$ is halogen, methyl, $CF_3$, or methoxy; and $R_{3'}$ is H or halogen.

Embodiment 22J. Compounds according to Embodiment 22I, wherein $R_5$ is H, methoxy, $CF_3$, $CO_2H$, $C_1$-$C_2$ alkoxycarbonyl, —C(O)$NH_2$, —C(O)NH($C_1$-$C_4$)alkyl, or —C(O)N($C_1$-$C_4$)alkyl($C_1$-$C_4$)alkyl;
$R_6$ is H, $C_1$-$C_2$ alkoxy, halogen, $C_1$-$C_2$ alkyl, $CF_3$, $OCF_3$, $CO_2H$, $C_1$-$C_2$ alkoxycarbonyl, —C(O)$NH_2$, —C(O)NH ($C_1$-$C_4$)alkyl, or —C(O)N($C_1$-$C_4$)alkyl($C_1$-$C_4$) alkyl;
$R_8$ is H or halogen (preferred halogens are F or Cl); and
$R_9$ is H or halogen (preferred halogens are F or Cl).

Embodiment 22K. Compounds according to Embodiment 22J wherein $R_3$ is H; $R_4$ is halogen (preferably F or Cl, more preferably Cl); and $R_{3'}$ is H. In another aspect, $R_4$ is methyl. In still another aspect, $R_4$ is $CF_3$. In yet another aspect, $R_4$ is Cl.

Embodiment 22L. Compounds according to Embodiment 22K, wherein $R_5$ is H, methoxy, $CF_3$, $CO_2H$, or $C_1$-$C_2$ alkoxycarbonyl; $R_6$ is H, methoxy, halogen, methyl, $CF_3$, $OCF_3$, $CO_2H$, or $C_1$-$C_2$ alkoxycarbonyl (in one aspect, $C_2$ alkoxycarbonyl); $R_8$ is H, F or Cl; and $R_9$ is H, F or Cl.

Embodiment 22M. Compounds according to Embodiment 22C, wherein $R_7$ is H, —NHR', —NR'R" or —N($R_{16}$)C(O)—$R_{17}$; $R_{16}$ is H or $C_1$-$C_4$ alkyl; $R_{17}$ is $C_1$-$C_6$ alkyl, phenyl, pyridyl, pyrimidyl, pyridazyl, pyrazinyl, thienyl, $C_1$-$C_6$ alkoxy, phenyloxy, pyridyloxy, pyrimidyloxy, pyridazyloxy, pyrazinyloxy, thienyloxy, phenyl($C_1$-$C_4$)alkoxy, or —$NR_{18}R_{19}$; and $R_8$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$) alkyl; wherein R' is H, $C_1$-$C_4$ alkyl, or $C_1$-$C_4$ alkanoyl; R" is $C_1$-$C_4$ alkyl, wherein the alkyl group is optionally substituted with halogen.

Embodiment 22N. Compounds according to Embodiment 22M, wherein $R_3$ is H, or halogen; $R_4$ is halogen, methyl, $CF_3$, or methoxy; and $R_{3'}$ is H or halogen. In another aspect, $R_4$ is methyl. In still another aspect, $R_4$ is $CF_3$. In yet another aspect, $R_4$ is Cl.

Embodiment 22O. Compounds according to Embodiment 22N, wherein $R_5$ is H, methoxy, $CF_3$, $CO_2H$, $C_1$-$C_2$ alkoxycarbonyl, —C(O)$NH_2$, —C(O)NH($C_1$-$C_4$) alkyl, or —C(O)N($C_1$-$C_4$)alkyl($C_1$-$C_4$)alkyl; $R_6$ is H, $C_1$-$C_2$ alkoxy, halogen, $C_1$-$C_2$ alkyl, $CF_3$, $OCF_3$, $CO_2H$, $C_1$-$C_2$ alkoxycarbonyl, —C(O)$NH_2$, —C(O)NH($C_1$-$C_4$) alkyl, or —C(O)N($C_1$-$C_4$) alkyl($C_1$-$C_4$)alkyl; $R_8$ is H or halogen (preferred halogens are F or Cl); and $R_9$ is H or halogen (preferred halogens are F or Cl).

Embodiment 22P. Compounds according to Embodiment 22O wherein $R_3$ is H; $R_4$ is halogen (preferably F or Cl, more preferably Cl), methyl, or $CF_3$; and $R_{3'}$ is H.

Embodiment 22Q. Compounds according to Embodiment 22P, wherein $R_5$ is H, methoxy, $CF_3$, $CO_2H$, or $C_1$-$C_2$ alkoxycarbonyl;
$R_6$ is H, methoxy, halogen, methyl, $CF_3$, $OCF_3$, $CO_2H$, or $C_1$-$C_2$ alkoxycarbonyl (in one aspect, $C_2$ alkoxycarbonyl);
$R_8$ is H, F or Cl; and
$R_9$ is H, F or Cl.

Embodiment 22R. Compounds according to any one of Embodiments 22N, 22O, 22P, or 22Q, wherein $R_7$ is H or —N($R_{16}$)C(O)—$R_{17}$; wherein $R_{16}$ is H or $C_1$-$C_4$ alkyl; $R_{17}$ is $C_1$-$C_6$ alkyl, phenyl, pyridyl, pyrimidyl, pyridazyl, pyrazinyl, thienyl, $C_1$-$C_6$ alkoxy, phenyloxy, pyridyloxy, pyrimidyloxy, pyridazyloxy, pyrazinyloxy, thienyloxy, phenyl($C_1$-$C_4$) alkoxy, or —$NR_{18}R_{19}$; and $R_{18}$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$) alkyl.

Embodiment 22S. Compounds according to Embodiment 22R, wherein $R_{17}$ is $C_1$-$C_4$ alkyl, phenyl, pyridyl, pyrimidyl, pyridazyl, pyrazinyl, thienyl, $C_1$-$C_4$ alkoxy, phenyloxy, pyridyloxy, pyrimidyloxy, pyridazyloxy, pyrazinyloxy, thienyloxy, phenyl($C_1$-$C_4$) alkoxy.

Embodiment 22T. Compounds according to Embodiment 22S, wherein $R_{17}$ is $C_1$-$C_4$ alkyl, $C_1$-$C_4$ alkoxy, phenyl, phenyloxy, or phenyl($C_1$-$C_2$) alkoxy.

Embodiment 22U. Compounds according to Embodiment 22S, wherein $R_{17}$ is pyridyl, pyrimidyl, pyridazyl, pyrazinyl, thienyl, pyridyloxy, pyrimidyloxy, pyridazyloxy, pyrazinyloxy, or thienyloxy.

Embodiment 22V. Compounds according to Embodiment 22R, wherein $R_{17}$ is —$NR_{18}R_{19}$; and $R_{18}$ and $R_{19}$ are independently H, $C_1$-$C_6$ alkyl, phenyl, pyridyl, thienyl, piperidinyl, pyrrolidinyl, morpholinyl, thiomorpholinyl, thiomorpholinyl 1,1-dioxide, tetrahydro-thiopyranyl 1,1-dioxide, or phenyl($C_1$-$C_4$) alkyl.

Embodiment 22W. Compounds according to Embodiment 22V, wherein $R_{17}$ is —$NR_{18}R_{19}$; and $R_{18}$ and $R_{19}$ are independently H, $C_1$-$C_6$ alkyl, phenyl, pyridyl, thienyl, piperidinyl, pyrrolidinyl, morpholinyl, or phenyl($C_1$-$C_4$) alkyl.

Embodiment 22X. Compounds according to Embodiment 22W, wherein $R_{18}$ and $R_{19}$ are independently H, $C_1$-$C_4$ alkyl, phenyl, or phenyl($C_1$-$C_2$) alkyl.

Embodiment 22Y. Compounds according to Embodiment 22V, wherein $R_{18}$ and $R_{19}$ are independently H, pyridyl, thienyl, piperidinyl, pyrrolidinyl, morpholinyl, thiomorpholinyl, thiomorpholinyl 1,1-dioxide, or tetrahydro-thiopyranyl 1,1-dioxide. In another aspect, one of $R_{18}$ and $R_{19}$ is H.

Embodiment 22Z. Compounds according to Embodiment 22V, wherein $R_{18}$ and $R_{19}$ are independently H, pyridyl, piperidinyl, pyrrolidinyl, or morpholinyl. In another aspect, one of $R_{18}$ and $R_{19}$ is H. In another aspect, only one of $R_{18}$ and $R_{19}$ is H.

Embodiment 22AA. Compounds according to Embodiment 21V, wherein $R_{18}$ and $R_{19}$ are independently H, thienyl, thiomorpholinyl, thiomorpholinyl 1,1-dioxide, or tetrahydro-thiopyranyl 1,1-dioxide. In another aspect, one of $R_{18}$ and $R_{19}$ is H. In another aspect, only one of $R_{18}$ and $R_{19}$ is H.

Embodiment 22BB. Compounds according to any one of Embodiments 22I, 22J, 22K, or 22L, wherein $R_7$ is H, —NHR', or —NR'R"; wherein R' is H, $C_1$-$C_4$ alkyl, or $C_1$-$C_4$ alkanoyl; R" is $C_1$-$C_4$ alkyl, wherein the alkyl group is optionally substituted with halogen.

Embodiment 22CC. Compounds according to Embodiment 22D, wherein $R_7$ is thiazolyl($C_1$-$C_4$)alkoxy, pyridyl($C_1$-$C_4$)alkoxy, oxazolyl($C_1$-$C_4$)alkoxy, pyrazolyl($C_1$-$C_4$) alkoxy, wherein the thiazolyl, pyridyl, oxazolyl, and pyrazolyl groups are optionally substituted with 1, 2, or 3 groups that are independently $C_1$-$C_4$ alkyl, $C_1$-$C_4$ alkoxy, or halogen.

Embodiment 22DD. Compounds according to Embodiment 21CC, wherein $R_7$ is thiazolyl($C_1$-$C_2$)alkoxy, pyridyl ($C_1$-$C_2$)alkoxy, oxazolyl($C_1$-$C_2$)alkoxy, or pyrazolyl($C_1$-$C_2$) alkoxy, wherein the thiazolyl, pyridyl, oxazolyl, and pyrazolyl groups are optionally substituted with 1, or 2 groups that are independently methyl, methoxy, or halogen.

Embodiment 22EE. Compounds according to Embodiment 22D, wherein $R_7$ is phenyl optionally substituted with 1, 2, 3, 4 or 5 groups that are independently halogen, $C_1$-$C_4$ alkyl, $C_1$-$C_4$ alkoxy, $OCF_3$, CN, $CO_2H$, $C_1$-$C_4$ alkoxycarbonyl, $C(O)NH_2$, —$C(O)NH(C_1$-$C_4)$ alkyl, —$C(O)N(C_1$-$C_4)$ alkyl($C_1$-$C_4$)alkyl, or $C_1$-$C_4$ thioalkoxy. In another aspect, the phenyl is optionally substituted with 1, 2, or 3 groups, which are independently halogen, $C_1$-$C_4$ alkyl, $C_1$-$C_4$ alkoxy, $OCF_3$, CN, $CO_2H$, $C_1$-$C_4$ alkoxycarbonyl, $C(O)NH_2$, —$C(O)NH$ ($C_1$-$C_4$)alkyl, or —$C(O)N(C_1$-$C_4)$alkyl($C_1$-$C_4$)alkyl.

Embodiment 22FF. Compounds according to Embodiment 22D, wherein $R_7$ is phenyl optionally substituted with 1, 2, or 3 groups that are independently halogen, $C_1$-$C_2$ alkyl, $C_1$-$C_2$ alkoxy, $OCF_3$, CN, $CO_2H$, $C_1$-$C_2$ alkoxycarbonyl, $C(O)NH_2$, —$C(O)NH(C_1$-$C_4)$ alkyl, or —$C(O)N(C_1$-$C_4)$alkyl($C_1$-$C_4$) alkyl. In another aspect, the phenyl is optionally substituted with 1 or 2 groups, which are independently halogen, methyl, methoxy, $CO_2H$, $C_1$-$C_2$ alkoxycarbonyl, $C(O)NH_2$, —$C(O)NH(C_1$-$C_4)$alkyl, or —$C(O)N(C_1$-$C_4)$alkyl($C_1$-$C_4$) alkyl.

Embodiment 22GG. Compounds according to Embodiment 22, wherein $R_5$, $R_6$, and the carbons to which they are attached form a phenyl ring, which is optionally substituted with 1 or 2 groups that are independently halogen, $C_1$-$C_4$ alkyl, $C_1$-$C_4$ alkoxy, $CF_3$, or $OCF_3$; and $R_7$, $R_8$, and $R_9$ are H.

Embodiment 22HH. Compounds according to Embodiment 22, wherein $R_5$, $R_8$, and $R_9$ are H; and $R_6$, $R_7$, and the carbons to which they are attached form a phenyl ring, which is optionally substituted with 1 or 2 groups that are independently halogen, $C_1$-$C_4$ alkyl, $C_1$-$C_4$ alkoxy, $CF_3$, or $OCF_3$.

Embodiment 22II. Compounds according to Embodiment 22, wherein $R_5$, $R_6$, and $R_9$ are H; and $R_7$ and $R_8$ are —O—$CH_2CH_2$—O—, or —O—$CH_2$—O—.

Embodiment 22JJ. Compounds according to Embodiment 22, wherein $R_5$, $R_6$, and $R_9$ are H; and $R_7$ and $R_8$ are —O—$CH_2CH_2$—O—.

Embodiment 22KK. Compounds according to Embodiment 22, wherein $R_5$, $R_6$, and $R_9$ are H; and $R_7$ and $R_8$ are —O—$CH_2$—O—.

Embodiment 22LL. Compounds according to any one of Embodiments 22GG, 22HH, 22II, 22JJ, or 22KK wherein $R_3$ is H, halogen, methyl, methoxy, $CF_3$, or CN; $R_4$ is halogen, methoxy, methyl, $CF_3$, $OCF_3$, or CN; $R_{3'}$ is H, or halogen.

Embodiment 22MM. Compounds according to Embodiment 22LL, wherein $R_3$ is H, or halogen (in one aspect F or Cl); $R_4$ is halogen (in one aspect F or Cl), methyl, $CF_3$, or methoxy; and $R_{3'}$ is H or halogen (in one aspect F or Cl). In another aspect, $R_4$ is methyl. In still another aspect, $R_4$ is $CF_3$. In yet another aspect, $R_4$ is Cl.

Embodiment 22NN. Compounds according to any one of Embodiments 22A, 22B, 22C, 22D, 22D1, 22D2, 22D3, 22D4, 22E, 22F, 22G, 22H, 22I, 22J, 22K, 22L, 22M, 22N, 22O, 22P, 22Q, 22R, 22S, 22T, 22U, 22V, 22X, 22Y, 22Z, 22AA, 22BB, 22CC, 22DD, 22EE, 22FF, 22GG, 22HH, 22II, 22JJ, 22KK, 22LL, or 22MM wherein $R_{50}$ is H, methyl, ethyl, n-propyl, isopropyl, sec-butyl, or isobutyl; and $R_{55}$ is H, methyl, ethyl or cyclopropyl.

Embodiment 22OO. Compounds according to Embodiment 22NN, wherein $R_{55}$ is H.

Embodiment 22PP. Compounds according to Embodiment 22NN, wherein $R_{50}$ is methyl, ethyl, or n-propyl.

Embodiment 22RR. Compounds according to Embodiment 22NN, wherein $R_{50}$ is isopropyl, sec-butyl, or isobutyl.

Embodiment 22SS. Compounds according to Embodiment 22NN, wherein $R_{50}$ is n-propyl, isopropyl, or isobutyl.

Embodiment 22TT. Compounds according to Embodiment 22NN, wherein $R_{55}$ is methyl.

Embodiment 22UU. Compounds according to Embodiment 22NN, wherein $R_{50}$ is methyl, ethyl, or n-propyl.

Embodiment 22VV. Compounds according to Embodiment 22NN, wherein $R_{50}$ is isopropyl, sec-butyl, or isobutyl.

Embodiment 22WW. Compounds according to Embodiment 22NN, wherein $R_{50}$ is n-propyl, isopropyl, or isobutyl.

Embodiment 22XX. Compounds according to Embodiment 22NN, wherein $R_{55}$ is ethyl.

Embodiment 22YY. Compounds according to Embodiment 22NN, wherein $R_{50}$ is methyl, ethyl, or n-propyl.

Embodiment 22ZZ. Compounds according to Embodiment 22NN, wherein $R_{50}$ is isopropyl, sec-butyl, or isobutyl.

Embodiment 22AAA. Compounds according to Embodiment 22NN, wherein $R_{50}$ is n-propyl, isopropyl, or isobutyl.

Embodiment 22BBB. Compounds according to Embodiment 22NN, wherein $R_{55}$ is cyclopropyl.

Embodiment 22CCC. Compounds according to Embodiment 22NN, wherein $R_{50}$ is methyl, ethyl, or n-propyl.

Embodiment 22DDD. Compounds according to Embodiment 22NN, wherein $R_{50}$ is isopropyl, sec-butyl, or isobutyl.

Embodiment 22EEE. Compounds according to Embodiment 22NN, wherein $R_{50}$ is n-propyl, isopropyl, or isobutyl.

Embodiment 22FFF. Compounds according to Embodiment 22N of the formula:

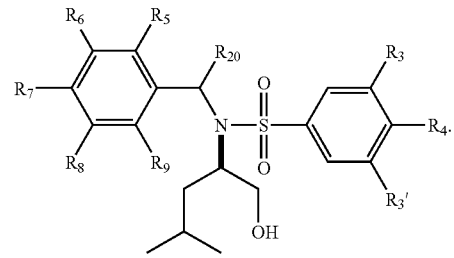

Embodiment 22GGG. Compounds according to Embodiment 22M, wherein $R_5$, $R_9$, $R_3$ and $R_{3'}$ are H.

Embodiment 22HHH. Compounds according to Embodiment 22N, wherein $R_4$ is halogen (in one aspect, F or Cl), methyl, or $CF_3$. In another aspect, $R_4$ is methyl. In still another aspect, $R_4$ is $CF_3$. In yet another aspect, $R_4$ is Cl.

In embodiment 23, the invention provides pharmaceutical compositions comprising at least one compound of Formula 1 and at least one pharmaceutically acceptable carrier, solvent, adjuvant or excipient, or a combination thereof.

In embodiment 24, the invention provides a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, age related macular degeneration, or diffuse Lewy body type of Alzheimer's disease and who is in need of such treatment which comprises administration of a therapeutically effective amount of at least one compound of Formula I.

The following list is presented to give the reader an understanding of the compounds that are encompassed within the invention.

(S)-4-chloro-N-cinnamyl-N-(1-hydroxy-4-methylpentan-2-yl)benzenesulfonamide;
[(4-Chloro-benzenesulfonyl)-methyl-amino]-acetic acid ethyl ester;
[2-(4-Chloro-benzenesulfonylimino)-imidazolidin-1-yl]-acetic acid;
2-(4-Chloro-benzenesulfonylamino)-N-methyl-propionamide;
2-[(4-Chloro-benzenesulfonyl)-(3,4-dimethoxy-benzyl)-amino]-3-phenyl-propionamide;
2-[(4-Chloro-benzenesulfonyl)-(3-phenyl-propyl)-amino]-3-hydroxy-N-methyl-butyramide;
3-[(4-Chloro-benzenesulfonyl)-(3,4-dimethoxy-benzyl)-amino]-piperidine-1-carboxylic acid tert-butyl ester;
4-Chloro-N-(1,2-dimethyl-propyl)-N-(3-phenyl-allyl)-benzenesulfonamide;
4-Chloro-N-(1,2-dimethyl-propyl)-N-(3-phenyl-propyl)-benzenesulfonamide;
4-Chloro-N-(1,3-dimethyl-butyl)-N-(3-phenyl-allyl)-benzenesulfonamide;
4-Chloro-N-(1,3-dimethyl-butyl)-N-(3-phenyl-propyl)-benzenesulfonamide;
4-Chloro-N-(1-chloro-3,4-dihydro-naphthalen-2-ylmethyl)-N-(1-hydroxymethyl-3-methyl-butyl)-benzenesulfonamide;
4-Chloro-N-(1-ethyl-propyl)-N-(3-phenyl-allyl)-benzenesulfonamide;
4-Chloro-N-(l-ethyl-propyl)-N-(3-phenyl-propyl)-benzenesulfonamide;
4-Chloro-N-(1-hydroxymethyl-3-methyl-butyl)-N-(1,2,3,4-tetrahydro-naphthalen-2-yl)-benzenesulfonamide;
4-Chloro-N-(1-hydroxymethyl-3-methyl-butyl)-N-(1-methyl-1H-indol-2-ylmethyl)-benzenesulfonamide;
4-Chloro-N-(1-hydroxymethyl-3-methyl-butyl)-N-(1-methyl-3-phenyl-allyl)-benzenesulfonamide;
4-Chloro-N-(1-hydroxymethyl-3-methyl-butyl)-N-(1-methyl-3-phenyl-propyl)-benzenesulfonamide;
4-Chloro-N-(1-hydroxymethyl-3-methyl-butyl)-N-(2-methyl-3-phenyl-allyl)-benzenesulfonamide;
4-Chloro-N-(1-hydroxymethyl-3-methyl-butyl)-N-(2-pentyl-3-phenyl-allyl)-benzenesulfonamide;
4-Chloro-N-(1-hydroxymethyl-3-methyl-butyl)-N-(3-phenyl-butyl)-benzenesulfonamide;
4-Chloro-N-(1-hydroxymethyl-3-methyl-butyl)-N-(3-phenyl-propyl)-benzenesulfonamide;
4-Chloro-N-(1-hydroxymethyl-3-methyl-butyl)-N-(4-methoxy-benzyl)-benzenesulfonamide;
4-Chloro-N-(1-hydroxymethyl-3-methyl-butyl)-N-[3-(2-methoxy-phenyl)-allyl]-benzenesulfonamide;
4-Chloro-N-(1-hydroxymethyl-3-methyl-butyl)-N-{3-methoxy-4-[2-(4-methyl-thiazol-5-yl)-ethoxy]-benzyl}-benzenesulfonamide;
4-Chloro-N-(1-hydroxymethyl-3-methyl-butyl)-N-methyl-benzenesulfonamide;
4-Chloro-N-(1-hydroxymethyl-3-methyl-butyl)-N-propyl-benzenesulfonamide;
4-Chloro-N-(1-hydroxymethyl-pentyl)-N-{3-methoxy-4-[2-(4-methyl-thiazol-5-yl)-ethoxy]-benzyl}-benzenesulfonamide;
4-Chloro-N-(1-hydroxymethyl-pentyl)-N-{3-methoxy-4-[2-(4-methyl-thiazol-5-yl)-ethoxy]-benzyl}-benzenesulfonamide;
4-Chloro-N-(1-hydroxymethyl-propyl)-N-(3-phenyl-allyl)-benzenesulfonamide;
4-Chloro-N-(1-hydroxymethyl-propyl)-N-(3-phenyl-propyl)-benzenesulfonamide;
4-Chloro-N-(1-methyl-butyl)-N-(3-phenyl-allyl)-benzenesulfonamide;
4-Chloro-N-(1-methyl-butyl)-N-(3-phenyl-propyl)-benzenesulfonamide;
4-chloro-N-(2,3-dihydro-1,4-benzodioxin-6-ylmethyl)-N-[(1 S)-1-(hydroxymethyl)-3-methylbutyl]benzenesulfonamide;
4-Chloro-N-(2,3-dihydro-benzo[1,4]dioxin-6-ylmethyl)-N-(1-hydroxymethyl-3-methyl-butyl)-benzenesulfonamide;
4-Chloro-N-(2,3-dihydroxy-propyl)-N-{3-methoxy-4-[2-(4-methyl-thiazol-5-yl)-ethoxy]-benzyl}-benzenesulfonamide;
4-Chloro-N-(2,3-dihydroxy-propyl)-N-{3-methoxy-4-[2-(4-methyl-thiazol-5-yl)-ethoxy]-benzyl}-benzenesulfonamide;
4-Chloro-N-(2,4-dichloro-benzyl)-N-{3-methoxy-4-[2-(4-methyl-thiazol-5-yl)-ethoxy]-benzyl}-benzenesulfonamide;
4-Chloro-N-(2,4-dichloro-benzyl)-N-{3-methoxy-4-[2-(4-methyl-thiazol-5-yl)-ethoxy]-benzyl}-benzenesulfonamide;
4-Chloro-N-(2,4-difluoro-benzyl)-N-(1-hydroxymethyl-3-methyl-butyl)-benzenesulfonamide;
4-chloro-N-(2,4-difluorobenzyl)-N-[(1R)-1-(hydroxymethyl)-3-methyl-butyl]benzenesulfonamide;
4-Chloro-N-(2-cyano-ethyl)-N-cyclopropyl-benzenesulfonamide;
4-Chloro-N-(2-cyano-ethyl)-N-cyclopropyl-benzenesulfonamide;
4-Chloro-N-(2-cyano-ethyl)-N-ethyl-benzenesulfonamide;
4-Chloro-N-(2-cyano-ethyl)-N-ethyl-benzenesulfonamide;
4-Chloro-N-(2-hydroxy-1-methyl-2-phenyl-ethyl)-N-methyl-benzenesulfonamide;
4-Chloro-N-(2-hydroxy-1-methyl-2-phenyl-ethyl)-N-methyl-benzenesulfonamide;
4-Chloro-N-(2-hydroxy-1-methyl-2-phenyl-ethyl)-N-methyl-benzenesulfonamide;
4-Chloro-N-(2-hydroxy-1-methyl-2-phenyl-ethyl)-N-methyl-benzenesulfonamide;
4-Chloro-N-(2-hydroxy-cyclohexylmethyl)-N-{3-methoxy-4-[2-(4-methyl-thiazol-5-yl)-ethoxy]-benzyl}-benzenesulfonamide;
4-Chloro-N-(2-hydroxy-propyl)-N-(3-phenyl-allyl)-benzenesulfonamide;
4-Chloro-N-(2-hydroxy-propyl)-N-(3-phenyl-propyl)-benzenesulfonamide;

4-Chloro-N-(2-hydroxy-propyl)-N-{3-methoxy-4-[2-(4-methyl-thiazol-5-yl)-ethoxy]-benzyl}-benzenesulfonamide;

4-Chloro-N-(2-hydroxy-propyl)-N-{3-methoxy-4-[2-(4-methyl-thiazol-5-yl)-ethoxy]-benzyl}-benzenesulfonamide;

4-Chloro-N-(2-methoxy-1-methyl-ethyl)-N-(3-phenyl-allyl)-benzenesulfonamide;

4-Chloro-N-(2-methoxy-1-methyl-ethyl)-N-(3-phenyl-propyl)-benzenesulfonamide;

4-Chloro-N-(2-methyl-cyclohexyl)-N-(3-phenyl-allyl)-benzenesulfonamide;

4-Chloro-N-(2-methyl-cyclohexyl)-N-(3-phenyl-propyl)-benzenesulfonamide;

4-Chloro-N-(3,4-dimethoxy-benzyl)-N-(1-hydroxymethyl-2-methyl-propyl)-benzenesulfonamide;

4-Chloro-N-(3,4-dimethoxy-benzyl)-N-(1-hydroxymethyl-2-methyl-propyl)-benzenesulfonamide;

4-Chloro-N-(3,4-dimethoxy-benzyl)-N-(1-hydroxymethyl-2-phenyl-ethyl)-benzenesulfonamide;

4-Chloro-N-(3,4-dimethoxy-benzyl)-N-(1-hydroxymethyl-2-phenyl-ethyl)-benzenesulfonamide;

4-Chloro-N-(3,4-dimethoxy-benzyl)-N-(1-hydroxymethyl-3-methyl-butyl)-benzenesulfonamide;

4-Chloro-N-(3,4-dimethoxy-benzyl)-N-(1-hydroxymethyl-propyl)-benzenesulfonamide;

4-Chloro-N-(3,4-dimethoxy-benzyl)-N-(1-naphthalen-1-yl-ethyl)-benzenesulfonamide;

4-Chloro-N-(3,4-dimethoxy-benzyl)-N-(1-naphthalen-1-yl-ethyl)-benzenesulfonamide;

4-Chloro-N-(3,4-dimethoxy-benzyl)-N-(1-phenyl-4,5-dihydro-1H-pyrazol-3-yl)-benzenesulfonamide;

4-Chloro-N-(3,4-dimethoxy-benzyl)-N-(1-phenyl-4,5-dihydro-1H-pyrazol-3-yl)-benzenesulfonamide;

4-Chloro-N-(3,4-dimethoxy-benzyl)-N-(1-phenyl-ethyl)-benzenesulfonamide;

4-Chloro-N-(3,4-dimethoxy-benzyl)-N-(1-phenyl-ethyl)-benzenesulfonamide;

4-Chloro-N-(3,4-dimethoxy-benzyl)-N-(2,3-dimethyl-cyclohexyl)-benzenesulfonamide;

4-Chloro-N-(3,4-dimethoxy-benzyl)-N-(2,3-dimethyl-cyclohexyl)-benzenesulfonamide;

4-Chloro-N-(3,4-dimethoxy-benzyl)-N-(2-hydroxy-1-hydroxymethyl-2-phenyl-ethyl)-benzenesulfonamide;

4-Chloro-N-(3,4-dimethoxy-benzyl)-N-(2-hydroxy-1-methyl-2-phenyl-ethyl)-benzenesulfonamide;

4-Chloro-N-(3,4-dimethoxy-benzyl)-N-(2-hydroxy-1-phenyl-ethyl)-benzenesulfonamide;

4-Chloro-N-(3,4-dimethoxy-benzyl)-N-(2-methyl-cyclohexyl)-benzenesulfonamide;

4-Chloro-N-(3,4-dimethoxy-benzyl)-N-(3-hydroxy-2,2-dimethyl-propyl)-benzenesulfonamide;

4-Chloro-N-(3,4-dimethoxy-benzyl)-N-(3-hydroxymethyl-bicyclo[2.2.1]hept-2-yl)-benzenesulfonamide;

4-Chloro-N-(3,4-dimethoxy-benzyl)-N-(4-methyl-cyclohexyl)-benzenesulfonamide;

4-chloro-N-(3,4-dimethoxybenzyl)-N-[(1R,2S)-2-hydroxy-1-(hydroxymethyl)-2-phenylethyl]benzenesulfonamide;

4-chloro-N-(3,4-dimethoxybenzyl)-N-[(1S)-1-(hydroxymethyl)-3-methylbutyl]benzenesulfonamide;

4-chloro-N-(3,4-dimethoxybenzyl)-N-[(1S)-1-(hydroxymethyl)propyl]benzenesulfonamide;

4-chloro-N-(3,4-dimethoxybenzyl)-N-[(1S)-2-hydroxy-1-phenylethyl]benzenesulfonamide;

4-chloro-N-(3,4-dimethoxybenzyl)-N-[(1S,2R)-2-hydroxy-1-methyl-2-phenylethyl]benzenesulfonamide;

4-chloro-N-(3,4-dimethoxybenzyl)-N-[(1S,3R,4R)-3-(hydroxymethyl)bicyclo[2.2.1]hept-2-yl]benzenesulfonamide;

4-Chloro-N-(3,4-dimethoxy-benzyl)-N-[1-(4-methanesulfonyl-phenyl)-ethyl]-benzenesulfonamide;

4-Chloro-N-(3,4-dimethoxy-benzyl)-N-[1-(4-methanesulfonyl-phenyl)-ethyl]-benzenesulfonamide;

4-Chloro-N-(3-fluoro-4-methoxy-benzyl)-N-(1-hydroxymethyl-3-methyl-butyl)-benzenesulfonamide;

4-chloro-N-(3-fluoro-4-methoxybenzyl)-N-[(1S)-1-(hydroxymethyl)-3-methylbutyl]benzenesulfonamide;

4-Chloro-N-(3-hydroxy-butyl)-N-{3-methoxy-4-[2-(4-methyl-thiazol-5-yl)-ethoxy]-benzyl}-benzenesulfonamide;

4-Chloro-N-(4-chloro-6-fluoro-2H-chromen-3-ylmethyl)-N-(1-hydroxymethyl-3-methyl-butyl)-benzenesulfonamide;

4-Chloro-N-(4-chloro-benzyl)-N-(1-hydroxymethyl-3-methyl-butyl)-benzenesulfonamide;

4-chloro-N-(4-chlorobenzyl)-N-[(1R)-1-(hydroxymethyl)-3-methylbutyl]benzenesulfonamide;

4-Chloro-N-(4-diethylamino-1-methyl-butyl)-N-(3,4-dimethoxy-benzyl)-benzenesulfonamide;

4-Chloro-N,N-dicyclohexyl-benzenesulfonamide;

4-Chloro-N,N-diisopropyl-benzenesulfonamide;

4-Chloro-N,N-divinyl-benzenesulfonamide;

4-chloro-N-[(1R)-1-(hydroxymethyl)-3-methylbutyl]-N-(3-phenylpropyl)benzenesulfonamide;

4-chloro-N-[(1R)-1-(hydroxymethyl)-3-methylbutyl]-N-(4-methoxybenzyl)benzenesulfonamide;

4-chloro-N-[(1R,2S)-2-hydroxy-1-methyl-2-phenylethyl]-N-methylbenzenesulfonamide;

4-chloro-N-[(1S)-1-(hydroxymethyl)-3-methylbutyl]-N-[(2E)-2-methyl-3-phenylprop-2-en-1-yl]benzenesulfonamide;

4-chloro-N-[(1S)-1-(hydroxymethyl)-3-methylbutyl]-N-[(2E)-3-phenylprop-2-en-1-yl]benzenesulfonamide;

4-chloro-N-[(1S)-1-(hydroxymethyl)-3-methylbutyl]-N-{3-methoxy-4-[2-(4-methyl-1,3-thiazol-5-yl)ethoxy]benzyl}benzenesulfonamide;

4-chloro-N-[(1S,2S)-2-hydroxy-1-methyl-2-phenylethyl]-N-methylbenzenesulfonamide;

4-Chloro-N-[2-(3,4-dihydroxy-phenyl)-2-oxo-ethyl]-N-methylbenzenesulfonamide;

4-chloro-N-{[(1R,2S)-2-hydroxycyclohexyl]methyl}-N-{3-methoxy-4-[2-(4-methyl-1,3-thiazol-5-yl)ethoxy]benzyl}benzenesulfonamide;

4-Chloro-N-{3-methoxy-4-[2-(4-methyl-thiazol-5-yl)-ethoxy]-benzyl}-N-(2-methyl-cyclohexyl)-benzenesulfonamide;

4-Chloro-N-{3-methoxy-4-[2-(4-methyl-thiazol-5-yl)-ethoxy]-benzyl}-N-(2-methyl-butyl)-benzenesulfonamide;

4-Chloro-N-{3-methoxy-4-[2-(4-methyl-thiazol-5-yl)-ethoxy]-benzyl}-N-(3-methylsulfanyl-propyl)-benzenesulfonamide;

4-Chloro-N-{3-methoxy-4-[2-(4-methyl-thiazol-5-yl)-ethoxy]-benzyl}-N-(4-methyl-cyclohexyl)-benzenesulfonamide;

4-Chloro-N-{3-methoxy-4-[2-(4-methyl-thiazol-5-yl)-ethoxy]-benzyl}-N-pyridin-2-ylmethyl-benzenesulfonamide;

4-Chloro-N-{3-methoxy-4-[2-(4-methyl-thiazol-5-yl)-ethoxy]-benzyl}-N-prop-2-ynyl-benzenesulfonamide;

4-Chloro-N-{3-methoxy-4-[2-(4-methyl-thiazol-5-yl)-ethoxy]-benzyl}-N-(3-methyl-butyl)-benzenesulfonamide;

4-Chloro-N-{3-methoxy-4-[2-(4-methyl-thiazol-5-yl)-ethoxy]-benzyl}-N-(tetrahydro-furan-2-ylmethyl)-benzenesulfonamide;
4-Chloro-N-{3-methoxy-4-[2-(4-methyl-thiazol-5-yl)-ethoxy]-benzyl}-N-(3-methoxy-propyl)-benzenesulfonamide;
4-Chloro-N-{3-methoxy-4-[2-(4-methyl-thiazol-5-yl)-ethoxy]-benzyl}-N-(1-phenyl-ethyl)-benzenesulfonamide;
4-Chloro-N-{3-methoxy-4-[2-(4-methyl-thiazol-5-yl)-ethoxy]-benzyl}-N-(2-methyl-allyl)-benzenesulfonamide;
4-Chloro-N-{3-methoxy-4-[2-(4-methyl-thiazol-5-yl)-ethoxy]-benzyl}-N-(2-methyl-cyclohexyl)-benzenesulfonamide;
4-Chloro-N-{3-methoxy-4-[2-(4-methyl-thiazol-5-yl)-ethoxy]-benzyl}-N-(2-methyl-butyl)-benzenesulfonamide;
4-Chloro-N-{3-methoxy-4-[2-(4-methyl-thiazol-5-yl)-ethoxy]-benzyl}-N-(3-methylsulfanyl-propyl)-benzenesulfonamide;
4-Chloro-N-{3-methoxy-4-[2-(4-methyl-thiazol-5-yl)-ethoxy]-benzyl}-N-(4-methyl-cyclohexyl)-benzenesulfonamide;
4-Chloro-N-{3-methoxy-4-[2-(4-methyl-thiazol-5-yl)-ethoxy]-benzyl}-N-pyridin-2-ylmethyl-benzenesulfonamide;
4-Chloro-N-{3-methoxy-4-[2-(4-methyl-thiazol-5-yl)-ethoxy]-benzyl}-N-prop-2-ynyl-benzenesulfonamide;
4-Chloro-N-{3-methoxy-4-[2-(4-methyl-thiazol-5-yl)-ethoxy]-benzyl}-N-(3-methyl-butyl)-benzenesulfonamide;
4-Chloro-N-{3-methoxy-4-[2-(4-methyl-thiazol-5-yl)-ethoxy]-benzyl}-N-(tetrahydro-furan-2-ylmethyl)-benzenesulfonamide;
4-Chloro-N-{3-methoxy-4-[2-(4-methyl-thiazol-5-yl)-ethoxy]-benzyl}-N-(3-methoxy-propyl)-benzenesulfonamide;
4-Chloro-N-{3-methoxy-4-[2-(4-methyl-thiazol-5-yl)-ethoxy]-benzyl}-N-(1-phenyl-ethyl)-benzenesulfonamide;
4-Chloro-N-{3-methoxy-4-[2-(4-methyl-thiazol-5-yl)-ethoxy]-benzyl}-N-(2-methyl-allyl)-benzenesulfonamide;
4-Chloro-N-cyanomethyl-N-methyl-benzenesulfonamide;
4-Chloro-N-cyclohexyl-N-(2-hydroxy-ethyl)-benzenesulfonamide;
4-Chloro-N-cyclohexyl-N-(2-hydroxy-ethyl)-benzenesulfonamide;
4-Chloro-N-cyclohexyl-N-{3-methoxy-4-[2-(4-methyl-thiazol-5-yl)-ethoxy]-benzyl}-benzenesulfonamide;
4-Chloro-N-cyclohexyl-N-isopropyl-benzenesulfonamide;
4-Chloro-N-cyclooctyl-N-(3,4-dimethoxy-benzyl)-benzenesulfonamide;
4-Chloro-N-cyclopentyl-N-{3-methoxy-4-[2-(4-methyl-thiazol-5-yl)-ethoxy]-benzyl}-benzenesulfonamide;
4-Chloro-N-cyclopentyl-N-{3-methoxy-4-[2-(4-methyl-thiazol-5-yl)-ethoxy]-benzyl}-benzenesulfonamide;
4-Chloro-N-cyclopropylmethyl-N-(1-hydroxymethyl-3-methyl-butyl)-benzenesulfonamide;
4-Chloro-N-cyclopropylmethyl-N-{3-methoxy-4-[2-(4-methyl-thiazol-5-yl)-ethoxy]-benzyl}-benzenesulfonamide;
4-Chloro-N-cyclopropylmethyl-N-{3-methoxy-4-[2-(4-methyl-thiazol-5-yl)-ethoxy]-benzyl}-benzenesulfonamide;
4-Chloro-N-ethyl-N-(2-pyridin-2-yl-ethyl)-benzenesulfonamide;
4-Chloro-N-ethyl-N-[2-hydroxy-2-(3-hydroxy-phenyl)-ethyl]-benzenesulfonamide;
4-Chloro-N-ethyl-N-{3-methoxy-4-[2-(4-methyl-thiazol-5-yl)-ethoxy]-benzyl}-benzenesulfonamide;
4-Chloro-N-isopropyl-N-(2-pyridin-4-yl-ethyl)-benzenesulfonamide;
4-Chloro-N-methyl-N-(1-methyl-piperidin-4-yl)-benzenesulfonamide;
4-Chloro-N-methyl-N-(1-methyl-piperidin-4-yl)-benzenesulfonamide;
4-Chloro-N-methyl-N-(2-pyridin-4-yl-ethyl)-benzenesulfonamide;
4-Chloro-N-pyrrolidin-3-yl-benzenesulfonamide;
N-(1,3-benzodioxol-5-ylmethyl)-4-chloro-N-[(1S)-1-(hydroxymethyl)-3-methylbutyl]benzenesulfonamide;
N-(1-Benzyl-pyrrolidin-3-yl)-4-chloro-N-ethyl-benzenesulfonamide;
N-(2-Amino-benzyl)-4-chloro-N-{3-methoxy-4-[2-(4-methyl-thiazol-5-yl)-ethoxy]-benzyl}-benzenesulfonamide;
N-(2-Benzyl-cyclohexyl)-4-chloro-N-(1-hydroxymethyl-3-methyl-butyl)-benzenesulfonamide;
N-(4-Bromo-benzyl)-4-chloro-N-(1-hydroxymethyl-3-methyl-butyl)-benzenesulfonamide;
N-(4-bromobenzyl)-4-chloro-N-[(1R)-1-(hydroxymethyl)-3-methylbutyl]benzenesulfonamide;
N,N-Di-sec-butyl-4-chloro-benzenesulfonamide;
N-[(1R)-1-benzyl-2-hydroxyethyl]-4-chloro-N-(3,4-dimethoxybenzyl)benzenesulfonamide;
N-[(1S)-1-benzyl-2-hydroxyethyl]-4-chloro-N-(3,4-dimethoxybenzyl)benzenesulfonamide;
N-[(4-chlorophenyl)sulfonyl]-N-(3,4-dimethoxybenzyl)-L-phenylalaninamide;
N-[3-(4-tert-Butyl-phenyl)-2-methyl-propyl]-4-chloro-N-(1-hydroxymethyl-3-methyl-butyl)-benzenesulfonamide;
N2-[(4-chlorophenyl)sulfonyl]-N1-methyl-L-alaninamide;
N-Allyl-4-chloro-N-cyclohexyl-benzenesulfonamide;
N-Benzo[1,3]dioxol-5-ylmethyl-4-chloro-N-(1-hydroxyethyl-3-methyl-butyl)-benzenesulfonamide;
N-Benzofuran-2-ylmethyl-4-chloro-N-(1-hydroxymethyl-3-methyl-butyl)-benzenesulfonamide;
N-Benzofuran-2-ylmethyl-N-sec-butyl-4-chloro-benzenesulfonamide;
N-Benzyl-4-chloro-N-(1-hydroxymethyl-propyl)-benzenesulfonamide;
N-Benzyl-4-chloro-N-(2-hydroxy-cyclohexyl)-benzenesulfonamide;
N-Benzyl-4-chloro-N-(2-hydroxymethyl-cyclohexyl)-benzenesulfonamide;
N-benzyl-4-chloro-N-[(1R)-1-(hydroxymethyl)propyl]benzenesulfonamide;
N-benzyl-4-chloro-N-[(1S,2R)-2-(hydroxymethyl)cyclohexyl]benzenesulfonamide;
N-benzyl-4-chloro-N-[(1S,2S)-2-hydroxycyclohexyl]benzenesulfonamide;
N-Benzyl-N-sec-butyl-4-chloro-benzenesulfonamide;
N-sec-Butyl-4-chloro-N-(1-chloro-3,4-dihydro-naphthalen-2-ylmethyl)-benzenesulfonamide;
N-sec-Butyl-4-chloro-N-(1-methyl-1H-indol-2-ylmethyl)-benzenesulfonamide;
N-sec-Butyl-4-chloro-N-(1-methyl-3-phenyl-allyl)-benzenesulfonamide;
N-sec-Butyl-4-chloro-N-(1-methyl-3-phenyl-propyl)-benzenesulfonamide;
N-sec-Butyl-4-chloro-N-(2-pentyl-3-phenyl-allyl)-benzenesulfonamide;
N-sec-Butyl-4-chloro-N-(3,3-diphenyl-allyl)-benzenesulfonamide;

N-sec-Butyl-4-chloro-N-(3-phenyl-allyl)-benzenesulfonamide;
N-sec-Butyl-4-chloro-N-(3-phenyl-butyl)-benzenesulfonamide;
N-sec-Butyl-4-chloro-N-(3-phenyl-propyl)-benzenesulfonamide;
N-sec-Butyl-4-chloro-N-(4,6-dichloro-2H-chromen-3-ylmethyl)-benzenesulfonamide;
N-sec-Butyl-4-chloro-N-(4-chloro-6-fluoro-2H-chromen-3-ylmethyl)-benzenesulfonamide;
N-sec-Butyl-4-chloro-N-[3-(2-methoxy-phenyl)-allyl]-benzenesulfonamide;
N-tert-Butyl-2-(4-chloro-benzenesulfonylamino)-3-methyl-butyramide; or pharmaceutically acceptable salts thereof.

Specific representative examples of compounds of the invention are the following.

4-Chloro-N-cyclooctyl-N-(3,4-dimethoxy-benzyl)-benzenesulfonamide;
4-Chloro-N-(3,4-dimethoxy-benzyl)-N-(2,3-dimethyl-cyclohexyl)-benzenesulfonamide;
4-Chloro-N-(3,4-dimethoxy-benzyl)-N-(4-methyl-cyclohexyl)-benzenesulfonamide;
4-Chloro-N-(3,4-dimethoxy-benzyl)-N-(1-phenyl-ethyl)-benzenesulfonamide;
4-Chloro-N-(3,4-dimethoxy-benzyl)-N-(1-hydroxymethyl-2-methyl-propyl)-benzenesulfonamide;
4-Chloro-N-(3,4-dimethoxy-benzyl)-N-(3-hydroxy-2,2-dimethyl-propyl)-benzenesulfonamide;
4-Chloro-N-(3,4-dimethoxy-benzyl)-N-[1-(4-methanesulfonyl-phenyl)-ethyl]-benzenesulfonamide;
3-[(4-Chloro-benzenesulfonyl)-(3,4-dimethoxy-benzyl)-amino]-piperidine-1-carboxylic acid tert-butyl ester;
4-Chloro-N-(3,4-dimethoxy-benzyl)-N-(3-hydroxymethyl-bicyclo[2.2.1]hept-2-yl)-benzenesulfonamide;
4-Chloro-N-(3,4-dimethoxy-benzyl)-N—(R-2-hydroxy-1-phenyl-ethyl)-benzenesulfonamide;
4-Chloro-N-(3,4-dimethoxy-benzyl)-N—(R-1-hydroxymethyl-2-phenyl-ethyl)-benzenesulfonamide;
N-Benzyl-4-chloro-N-(1S,2S-2-hydroxy-cyclohexyl)-benzenesulfonamide;
4-Chloro-N—(R-1-hydroxymethyl-3-methyl-butyl)-N-(3-phenyl-allyl)-benzenesulfonamide;
4-Chloro-N—(R-1-hydroxymethyl-3-methyl-butyl)-N-(2-methyl-3-phenyl-allyl)-benzenesulfonamide;
N-Benzo[1,3]dioxol-5-ylmethyl-4-chloro-N—(R-1-hydroxymethyl-3-methyl-butyl)-benzenesulfonamide;
4-Chloro-N-(2,3-dihydro-benzo[1,4]dioxin-6-ylmethyl)-N—(R-1-hydroxymethyl-3-methyl-butyl)-benzenesulfonamide;
4-Chloro-N-(3-fluoro-4-methoxy-benzyl)-N—(R-1-hydroxymethyl-3-methyl-butyl)-benzenesulfonamide;
4-Chloro-N—(R-1-hydroxymethyl-3-methyl-butyl)-N-(4-methoxy-benzyl)-benzenesulfonamide;
4-Chloro-N—(R-1-hydroxymethyl-3-methyl-butyl)-N-(3-phenyl-propyl)-benzenesulfonamide;
4-Chloro-N-(4-chloro-benzyl)-N—(R-1-hydroxymethyl-3-methyl-butyl)-benzenesulfonamide;
N-(4-Bromo-benzyl)-4-chloro-N—(R-1-hydroxymethyl-3-methyl-butyl)-benzenesulfonamide;
4-Chloro-N-(2,4-difluoro-benzyl)-N—(R-1-hydroxymethyl-3-methyl-butyl)-benzenesulfonamide;
R—N-sec-Butyl-4-chloro-N-(3-phenyl-allyl)-benzenesulfonamide;
4-Chloro-N—(R-1,2-dimethyl-propyl)-N-(3-phenyl-allyl)-benzenesulfonamide;
4-Chloro-N-(1-ethyl-propyl)-N-(3-phenyl-allyl)-benzenesulfonamide;
4-Chloro-N-(1-hydroxymethyl-propyl)-N-(3-phenyl-allyl)-benzenesulfonamide;
4-Chloro-N-(2-hydroxy-propyl)-N-(3-phenyl-allyl)-benzenesulfonamide;
4-Chloro-N-(1,3-dimethyl-butyl)-N-(3-phenyl-allyl)-benzenesulfonamide;
4-Chloro-N-(1-methyl-butyl)-N-(3-phenyl-allyl)-benzenesulfonamide;
4-Chloro-N-(2-methoxy-1-methyl-ethyl)-N-(3-phenyl-allyl)-benzenesulfonamide;
4-Chloro-N-(2-methyl-cyclohexyl)-N-(3-phenyl-allyl)-benzenesulfonamide;
3-[(4-Chloro-benzenesulfonyl)-(3-phenyl-allyl)-amino]-piperidine-1-carboxylic acid tert-butyl ester;
4-[(4-Chloro-benzenesulfonyl)-(3-phenyl-allyl)-amino]-piperidine-1-carboxylic acid ethyl ester;
R—N-sec-Butyl-4-chloro-N-(3-phenyl-propyl)-benzenesulfonamide;
4-Chloro-N—(R-1,2-dimethyl-propyl)-N-(3-phenyl-propyl)-benzenesulfonamide;
4-Chloro-N-(1-ethyl-propyl)-N-(3-phenyl-propyl)-benzenesulfonamide;
4-Chloro-N-(1-hydroxymethyl-propyl)-N-(3-phenyl-propyl)-benzenesulfonamide;
4-Chloro-N-(2-hydroxy-propyl)-N-(3-phenyl-propyl)-benzenesulfonamide;
4-Chloro-N-(1,3-dimethyl-butyl)-N-(3-phenyl-propyl)-benzenesulfonamide;
4-Chloro-N-(1-methyl-butyl)-N-(3-phenyl-propyl)-benzenesulfonamide;
4-Chloro-N-(2-methoxy-1-methyl-ethyl)-N-(3-phenyl-propyl)-benzenesulfonamide;
2S,3R-2-[(4-Chloro-benzenesulfonyl)-(3-phenyl-propyl)-amino]-3-hydroxy-N-methyl-butyramide;
4-Chloro-N-(1S,2S-2-hydroxy-cyclopentyl)-N-(3-phenyl-propyl)-benzenesulfonamide;
4-Chloro-N-(2-methyl-cyclohexyl)-N-(3-phenyl-propyl)-benzenesulfonamide;
4-[(4-Chloro-benzenesulfonyl)-(3-phenyl-propyl)-amino]-piperidine-1-carboxylic acid ethyl ester;
N-[3-(4-tert-Butyl-phenyl)-2-methyl-propyl]-4-chloro-N—(R-1-hydroxymethyl-3-methyl-butyl)-benzenesulfonamide;
4-Chloro-N-(4-chloro-6-fluoro-2H-chromen-3-ylmethyl)-N—(R-1-hydroxymethyl-3-methyl-butyl)-benzenesulfonamide;
4-Chloro-N—(R-1-hydroxymethyl-3-methyl-butyl)-N-(2-pentyl-3-phenyl-allyl)-benzenesulfonamide;
4-Chloro-N—(R-1-hydroxymethyl-3-methyl-butyl)-N-[3-(2-methoxy-phenyl)-allyl]-benzenesulfonamide;
N-Benzofuran-2-ylmethyl-4-chloro-N—(R-1-hydroxymethyl-3-methyl-butyl)-benzenesulfonamide;
4-Chloro-N—(R-1-hydroxymethyl-3-methyl-butyl)-N-(3-phenyl-butyl)-benzenesulfonamide;
4-Chloro-N-cyclopropylmethyl-N—(R-1-hydroxymethyl-3-methyl-butyl)-benzenesulfonamide;
R—N-sec-Butyl-4-chloro-N-(1-methyl-3-phenyl-allyl)-benzenesulfonamide;
R—N-sec-Butyl-4-chloro-N-[3-(2-methoxy-phenyl)-allyl]-benzenesulfonamide;
R—N-Benzofuran-2-ylmethyl-N-sec-butyl-4-chloro-benzenesulfonamide;
R—N-sec-Butyl-4-chloro-N-(1-methyl-1H-indol-2-ylmethyl)-benzenesulfonamide;
R—N-sec-Butyl-4-chloro-N-(1-methyl-3-phenyl-propyl)-benzenesulfonamide;

4-Chloro-N-(2,5-dimethyl-cyclohexyl)-N-(3-fluoro-4-methoxy-benzyl)-benzenesulfonamide;
4-Chloro-N-(2,4-difluoro-benzyl)-N-(2,5-dimethyl-cyclohexyl)-benzenesulfonamide;
4-Chloro-N-(2,5-dimethyl-cyclohexyl)-N-(3-phenyl-allyl)-benzenesulfonamide;
4-Chloro-N-(2,5-dimethyl-cyclohexyl)-N-(4-methoxy-benzyl)-benzenesulfonamide;
4-Chloro-N-(3,4-dimethoxy-benzyl)-N-(2,5-dimethyl-cyclohexyl)-benzenesulfonamide;
N-(4-Bromo-benzyl)-4-chloro-N-(2,5-dimethyl-cyclohexyl)-benzenesulfonamide;
4-Chloro-N-(2,5-dimethyl-cyclohexyl)-N-(3-phenyl-propyl)-benzenesulfonamide;
4-Chloro-N-(2,5-dimethyl-cyclohexyl)-N-(2-methyl-3-phenyl-allyl)-benzenesulfonamide;
4-Chloro-N-(3,4-dimethoxy-benzyl)-N-(1R,2S,5R-2-isopropyl-5-methyl-cyclohexyl)-benzenesulfonamide;
4-Chloro-N—(R-1-hydroxymethyl-3-methyl-butyl)-N-(1-methyl-3-phenyl-allyl)-benzenesulfonamide;
N-(2-Benzyl-cyclohexyl)-4-chloro-N—(R-1-hydroxymethyl-3-methyl-butyl)-benzenesulfonamide;
4-Chloro-N—(R-1-hydroxymethyl-3-methyl-butyl)-N-(1,2,3,4-tetrahydro-naphthalen-2-yl)-benzenesulfonamide;
4-Chloro-N-(4,6-dichloro-2H-chromen-3-ylmethyl)-N—(R-1-hydroxymethyl-3-methyl-butyl)-benzenesulfonamide;
4-Chloro-N—(R-1-hydroxymethyl-3-methyl-butyl)-N-(1-methyl-1H-indol-2-ylmethyl)-benzenesulfonamide;
4-Chloro-N-(1-chloro-3,4-dihydro-naphthalen-2-ylmethyl)-N—(R-1-hydroxymethyl-3-methyl-butyl)-benzenesulfonamide;
4-Chloro-N—(R-1-hydroxymethyl-3-methyl-butyl)-N-(1-methyl-3-phenyl-propyl)-benzenesulfonamide;
4-Chloro-N—(R-1-hydroxymethyl-3-methyl-butyl)-N-propyl-benzenesulfonamide;
4-Chloro-N—(R-1-hydroxymethyl-3-methyl-butyl)-N-methyl-benzenesulfonamide;
R—N-sec-Butyl-4-chloro-N-(1-chloro-3,4-dihydro-naphthalen-2-ylmethyl)-benzenesulfonamide;
4-Chloro-N—(R-1-hydroxymethyl-3-methyl-butyl)-benzenesulfonamide;
4-Chloro-N—(R-1,2-dimethyl-propyl)-benzenesulfonamide;
4-Chloro-N—(S-1-hydroxymethyl-3-methyl-butyl)-benzenesulfonamide;
4-[(4-Chloro-benzenesulfonyl)-(R-1-hydroxymethyl-3-methyl-butyl)-amino]-3-methyl-but-2-enoic acid ethyl ester;
4-Chloro-N—(R-1-hydroxymethyl-3-methyl-butyl)-N-naphthalen-2-ylmethyl-benzenesulfonamide;
4-Chloro-N-furan-2-ylmethyl-N—(R-1-hydroxymethyl-3-methyl-butyl)-benzenesulfonamide;
4-Chloro-N-furan-3-ylmethyl-N—(R-1-hydroxymethyl-3-methyl-butyl)-benzenesulfonamide;
4-Chloro-N—(S-1-hydroxymethyl-3-methyl-butyl)-N-(3-phenyl-allyl)-benzenesulfonamide;
4-Chloro-N—(S-1,2-dimethyl-propyl)-N-(3-phenyl-allyl)-benzenesulfonamide;
N-(2-Bromo-3-phenyl-allyl)-4-chloro-N—(R-1-hydroxymethyl-3-methyl-butyl)-benzenesulfonamide;
N-But-2-enyl-4-chloro-N—(R-1-hydroxymethyl-3-methyl-butyl)-benzenesulfonamide;
4-Chloro-N—(R-1-hydroxymethyl-3-methyl-butyl)-N-pentyl-benzenesulfonamide;
4-Chloro-N-(3-furan-2-yl-2-methyl-allyl)-N—(R-1-hydroxymethyl-3-methyl-butyl)-benzenesulfonamide;
4-Chloro-N-(3-furan-2-yl-allyl)-N—(R-1-hydroxymethyl-3-methyl-butyl)-benzenesulfonamide;
4-Chloro-N—(R-1-hydroxymethyl-3-methyl-butyl)-N-(2-methyl-pentyl)-benzenesulfonamide;
4-Chloro-N-(2-ethyl-allyl)-N—(R-1-hydroxymethyl-3-methyl-butyl)-benzenesulfonamide;
4-Chloro-N—(R-1-hydroxymethyl-3-methyl-butyl)-N-(3-methyl-butyl)-benzenesulfonamide;
4-Chloro-N-(2-ethyl-butyl)-N—(R-1-hydroxymethyl-3-methyl-butyl)-benzenesulfonamide;
4-Chloro-N—(R-1-hydroxymethyl-3-methyl-butyl)-N-(3-methyl-but-2-enyl)-benzenesulfonamide;
4-Chloro-N—(R-1-hydroxymethyl-3-methyl-butyl)-N-(3-pyridin-3-yl-allyl)-benzenesulfonamide;
4-Chloro-N—(R-1-hydroxymethyl-3-methyl-butyl)-N-[3-(2-nitro-phenyl)-allyl]-benzenesulfonamide;
4-[(4-Chloro-benzenesulfonyl)-(R-1-hydroxymethyl-3-methyl-butyl)-amino]-but-2-enoic acid ethyl ester;
4-Chloro-N—(R-1-hydroxymethyl-3-methyl-butyl)-N-(2-methyl-4-phenyl-pentyl)-benzenesulfonamide;
4-Chloro-N-cyclohexylmethyl-N—(R-1-hydroxymethyl-3-methyl-butyl)-benzenesulfonamide;
4-Chloro-N-(2-chloro-3-phenyl-allyl)-N—(R-1-hydroxymethyl-3-methyl-butyl)-benzenesulfonamide;
4-Chloro-N-[3-(3-chloro-phenyl)-allyl]-N—(R-1-hydroxymethyl-3-methyl-butyl)-benzenesulfonamide;
4-Chloro-N—(R-1-hydroxymethyl-3-methyl-butyl)-N-(3-p-tolyl-allyl)-benzenesulfonamide;
4-Chloro-N-[3-(4-dimethylamino-phenyl)-allyl]-N—(R-1-hydroxymethyl-3-methyl-butyl)-benzenesulfonamide;
4-Chloro-N-[3-(4-fluoro-phenyl)-allyl]-N—(R-1-hydroxymethyl-3-methyl-butyl)-benzenesulfonamide;
4-Chloro-N—(R-1-hydroxymethyl-3-methyl-butyl)-N-(3-m-tolyl-allyl)-benzenesulfonamide;
4-Chloro-N-[3-(3-fluoro-phenyl)-allyl]-N—(R-1-hydroxymethyl-3-methyl-butyl)-benzenesulfonamide;
4-Chloro-N—(R-1-hydroxymethyl-3-methyl-butyl)-N-(3-o-tolyl-allyl)-benzenesulfonamide;
4-Chloro-N-[3-(4-chloro-phenyl)-allyl]-N—(R-1-hydroxymethyl-3-methyl-butyl)-benzenesulfonamide;
4-Chloro-N-[3-(2-fluoro-phenyl)-allyl]-N—(R-1-hydroxymethyl-3-methyl-butyl)-benzenesulfonamide;
4-Chloro-N-(6-methoxy-pyridin-3-ylmethyl)-N-(2-methyl-cyclohexyl)-benzenesulfonamide;
4-Chloro-N-(6-chloro-pyridin-3-ylmethyl)-N-(2-methyl-cyclohexyl)-benzenesulfonamide;
N-(6-Bromo-pyridin-3-ylmethyl)-4-chloro-N-(2-methyl-cyclohexyl)-benzenesulfonamide; and
4-Chloro-N-(2-methyl-cyclohexyl)-N-(3-pyridin-3-yl-allyl)-benzenesulfonamide.

In another aspect, the compounds of the invention have minimal interaction or preferably, no interaction with notch.

DEFINITIONS

The definitions and explanations below are for the terms as used throughout this entire document including both the specification and the claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its-sense including "and/or" unless the content clearly dictates otherwise.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

APP, amyloid precursor protein, is defined as any APP polypeptide, including APP variants, mutations, and isoforms, for example, as disclosed in U.S. Pat. No. 5,766,846. A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Pharmaceutically acceptable refers to those properties and/or substances that are acceptable to the patient from a toxicological and/or safety point of view.

A therapeutically effective amount is defined as an amount effective to reduce or lessen at least one symptom of the disease being treated or to reduce or delay onset of one or more clinical markers or symptoms of the disease.

By "alkyl" and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons.

By "alkoxy" and "$C_1$-$C_6$ alkoxy" in the present invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and/or iodine.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like. "Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, a polycyclic fused system, or a bi or polycyclic bridged system, such as adamantyl or bicyclo [2.2.1]heptyl. Examples of such radicals include cyclopropyl, cyclobutyl, cyclopentyl and cyclohexyl. Preferred cycloalkyl groups are cyclopentyl, cyclohexyl, and cycloheptyl. The cycloalkyl groups herein are unsubstituted or, as specified, substituted in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "aryl" is meant an aromatic carbocyclic group having a single ring (e.g., phenyl) or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "heteroaryl" is mean at least one or more aromatic ring systems of 5-, 6-, or 7-membered rings which includes fused ring systems of 9-11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide.

The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$) alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$) alkyl, mono($C_1$-$C_6$)alkylamino($C_1$-$C_6$)alkyl, di($C_1$-$C_6$)alkylamino($C_1$-$C_6$)alkyl or =O.

Structures were named using Name Pro IUPAC Naming Software, version 5.09, available from Advanced Chemical Development, Inc., 90 Adelaide Street West, Toronto, Ontario, M5H 3V9, Canada or using ChemDraw v. 6.02 or ChemDraw v. 8.03, both of which are available from Cambridgesoft at 100 Cambridge Park Drive, Cambridge, Mass. 02140 (www.cambridgesoft.com).

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of Formula I.

The invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvates, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a pre-mix for addition to the feed or drinking water.

The disclosures in this document of all articles and references, including patents, are incorporated herein by reference in their entirety.

The invention is illustrated further by the following examples, which are not to be construed as limiting the invention in scope or spirit to the specific procedures described in them.

The starting materials and various intermediates may be obtained from commercial sources, prepared from commercially available compounds, or prepared using known synthetic methods.

General Synthetic Procedures

The compounds of the invention can be prepared using methods well known in the art of organic synthesis. Representative procedures suitable for preparing compounds of the invention are outlined in the following schemes.

Compounds of the invention can be prepared by various methods known to those skilled in the art. For example, the compounds of the invention, as well as all intermediates, can be synthesized by known processes using either solution or solid phase techniques, as shown below.

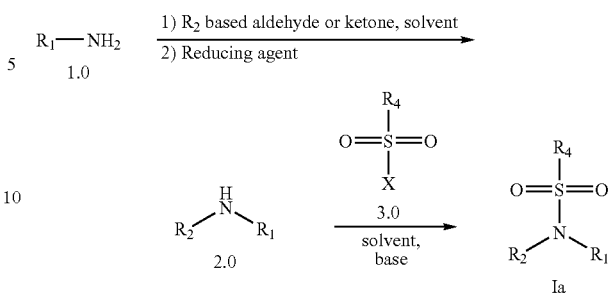

In scheme 1, the definitions of the variables are as defined above, except that R4 is an optionally substituted phenyl, wherein the phenyl is optionally substituted with $R_3$, $R_{3'}$, and/or $R_4$, wherein $R_3$, $R_{3'}$, and $R_4$ are as defined above.

Using standard methods familiar to those skilled in the art, a reductive alkylation is performed by treating primary amine 1.0 with appropriate aldehydes or ketones in a suitable solvent such as methanol. Upon treatment with a reducing agent such as sodium borohydride, sodium cyanoborohydride, or polystyrene bound borohydride, intermediate amines 2.0 are formed. Amines 2.0 are further functionalized by treatment with an appropriate sulfonylhalide 3.0 (where X is a halogen) in a suitable solvent, such as dichloromethane, THF or chloroform, in the presence of a base such as diisopropylethylamine, triethylamine or pyridine at a decreased temperature, resulting in compounds of formula Ia.

Certain compounds of this invention are prepared from other compounds listed in this invention via well-known functional group transformations. Such transformations include ester hydrolysis, amide formation, reductive alkylation, with examples of such described in the preparations. Starting materials are prepared by known methods and are described in the examples below.

Compounds included in this invention are exemplified by the following examples, which should not be construed as limiting the scope of this disclosure. Analogous structures and alternative mechanistic pathways within the scope of the invention may be apparent to those skilled in the art.

In the following examples, $MH^+$ refers to the mass as determined by LC/MS carried out on a ThermoHypersil-Keystone BDS Hypersil C18 column (50 mm×3 mm, 5 micron particle size). $MNa^+$ is used to identify the product based on its sodium adduct. Elution conditions for LC/MS are as follows: Solvents: A. Water with 0.05% TFA (v/v); B. Acetonitrile with 0.05% TFA (v/v); Flow rate: 3 mL/min

| Gradient Method | |
|---|---|
| Time (min) | % B Conc |
| 0 | 5 |
| 0.25 | 5 |
| 2.75 | 95 |
| 3.5 | 95 |
| 3.6 | 5 |
| 4.0 | STOP |

In isolating the following examples, it was necessary to employ a Varian reverse-phase preparative HPLC, utilizing a Phenomenex Aqua $C_{18}$ column (60 mm×21.2 mm, 5 micron particle size). Elution conditions for the HPLC are as follows:

Solvents: A. Water with 0.05% TFA (v/v); B. Acetonitrile with 0.05% TFA (v/v); Flow rate: 25 mL/min

| Gradient Method | |
|---|---|
| Time (min) | % B Conc |
| 0 | 5 |
| 0.75 | 5 |
| 9.5 | 100 |
| 10.5 | 100 |
| 11.5 | 5 |
| 12.0 | STOP |

Example 1

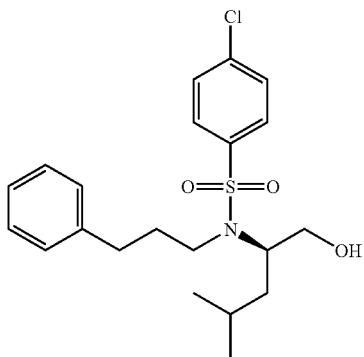

Step 1:
A mixture of 3-phenylpropionaldehyde (215 mg; 1.6 mmol) and R-(−)-leucinol (187 mg; 1.6 mmol) in methanol was stirred at room temperature for 3 h. The reaction was treated with polystyrene bound borohydride (640 mg; 1.6 mmol) and stirred at room temperature overnight. The final mixture was filtered, treated with polystyrene bound sulfonic acid (923 mg; 4.8 mmol) and stirred at room temperature for 1 h. The mixture was filtered, leaving the desired product isolated on the resin. Subsequent treatment with 2.0M methanolic ammonia (8 ml) liberated the desired product, which was concentrated under nitrogen overnight.

Step 2
A mixture of the secondary amine from Step 1 (259 mg; 1.1 mmol) and diisopropylethylamine (568 ul; 4.4 mmol) was stirred in $CH_2Cl_2$ at 0° C. for 1 h. A solution of 4-chlorobenzenesulfonylchloride (232 mg; 1.1 mmol) in $CH_2Cl_2$ was added and subsequently stirred at 10° C. for 18 h. The crude reaction mixture was then purified on a Varian reverse-phase preparative HPLC to afford the desired product.

Example 2

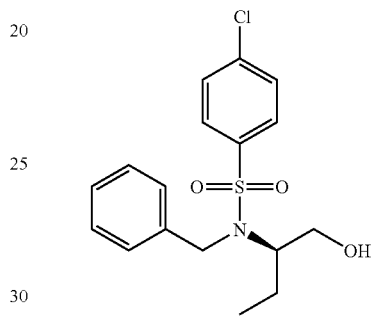

Step 1
A mixture of R-(−)-2-benzylamino-1-butanol (36 mg; 0.2 mmol), 4-chlorobenzenesulfonylchloride (51 mg; 0.24 mmol) and pyridine (126 ul; 1.6 mmol) was stirred in $CH_2Cl_2$ at room temperature for 48 h. The crude reaction mixture was then purified on a Varian reverse-phase preparative HPLC to afford the desired product.

The following compounds were prepared essentially according to the methods and procedures described above.

| EX. No. | Name | M + H+ | M + Na+ |
|---|---|---|---|
| 1 | N-benzyl-4-chloro-N-[(1S,2R)-2-(hydroxymethyl)cyclohexyl]benzenesulfonamide | 393.9 | |
| 2 | 4-Chloro-N-(3,4-dimethoxy-benzyl)-N-(2-methyl-cyclohexyl)-benzenesulfonamide (one isomer) | 438.1 | |
| 3 | 4-Chloro-N-(3,4-dimethoxy-benzyl)-N-(2-methyl-cyclohexyl)-benzenesulfonamide (second isomer) | 438.1 | |
| 4 | 4-Chloro-N-cyclooctyl-N-(3,4-dimethoxy-benzyl)-benzenesulfonamide | | 474.1 |
| 5 | 4-Chloro-N-(3,4-dimethoxy-benzyl)-N-(2,3-dimethyl-cyclohexyl)-benzenesulfonamide | | 474.1 |
| 6 | 4-Chloro-N-(3,4-dimethoxy-benzyl)-N-(4-methyl-cyclohexyl)-benzenesulfonamide | | 460.1 |
| 7 | 4-Chloro-N-(3,4-dimethoxy-benzyl)-N-(1-phenyl-ethyl)-benzenesulfonamide | | 468.1 |
| 8 | 4-chloro-N-(3,4-dimethoxybenzyl)-N-[(1S,2R)-2-hydroxy-1-methyl-2-phenylethyl]benzenesulfonamide | | 498.1 |
| 9 | 4-Chloro-N-(3,4-dimethoxy-benzyl)-N-(1-hydroxymethyl-2-methyl-propyl)-benzenesulfonamide | | 450.0 |
| 10 | 4-Chloro-N-(3,4-dimethoxy-benzyl)-N-(1-naphthalen-1-yl-ethyl)-benzenesulfonamide | | 518.0 |
| 11 | 4-Chloro-N-(3,4-dimethoxy-benzyl)-N-(1-phenyl-4,5-dihydro-1H-pyrazol-3-yl)-benzenesulfonamide | | 508.0 |

-continued

| EX. No. | Name | M + H+ | M + Na+ |
|---|---|---|---|
| 12 | 4-Chloro-N-(3,4-dimethoxy-benzyl)-N-(3-hydroxy-2,2-dimethyl-propyl)-benzenesulfonamide | | 450.0 |
| 13 | 4-Chloro-N-(4-diethylamino-1-methyl-butyl)-N-(3,4-dimethoxy-benzyl)-benzenesulfonamide | 483.2 | |
| 14 | 4-Chloro-N-(3,4-dimethoxy-benzyl)-N-[1-(4-methanesulfonyl-phenyl)-ethyl]-benzenesulfonamide | | 546.0 |
| 15 | 3-[(4-Chloro-benzenesulfonyl)-(3,4-dimethoxy-benzyl)-amino]-piperidine-1-carboxylic acid tert-butyl ester | | 547.2 |
| 16 | 4-chloro-N-(3,4-dimethoxybenzyl)-N-[(1S,3R,4R)-3-(hydroxymethyl)bicyclo[2.2.1]hept-2-yl]benzenesulfonamide | | 490.0 |
| 17 | 4-chloro-N-(3,4-dimethoxybenzyl)-N-[(1S)-2-hydroxy-1-phenylethyl]benzenesulfonamide | | 484.0 |
| 18 | N-[(1R)-1-benzyl-2-hydroxyethyl]-4-chloro-N-(3,4-dimethoxybenzyl)benzenesulfonamide | | 498.0 |
| 19 | N-[(4-chlorophenyl)sulfonyl]-N-(3,4-dimethoxybenzyl)-L-phenylalaninamide | | 511.1 |
| 20 | 4-chloro-N-(3,4-dimethoxybenzyl)-N-[(1R,2S)-2-hydroxy-1-(hydroxymethyl)-2-phenylethyl]benzenesulfonamide | | 514.1 |
| 21 | N-[(1S)-1-benzyl-2-hydroxyethyl]-4-chloro-N-(3,4-dimethoxybenzyl)benzenesulfonamide | | 498.1 |
| 22 | N-benzyl-4-chloro-N-[(1S,2S)-2-hydroxycyclohexyl]benzenesulfonamide | | 402.0 |
| 23 | 4-chloro-N-[(1R)-1-(hydroxymethyl)-3-methylbutyl]-N-(4-methoxybenzyl)benzenesulfonamide | | 434.1 |
| 24 | 4-chloro-N-(4-chlorobenzyl)-N-[(1R)-1-(hydroxymethyl)-3-methylbutyl]benzenesulfonamide | 416.0 | |
| 25 | N-(4-bromobenzyl)-4-chloro-N-[(1R)-1-(hydroxymethyl)-3-methylbutyl]benzenesulfonamide | 462.0 | |
| 26 | 4-chloro-N-(2,4-difluorobenzyl)-N-[(1R)-1-(hydroxymethyl)-3-methylbutyl]benzenesulfonamide | 418.1 | |
| 27 | N-benzyl-4-chloro-N-[(1S)-1-(hydroxymethyl)propyl]benzenesulfonamide | 354.0 | |
| 28 | 4-chloro-N-[(1R)-1-(hydroxymethyl)-3-methylbutyl]-N-(3-phenylpropyl)benzenesulfonamide | 410.1 | |
| 29 | N2-[(4-chlorophenyl)sulfonyl]-N1-methyl-L-alaninamide | 277.0 | |
| 30 | N-tert-Butyl-2-(4-chloro-benzenesulfonylamino)-3-methyl-butyramide | 347.0 | |
| 31 | 4-Chloro-N-ethyl-N-[2-hydroxy-2-(3-hydroxy-phenyl)-ethyl]-benzenesulfonamide | 356.0 | |
| 32 | 4-Chloro-N-(2-hydroxy-1-methyl-2-phenyl-ethyl)-N-methyl-benzenesulfonamide | | 362.0 |
| 33 | 4-Chloro-N-methyl-N-(1-methyl-piperidin-4-yl)-benzenesulfonamide | 303.1 | |
| 34 | 4-Chloro-N-cyclohexyl-N-(2-hydroxy-2-phenyl-ethyl)-benzenesulfonamide | | 416.1 |
| 35 | 4-Chloro-N-ethyl-N-(2-pyridin-2-yl-ethyl)-benzenesulfonamide | 325.1 | |
| 36 | N,N-Di-sec-butyl-4-chloro-benzenesulfonamide | 304.1 | |
| 37 | 4-Chloro-N-(2-cyano-ethyl)-N-cyclopropyl-benzenesulfonamide | 285.0 | |
| 38 | 4-Chloro-N-methyl-N-(2-pyridin-4-yl-ethyl)-benzenesulfonamide | 311.1 | |
| 39 | [(4-Chloro-benzenesulfonyl)-methyl-amino]-acetic acid ethyl ester | 292.0 | |
| 40 | 4-chloro-N-[(1S,2S)-2-hydroxy-1-methyl-2-phenylethyl]-N-methylbenzenesulfonamide | | 362.0 |
| 41 | 4-chloro-N-[(1R,2S)-2-hydroxy-1-methyl-2-phenylethyl]-N-methylbenzenesulfonamide | | 362.0 |
| 42 | 4-Chloro-N-cyclohexyl-N-(2-hydroxy-ethyl)-benzenesulfonamide | 318.0 | |

-continued

| EX. No. | Name | M + H+ | M + Na+ |
|---|---|---|---|
| 43 | 4-Chloro-N-cyanomethyl-N-methyl-benzenesulfonamide | | 266.9 |
| 44 | 4-Chloro-N-(2-cyano-ethyl)-N-ethyl-benzenesulfonamide | 273.0 | |
| 45 | 4-Chloro-N-isopropyl-N-(2-pyridin-4-yl-ethyl)-benzenesulfonamide | 339.0 | |
| 46 | 4-Chloro-N-[2-(3,4-dihydroxy-phenyl)-2-oxo-ethyl]-N-methyl-benzenesulfonamide | 356.0 | |
| 47 | N-Allyl-4-chloro-N-cyclohexyl-benzenesulfonamide | 314.0 | |
| 48 | 4-Chloro-N,N-dicyclohexyl-benzenesulfonamide | 356.7 | |
| 49 | 4-Chloro-N-cyclohexyl-N-isopropyl-benzenesulfonamide | 315.8 | |
| 50 | 4-Chloro-N,N-diisopropyl-benzenesulfonamide | 275.5 | |
| 51 | 4-Chloro-N,N-divinyl-benzenesulfonamide | 243.8 | |
| 52 | N-(1-Benzyl-pyrrolidin-3-yl)-4-chloro-N-ethyl-benzenesulfonamide | 379.0 | |
| 53 | 4-Chloro-N-{3-methoxy-4-[2-(4-methyl-thiazol-5-yl)-ethoxy]-benzyl}-N-(2-methyl-allyl)-benzenesulfonamide | 508 | |
| 54 | 4-Chloro-N-(2-hydroxy-propyl)-N-{3-methoxy-4-[2-(4-methyl-thiazol-5-yl)-ethoxy]-benzyl}-benzenesulfonamide | 512 | |
| 55 | 4-Chloro-N-{3-methoxy-4-[2-(4-methyl-thiazol-5-yl)-ethoxy]-benzyl}-N-(2-methyl-cyclohexyl)-benzenesulfonamide | 550.1 | |
| 56 | 4-Chloro-N-(2,3-dihydroxy-propyl)-N-{3-methoxy-4-[2-(4-methyl-thiazol-5-yl)-ethoxy]-benzyl}-benzenesulfonamide | 528.9 | |
| 57 | 4-Chloro-N-(1-hydroxymethyl-pentyl)-N-{3-methoxy-4-[2-(4-methyl-thiazol-5-yl)-ethoxy]-benzyl}-benzenesulfonamide | 554.1 | |
| 58 | 4-Chloro-N-cycloheptyl-N-{3-methoxy-4-[2-(4-methyl-thiazol-5-yl)-ethoxy]-benzyl}-benzenesulfonamide | 550 | |
| 59 | 4-chloro-N-[(1S)-1-(hydroxymethyl)-3-methylbutyl]-N-{3-methoxy-4-[2-(4-methyl-1,3-thiazol-5-yl) ethoxy]benzyl}benzenesulfonamide | 554 | |
| 60 | N-(2-Amino-benzyl)-4-chloro-N-{3-methoxy-4-[2-(4-methyl-thiazol-5-yl)-ethoxy]-benzyl}-benzenesulfonamide | 559 | |
| 61 | 4-Chloro-N-{3-methoxy-4-[2-(4-methyl-thiazol-5-yl)-ethoxy]-benzyl}-N-(3-methylsulfanyl-propyl)-benzenesulfonamide | 542 | |
| 62 | 4-Chloro-N-(3-hydroxy-butyl)-N-{3-methoxy-4-[2-(4-methyl-thiazol-5-yl)-ethoxy]-benzyl}-benzenesulfonamide | 526 | |
| 63 | 4-Chloro-N-{3-methoxy-4-[2-(4-methyl-thiazol-5-yl)-ethoxy]-benzyl}-N-pyridin-2-ylmethyl-benzenesulfonamide | 544.9 | |
| 64 | 4-Chloro-N-(2,4-dichloro-benzyl)-N-{3-methoxy-4-[2-(4-methyl-thiazol-5-yl)-ethoxy]-benzyl}-benzenesulfonamide | 612.9 | |
| 65 | 4-chloro-N-{[(1R,2S)-2-hydroxycyclohexyl]methyl}-N-{3-methoxy-4-[2-(4-methyl-1,3-thiazol-5-yl) ethoxy]benzyl}benzenesulfonamide | 566 | |
| 66 | 4-Chloro-N-cyclohexyl-N-{3-methoxy-4-[2-(4-methyl-thiazol-5-yl)-ethoxy]-benzyl}-benzenesulfonamide | 535.8 | |
| 67 | 4-Chloro-N-{3-methoxy-4-[2-(4-methyl-thiazol-5-yl)-ethoxy]-benzyl}-N-(4-methyl-cyclohexyl)-benzenesulfonamide | 549.8 | |
| 68 | 4-Chloro-N-cyclobutyl-N-{3-methoxy-4-[2-(4-methyl-thiazol-5-yl)-ethoxy]-benzyl}-benzenesulfonamide | 507.8 | |
| 69 | 4-Chloro-N-cyclopentyl-N-{3-methoxy-4-[2-(4-methyl-thiazol-5-yl)-ethoxy]-benzyl}-benzenesulfonamide | 521.8 | |
| 70 | 4-Chloro-N-{3-methoxy-4-[2-(4-methyl-thiazol-5-yl)-ethoxy]-benzyl}-N-(3-methoxy-propyl)-benzenesulfonamide | 525.8 | |
| 71 | 4-Chloro-N-{3-methoxy-4-[2-(4-methyl-thiazol-5-yl)-ethoxy]-benzyl}-N-prop-2-ynyl-benzenesulfonamide | 491.8 | |

-continued

| EX. No. | Name | M + H+ | M + Na+ |
|---|---|---|---|
| 72 | 4-Chloro-N-{3-methoxy-4-[2-(4-methyl-thiazol-5-yl)-ethoxy]-benzyl}-N-(tetrahydro-furan-2-ylmethyl)-benzenesulfonamide | 537.8 | |
| 73 | 4-Chloro-N-cyclopropylmethyl-N-{3-methoxy-4-[2-(4-methyl-thiazol-5-yl)-ethoxy]-benzyl}-benzenesulfonamide | 507.8 | |
| 74 | 4-Chloro-N-{3-methoxy-4-[2-(4-methyl-thiazol-5-yl)-ethoxy]-benzyl}-N-(2-methyl-butyl)-benzenesulfonamide | 523.8 | |
| 75 | 4-Chloro-N-{3-methoxy-4-[2-(4-methyl-thiazol-5-yl)-ethoxy]-benzyl}-N-(1-phenyl-ethyl)-benzenesulfonamide | 557.9 | |
| 76 | 4-Chloro-N-{3-methoxy-4-[2-(4-methyl-thiazol-5-yl)-ethoxy]-benzyl}-N-(3-methyl-butyl)-benzenesulfonamide | 523.8 | |
| 77 | 4-Chloro-N-ethyl-N-{3-methoxy-4-[2-(4-methyl-thiazol-5-yl)-ethoxy]-benzyl}-benzenesulfonamide | 481.8 | |
| 78 | 4-chloro-N-(3,4-dimethoxybenzyl)-N-[(1S)-1-(hydroxymethyl)propyl]benzenesulfonamide | | 437 |
| 79 | 4-chloro-N-(3,4-dimethoxybenzyl)-N-[(1S)-1-(hydroxymethyl)-3-methylbutyl]benzenesulfonamide | | 465.1 |
| 80 | 4-Chloro-N-(3,4-dimethoxy-benzyl)-N-(2-methyl-cyclohexyl)-benzenesulfonamide | | 475.1 |
| 81 | N-Benzyl-N-sec-butyl-4-chloro-benzenesulfonamide | | 361 |
| 82 | 4-Chloro-N-(3,4-dimethoxy-benzyl)-N-(2-methyl-cyclohexyl)-benzenesulfonamide | 438.8 | |
| 83 | 4-Chloro-N-(3,4-dimethoxy-benzyl)-N-(2-methyl-cyclohexyl)-benzenesulfonamide | 438.8 | |
| 84 | N-(1,3-benzodioxol-5-ylmethyl)-4-chloro-N-[(1S)-1-(hydroxymethyl)-3-methylbutyl]benzenesulfonamide | | 449.1 |
| 85 | 4-chloro-N-(2,3-dihydro-1,4-benzodioxin-6-ylmethyl)-N-[(1S)-1-(hydroxymethyl)-3-methylbutyl]benzenesulfonamide | | 463.1 |
| 86 | 4-chloro-N-(3,4-dimethylbenzyl)-N-[(1S)-1-(hydroxymethyl)-3-methylbutyl]benzenesulfonamide | | 433.1 |
| 87 | 4-chloro-N-(3-fluoro-4-methoxybenzyl)-N-[(1S)-1-(hydroxymethyl)-3-methylbutyl]benzenesulfonamide | | 453.1 |
| 88 | 4-Chloro-N-(3,4-dimethoxy-benzyl)-N-(2-methyl-cyclohexyl)-benzenesulfonamide | | 461.1 |
| 89 | 4-Chloro-N-(3,4-dimethoxy-benzyl)-N-(2-methyl-cyclohexyl)-benzenesulfonamide | | 461.1 |
| 90 | 4-chloro-N-[(1S)-1-(hydroxymethyl)-3-methylbutyl]-N-[(2E)-3-phenylprop-2-en-1-yl]benzenesulfonamide | | 431.1 |
| 91 | 4-chloro-N-[(1S)-1-(hydroxymethyl)-3-methylbutyl]-N-[(2E)-2-methyl-3-phenylprop-2-en-1-yl]benzenesulfonamide | | 445.1 |
| 92 | 4-Chloro-N-(1-hydroxymethyl-3-methyl-butyl)-N-(1-methyl-3-phenyl-allyl)-benzenesulfonamide | | 444 |
| 93 | N-(2-Benzyl-cyclohexyl)-4-chloro-N-(1-hydroxymethyl-3-methyl-butyl)-benzenesulfonamide | | 486.2 |
| 94 | 4-Chloro-N-(1-hydroxymethyl-3-methyl-butyl)-N-(1,2,3,4-tetrahydro-naphthalen-2-yl)-benzenesulfonamide | | 444 |
| 95 | 4-Chloro-N-(4,6-dichloro-2H-chromen-3-ylmethyl)-N-(1-hydroxymethyl-3-methyl-butyl)-benzenesulfonamide | | 527 |
| 96 | 4-Chloro-N-(1-hydroxymethyl-3-methyl-butyl)-N-(1-methyl-1H-indol-2-ylmethyl)-benzenesulfonamide | 435.1 | |
| 97 | 4-Chloro-N-(1-chloro-3,4-dihydro-naphthalen-2-ylmethyl)-N-(1-hydroxymethyl-3-methyl-butyl)-benzenesulfonamide | | 490.1 |
| 98 | 4-Chloro-N-(1-hydroxymethyl-3-methyl-butyl)-N-(1-methyl-3-phenyl-propyl)-benzenesulfonamide | 424.1 | |
| 99 | 4-Chloro-N-(1-hydroxymethyl-3-methyl-butyl)-N-propyl-benzenesulfonamide | 334 | |

-continued

| EX. No. | Name | M + H+ | M + Na+ |
|---|---|---|---|
| 100 | 4-Chloro-N-(1-hydroxymethyl-3-methyl-butyl)-N-methyl-benzenesulfonamide | 306.1 | |
| 101 | N-sec-Butyl-4-chloro-N-(4-chloro-6-fluoro-2H-chromen-3-ylmethyl)-benzenesulfonamide | | 466 |
| 102 | N-sec-Butyl-4-chloro-N-(4,6-dichloro-2H-chromen-3-ylmethyl)-benzenesulfonamide | 460 | |
| 103 | N-sec-Butyl-4-chloro-N-(2-pentyl-3-phenyl-allyl)-benzenesulfonamide | | 456.1 |
| 104 | N-sec-Butyl-4-chloro-N-(3,3-diphenyl-allyl)-benzenesulfonamide | | 462.1 |
| 105 | N-Benzofuran-2-ylmethyl-N-sec-butyl-4-chloro-benzenesulfonamide | | 400 |
| 106 | N-sec-Butyl-4-chloro-N-(1-methyl-1H-indol-2-ylmethyl)-benzenesulfonamide | 391.1 | |
| 107 | N-sec-Butyl-4-chloro-N-(1-chloro-3,4-dihydro-naphthalen-2-ylmethyl)-benzenesulfonamide | | 445.9 |
| 108 | 4-Chloro-N-(1-hydroxymethyl-3-methyl-butyl)-N-[3-(2-methoxy-phenyl)-allyl]-benzenesulfonamide | | 460.1 |
| 109 | N-Benzofuran-2-ylmethyl-4-chloro-N-(1-hydroxymethyl-3-methyl-butyl)-benzenesulfonamide | | 444.0 |
| 110 | 4-Chloro-N-cyclopropylmethyl-N-(1-hydroxymethyl-3-methyl-butyl)-benzenesulfonamide | 346.0 | |
| 111 | 4-Chloro-N-(2-methyl-cyclohexyl)-N-(3-phenyl-allyl)-benzenesulfonamide | | 426.1 |
| 112 | 4-Chloro-N-(1-hydroxymethyl-3-methyl-butyl)-N-(3-phenyl-butyl)-benzenesulfonamide | 424.1 | |
| 113 | 4-Chloro-N-(1-methyl-butyl)-N-(3-phenyl-allyl)-benzenesulfonamide | | 400.1 |
| 114 | 4-Chloro-N-(1,3-dimethyl-butyl)-N-(3-phenyl-allyl)-benzenesulfonamide | | 414.1 |
| 115 | 4-Chloro-N-(2-methyl-cyclohexyl)-N-(3-phenyl-propyl)-benzenesulfonamide | | 428.1 |
| 116 | 4-Chloro-N-(1-methyl-butyl)-N-(3-phenyl-propyl)-benzenesulfonamide | 380.1 | |
| 117 | 4-Chloro-N-(1-ethyl-propyl)-N-(3-phenyl-allyl)-benzenesulfonamide | | 400.1 |
| 118 | N-[3-(4-tert-Butyl-phenyl)-2-methyl-propyl]-4-chloro-N-(1-hydroxymethyl-3-methyl-butyl)-benzenesulfonamide | 480.2 | |
| 119 | 4-Chloro-N-(1,3-dimethyl-butyl)-N-(3-phenyl-propyl)-benzenesulfonamide | 394.1 | |
| 120 | 4-Chloro-N-(2-methoxy-1-methyl-ethyl)-N-(3-phenyl-propyl)-benzenesulfonamide | 382.1 | |
| 121 | 4-Chloro-N-(4-chloro-6-fluoro-2H-chromen-3-ylmethyl)-N-(1-hydroxymethyl-3-methyl-butyl)-benzenesulfonamide | | 510.1 |
| 122 | 4-Chloro-N-(2-methoxy-1-methyl-ethyl)-N-(3-phenyl-allyl)-benzenesulfonamide | | 402.0 |
| 123 | 4-Chloro-N-(1-ethyl-propyl)-N-(3-phenyl-propyl)-benzenesulfonamide | 380.0 | |
| 124 | 4-Chloro-N-(1,2-dimethyl-propyl)-N-(3-phenyl-allyl)-benzenesulfonamide | | 400.1 |
| 125 | N-sec-Butyl-4-chloro-N-(1-methyl-3-phenyl-propyl)-benzenesulfonamide | | 402.1 |
| 126 | N-sec-Butyl-4-chloro-N-(3-phenyl-allyl)-benzenesulfonamide | | 386.0 |
| 127 | 4-Chloro-N-(1-hydroxymethyl-propyl)-N-(3-phenyl-propyl)-benzenesulfonamide | 382.1 | |
| 128 | 4-Chloro-N-(2-hydroxy-propyl)-N-(3-phenyl-propyl)-benzenesulfonamide | 368.1 | |
| 129 | 4-Chloro-N-(1-hydroxymethyl-propyl)-N-(3-phenyl-allyl)-benzenesulfonamide | | 402.0 |
| 130 | 4-Chloro-N-(1,2-dimethyl-propyl)-N-(3-phenyl-propyl)-benzenesulfonamide | 380.1 | |
| 131 | N-sec-Butyl-4-chloro-N-[3-(2-methoxy-phenyl)-allyl]-benzenesulfonamide | | 416.1 |
| 132 | 4-Chloro-N-(2-hydroxy-propyl)-N-(3-phenyl-allyl)-benzenesulfonamide | | 388.0 |
| 133 | N-sec-Butyl-4-chloro-N-(3-phenyl-propyl)-benzenesulfonamide | 366.1 | |
| 134 | N-sec-Butyl-4-chloro-N-(1-methyl-3-phenyl-allyl)-benzenesulfonamide | | 400.1 |

-continued

| EX. No. | Name | M + H+ | M + Na+ |
|---|---|---|---|
| 135 | 2-[(4-Chloro-benzenesulfonyl)-(3-phenyl-propyl)-amino]-3-hydroxy-N-methyl-butyramide | 426.1 | |
| 136 | 4-Chloro-N-(1-hydroxymethyl-3-methyl-butyl)-N-(2-pentyl-3-phenyl-allyl)-benzenesulfonamide | | 500.1 |
| 137 | N-sec-Butyl-4-chloro-N-(3-phenyl-butyl)-benzenesulfonamide | 380.1 | |
| 138 | (S)-4-chloro-N-cinnamyl-N-(1-hydroxy-4-methylpentan-2-yl)benzenesulfonamide | | 431.1 |
| 139 | 4-Chloro-N-(1-hydroxymethyl-3-methyl-butyl)-N-(3-phenyl-propyl)-benzenesulfonamide | 410.1 | |
| 140 | 4-Chloro-N-(1-hydroxymethyl-3-methyl-butyl)-N-(2-methyl-3-phenyl-allyl)-benzenesulfonamide | | 445.1 |
| 141 | 4-Chloro-N-(2,3-dihydro-benzo[1,4]dioxin-6-ylmethyl)-N-(1-hydroxymethyl-3-methyl-butyl)-benzenesulfonamide | | 463.1 |
| 142 | N-Benzo[1,3]dioxol-5-ylmethyl-4-chloro-N-(1-hydroxymethyl-3-methyl-butyl)-benzenesulfonamide | | 449.1 |
| 143 | 4-Chloro-N-(3-fluoro-4-methoxy-benzyl)-N-(1-hydroxymethyl-3-methyl-butyl)-benzenesulfonamide | | 453.1 |
| 144 | 4-Chloro-N-(2,4-difluoro-benzyl)-N-(1-hydroxymethyl-3-methyl-butyl)-benzenesulfonamide | 418.1 | — |
| 145 | 4-Chloro-N-(1-hydroxymethyl-3-methyl-butyl)-N-(4-methoxy-benzyl)-benzenesulfonamide | | 434.1 |
| 146 | 4-Chloro-N-(4-chloro-benzyl)-N-(1-hydroxymethyl-3-methyl-butyl)-benzenesulfonamide | 416.0 | — |
| 147 | N-(4-Bromo-benzyl)-4-chloro-N-(1-hydroxymethyl-3-methyl-butyl)-benzenesulfonamide | 462.0 | — |
| 148 | 4-Chloro-N-(3,4-dimethoxy-benzyl)-N-(2-methyl-cyclohexyl)-benzenesulfonamide | 438.1 | — |
| 149 | 4-Chloro-N-(3,4-dimethoxy-benzyl)-N-(2-methyl-cyclohexyl)-benzenesulfonamide | 438.8 | |
| 150 | N-Benzyl-4-chloro-N-(1-hydroxymethyl-propyl)-benzenesulfonamide | 354.0 | — |
| 151 | 4-Chloro-N-(3,4-dimethoxy-benzyl)-N-(2-methyl-cyclohexyl)-benzenesulfonamide | | 475.1 |
| 152 | 4-Chloro-N-(3,4-dimethoxy-benzyl)-N-(1-hydroxymethyl-3-methyl-butyl)-benzenesulfonamide | | 465.1 |
| 153 | N-Benzyl-4-chloro-N-(2-hydroxy-cyclohexyl)-benzenesulfonamide | | 402.0 |
| 154 | N,N-Di-sec-butyl-4-chloro-benzenesulfonamide | 304.1 | — |
| 155 | 4-Chloro-N-(1-hydroxymethyl-3-methyl-butyl)-N-{3-methoxy-4-[2-(4-methyl-thiazol-5-yl)-ethoxy]-benzyl}-benzenesulfonamide | 554 | |
| 156 | 4-Chloro-N-(3,4-dimethoxy-benzyl)-N-(2-methyl-cyclohexyl)-benzenesulfonamide | | 461.1 |
| 157 | 4-Chloro-N-(3,4-dimethoxy-benzyl)-N-(1-hydroxymethyl-2-methyl-propyl)-benzenesulfonamide | | 450.0 |
| 158 | 4-Chloro-N-(3,4-dimethoxy-benzyl)-N-(1-hydroxymethyl-propyl)-benzenesulfonamide | | 437 |
| 159 | 4-Chloro-N-cyclohexyl-N-isopropyl-benzenesulfonamide | 315.8 | |
| 160 | 4-Chloro-N-{3-methoxy-4-[2-(4-methyl-thiazol-5-yl)-ethoxy]-benzyl}-N-(2-methyl-cyclohexyl)-benzenesulfonamide | 550.1 | |
| 161 | 4-Chloro-N-(3,4-dimethoxy-benzyl)-N-(2-methyl-cyclohexyl)-benzenesulfonamide | | 461.1 |
| 162 | 4-Chloro-N,N-diisopropyl-benzenesulfonamide | 275.5 | — |
| 163 | 4-Chloro-N-(3,4-dimethoxy-benzyl)-N-(2-methyl-cyclohexyl)-benzenesulfonamide | 438.1 | — |
| 164 | 4-Chloro-N-(3,4-dimethoxy-benzyl)-N-(2-methyl-cyclohexyl)-benzenesulfonamide | 438.8 | |
| 165 | 4-Chloro-N-(3,4-dimethoxy-benzyl)-N-(2,3-dimethyl-cyclohexyl)-benzenesulfonamide | | 474.1 |
| 166 | N-Benzyl-N-sec-butyl-4-chloro-benzenesulfonamide | | 361 |

-continued

| EX. No. | Name | M + H+ | M + Na+ |
|---|---|---|---|
| 167 | 4-Chloro-N-(1-hydroxymethyl-pentyl)-N-{3-methoxy-4-[2-(4-methyl-thiazol-5-yl)-ethoxy]-benzyl}-benzenesulfonamide | 554.1 | |
| 168 | 4-Chloro-N-cyclooctyl-N-(3,4-dimethoxy-benzyl)-benzenesulfonamide | | 474.1 |
| 169 | 4-Chloro-N-cyclohexyl-N-{3-methoxy-4-[2-(4-methyl-thiazol-5-yl)-ethoxy]-benzyl}-benzenesulfonamide | 535.8 | |
| 170 | N-Allyl-4-chloro-N-cyclohexyl-benzenesulfonamide | 314.0 | — |
| 171 | 4-Chloro-N-(3,4-dimethoxy-benzyl)-N-(2-hydroxy-1-phenyl-ethyl)-benzenesulfonamide | | 484.0 |
| 172 | 4-Chloro-N-(3,4-dimethoxy-benzyl)-N-(4-methyl-cyclohexyl)-benzenesulfonamide | | 460.1 |
| 173 | 4-Chloro-N-(3-hydroxy-butyl)-N-{3-methoxy-4-[2-(4-methyl-thiazol-5-yl)-ethoxy]-benzyl}-benzenesulfonamide | 526 | |
| 174 | 4-Chloro-N-(2-hydroxy-cyclohexylmethyl)-N-{3-methoxy-4-[2-(4-methyl-thiazol-5-yl)-ethoxy]-benzyl}-benzenesulfonamide | 566 | |
| 175 | 4-Chloro-N,N-divinyl-benzenesulfonamide | 243.8 | — |
| 176 | 4-Chloro-N,N-dicyclohexyl-benzenesulfonamide | 356.7 | — |
| 177 | 4-Chloro-N-(3,4-dimethoxy-benzyl)-N-(3-hydroxy-2,2-dimethyl-propyl)-benzenesulfonamide | | 450.0 |
| 178 | 4-Chloro-N-cyclopentyl-N-{3-methoxy-4-[2-(4-methyl-thiazol-5-yl)-ethoxy]-benzyl}-benzenesulfonamide | 521.8 | |
| 179 | N-(2-Amino-benzyl)-4-chloro-N-{3-methoxy-4-[2-(4-methyl-thiazol-5-yl)-ethoxy]-benzyl}-benzenesulfonamide | 559 | |
| 180 | 4-Chloro-N-cyclohexyl-N-(2-hydroxy-2-phenyl-ethyl)-benzenesulfonamide | — | 416.1 |
| 181 | 4-Chloro-N-{3-methoxy-4-[2-(4-methyl-thiazol-5-yl)-ethoxy]-benzyl}-N-(2-methyl-butyl)-benzenesulfonamide | 523.8 | |
| 182 | 4-Chloro-N-(3,4-dimethoxy-benzyl)-N-(3-hydroxymethyl-bicyclo[2.2.1]hept-2-yl)-benzenesulfonamide | | 490.0 |
| 183 | 4-Chloro-N-(3,4-dimethoxy-benzyl)-N-(1-hydroxymethyl-2-phenyl-ethyl)-benzenesulfonamide | | 498.0 |
| 184 | 4-Chloro-N-(3,4-dimethoxy-benzyl)-N-[1-(4-methanesulfonyl-phenyl)-ethyl]-benzenesulfonamide | | 546.0 |
| 185 | 4-Chloro-N-(2-hydroxy-propyl)-N-{3-methoxy-4-[2-(4-methyl-thiazol-5-yl)-ethoxy]-benzyl}-benzenesulfonamide | 512 | |
| 186 | 3-[(4-Chloro-benzenesulfonyl)-(3,4-dimethoxy-benzyl)-amino]-piperidine-1-carboxylic acid tert-butyl ester | | 547.2 |
| 187 | 4-Chloro-N-cycloheptyl-N-{3-methoxy-4-[2-(4-methyl-thiazol-5-yl)-ethoxy]-benzyl}-benzenesulfonamide | 550 | |
| 188 | 4-Chloro-N-(3,4-dimethoxy-benzyl)-N-(1-phenyl-ethyl)-benzenesulfonamide | | 468.1 |
| 189 | 4-Chloro-N-{3-methoxy-4-[2-(4-methyl-thiazol-5-yl)-ethoxy]-benzyl}-N-(3-methylsulfanyl-propyl)-benzenesulfonamide | 542 | |
| 190 | 4-Chloro-N-{3-methoxy-4-[2-(4-methyl-thiazol-5-yl)-ethoxy]-benzyl}-N-(4-methyl-cyclohexyl)-benzenesulfonamide | 549.8 | |
| 191 | 4-Chloro-N-ethyl-N-{3-methoxy-4-[2-(4-methyl-thiazol-5-yl)-ethoxy]-benzyl}-benzenesulfonamide | 481.8 | |
| 192 | 4-Chloro-N-{3-methoxy-4-[2-(4-methyl-thiazol-5-yl)-ethoxy]-benzyl}-N-pyridin-2-ylmethyl-benzenesulfonamide | 544.9 | |
| 193 | 4-Chloro-N-{3-methoxy-4-[2-(4-methyl-thiazol-5-yl)-ethoxy]-benzyl}-N-prop-2-ynyl-benzenesulfonamide | 491.8 | |
| 194 | 4-Chloro-N-{3-methoxy-4-[2-(4-methyl-thiazol-5-yl)-ethoxy]-benzyl}-N-(3-methyl-butyl)-benzenesulfonamide | 523.8 | |
| 195 | 4-Chloro-N-{3-methoxy-4-[2-(4-methyl-thiazol-5-yl)-ethoxy]-benzyl}-N-(tetrahydro-furan-2-ylmethyl)-benzenesulfonamide | 537.8 | |

-continued

| EX. No. | Name | M + H+ | M + Na+ |
|---|---|---|---|
| 196 | 4-Chloro-N-cyclopropylmethyl-N-{3-methoxy-4-[2-(4-methyl-thiazol-5-yl)-ethoxy]-benzyl}-benzenesulfonamide | 507.8 | |
| 197 | 4-Chloro-N-{3-methoxy-4-[2-(4-methyl-thiazol-5-yl)-ethoxy]-benzyl}-N-(3-methoxy-propyl)-benzenesulfonamide | 525.8 | |
| 198 | 4-Chloro-N-(2,4-dichloro-benzyl)-N-{3-methoxy-4-[2-(4-methyl-thiazol-5-yl)-ethoxy]-benzyl}-benzenesulfonamide | 612.9 | |
| 199 | 4-Chloro-N-(2,3-dihydroxy-propyl)-N-{3-methoxy-4-[2-(4-methyl-thiazol-5-yl)-ethoxy]-benzyl}-benzenesulfonamide | 528.9 | |
| 200 | 4-Chloro-N-isopropyl-N-(2-pyridin-4-yl-ethyl)-benzenesulfonamide | 339.0 | — |
| 201 | 4-Chloro-N-cyclobutyl-N-{3-methoxy-4-[2-(4-methyl-thiazol-5-yl)-ethoxy]-benzyl}-benzenesulfonamide | 507.8 | |
| 202 | 4-Chloro-N-cyclohexyl-N-(2-hydroxy-ethyl)-benzenesulfonamide | 318.0 | — |
| 203 | N-Benzyl-4-chloro-N-(2-hydroxymethyl-cyclohexyl)-benzenesulfonamide | 393.9 | — |
| 204 | 4-Chloro-N-(3,4-dimethoxy-benzyl)-N-(2-hydroxy-1-methyl-2-phenyl-ethyl)-benzenesulfonamide | | 498.1 |
| 205 | 4-Chloro-N-(3,4-dimethoxy-benzyl)-N-(1-naphthalen-1-yl-ethyl)-benzenesulfonamide | | 518.0 |
| 206 | 4-Chloro-N-(3,4-dimethoxy-benzyl)-N-(1-phenyl-4,5-dihydro-1H-pyrazol-3-yl)-benzenesulfonamide | | 508.0 |
| 207 | 4-Chloro-N-(4-diethylamino-1-methyl-butyl)-N-(3,4-dimethoxy-benzyl)-benzenesulfonamide | 483.2 | — |
| 208 | 2-[(4-Chloro-benzenesulfonyl)-(3,4-dimethoxy-benzyl)-amino]-3-phenyl-propionamide | | 511.1 |
| 209 | 4-Chloro-N-(3,4-dimethoxy-benzyl)-N-(2-hydroxy-1-hydroxymethyl-2-phenyl-ethyl)-benzenesulfonamide | | 514.1 |
| 210 | 4-Ghloro-N-(3,4-dimethoxy-benzyl)-N-(1-hydroxymethyl-2-phenyl-ethyl)-benzenesulfonamide | | 498.1 |
| 211 | 2-(4-Chloro-benzenesulfonylamino)-N-methyl-propionamide | 277.0 | |
| 212 | N-tert-Butyl-2-(4-chloro-benzenesulfonylamino)-3-methyl-butyramide | 347.0 | |
| 213 | 4-Chloro-N-ethyl-N-[2-hydroxy-2-(3-hydroxy-phenyl)-ethyl]-benzenesulfonamide | 356.0 | |
| 214 | 4-Chloro-N-(2-hydroxy-1-methyl-2-phenyl-ethyl)-N-methyl-benzenesulfonamide | | 362.0 |
| 215 | 4-Chloro-N-methyl-N-(1-methyl-piperidin-4-yl)-benzenesulfonamide | 303.1 | |
| 216 | 4-Chloro-N-ethyl-N-(2-pyridin-2-yl-ethyl)-benzenesulfonamide | 325.1 | |
| 217 | 4-Chloro-N-(2-cyano-ethyl)-N-cyclopropyl-benzenesulfonamide | 285.0 | |
| 218 | 4-Chloro-N-methyl-N-(2-pyridin-4-yl-ethyl)-benzenesulfonamide | 311.1 | |
| 219 | [(4-Chloro-benzenesulfonyl)-methyl-amino]-acetic acid ethyl ester | 292.0 | |
| 220 | 4-Chloro-N-(2-hydroxy-1-methyl-2-phenyl-ethyl)-N-methyl-benzenesulfonamide | | 362.0 |
| 221 | 4-Chloro-N-(2-hydroxy-1-methyl-2-phenyl-ethyl)-N-methyl-benzenesulfonamide | | 362.0 |
| 222 | 4-Chloro-N-cyanomethyl-N-methyl-benzenesulfonamide | | 266.9 |
| 223 | 4-Chloro-N-(2-cyano-ethyl)-N-ethyl-benzenesulfonamide | 273.0 | |
| 224 | 4-Chloro-N-[2-(3,4-dihydroxy-phenyl)-2-oxo-ethyl]-N-methyl-benzenesulfonamide | 356.0 | |
| 225 | N-(1-Benzyl-pyrrolidin-3-yl)-4-chloro-N-ethyl-benzenesulfonamide | 379.0 | |
| 226 | 4-Chloro-N-{3-methoxy-4-[2-(4-methyl-thiazol-5-yl)-ethoxy]-benzyl}-N-(1-phenyl-ethyl)-benzenesulfonamide | 557.9 | |
| 227 | 4-Chloro-N-{3-methoxy-4-[2-(4-methyl-thiazol-5-yl)-ethoxy]-benzyl}-N-(2-methyl-allyl)-benzenesulfonamide | 508 | |
| 228 | [2-(4-Chloro-benzenesulfonylimino)-imidazolidin-1-yl]-acetic acid | 318.0 | |

-continued

| EX. No. | Name | M + H+ | M + Na+ |
|---|---|---|---|
| 229 | 4-Chloro-N-pyrrolidin-3-yl-benzenesulfonamide | 261.0 | — |
| 230 | 4-Chloro-N-(2-chloro-3-phenyl-allyl)-N-(R-1-hydroxymethyl-3-methyl-butyl)-benzenesulfonamide | — | 464 |
| 231 | 4-Chloro-N-[3-(3-fluoro-phenyl)-allyl]-N-(R-1-hydroxymethyl-3-methyl-butyl)-benzenesulfonamide | — | 447.9 |
| 232 | 4-Chloro-N-(R-1-hydroxymethyl-3-methyl-butyl)-N-(3-phenyl-propyl)-benzenesulfonamide | 410.1 | — |
| 233 | 4-Chloro-N-(R-1-hydroxymethyl-3-methyl-butyl)-N-(3-phenyl-allyl)-benzenesulfonamide | — | 431 |
| 234 | 4-Chloro-N-(2,3-dihydro-benzo[1,4]dioxin-6-ylmethyl)-N-(R-1-hydroxymethyl-3-methyl-butyl)-benzenesulfonamide | — | 463 |
| 235 | N-Benzofuran-2-ylmethyl-4-chloro-N-(R-1-hydroxymethyl-3-methyl-butyl)-benzenesulfonamide | — | 444 |
| 236 | 4-[(4-Chloro-benzenesulfonyl)-(R-1-hydroxymethyl-3-methyl-butyl)-amino]-3-methyl-but-2-enoic acid ethyl ester | — | 440 |
| 237 | 4-Chloro-N-(R-1-hydroxymethyl-3-methyl-butyl)-N-(3-pyridin-3-yl-allyl)-benzenesulfonamide | 409 | — |
| 238 | 4-Chloro-N-cyclohexylmethyl-N-(R-1-hydroxymethyl-3-methyl-butyl)-benzenesulfonamide | 388 | — |
| 239 | 4-Chloro-N-[3-(2-fluoro-phenyl)-allyl]-N-(R-1-hydroxymethyl-3-methyl-butyl)-benzenesulfonamide | — | 447.9 |
| 240 | N-(2-Bromo-3-phenyl-allyl)-4-chloro-N-(R-1-hydroxymethyl-3-methyl-butyl)-benzenesulfonamide | — | 509.9 |
| 241 | N-Benzo[1,3]dioxol-5-ylmethyl-4-chloro-N-(R-1-hydroxymethyl-3-methyl-butyl)-benzenesulfonamide | — | 449 |
| 242 | 4-Chloro-N-(3-fluoro-4-methoxy-benzyl)-N-(R-1-hydroxymethyl-3-methyl-butyl)-benzenesulfonamide | — | 453 |
| 243 | 4-Chloro-N-[3-(3-chloro-phenyl)-allyl]-N-(R-1-hydroxymethyl-3-methyl-butyl)-benzenesulfonamide | — | 463.9 |
| 244 | 4-Chloro-N-(R-1-hydroxymethyl-3-methyl-butyl)-N-(2-methyl-3-phenyl-allyl)-benzenesulfonamide | — | 445 |
| 245 | 4-Chloro-N-(2,4-difluoro-benzyl)-N-(R-1-hydroxymethyl-3-methyl-butyl)-benzenesulfonamide | 418.1 | — |
| 246 | 4-Chloro-N-(R-1-hydroxymethyl-3-methyl-butyl)-N-(4-methoxy-benzyl)-benzenesulfonamide | — | 434.1 |
| 247 | 4-Chloro-N-(4-chloro-benzyl)-N-(R-1-hydroxymethyl-3-methyl-butyl)-benzenesulfonamide | 416 | — |
| 248 | N-(4-Bromo-benzyl)-4-chloro-N-(R-1-hydroxymethyl-3-methyl-butyl)-benzenesulfonamide | — | 483.1 |
| 249 | 4-Chloro-N-[3-(4-fluoro-phenyl)-allyl]-N-(R-1-hydroxymethyl-3-methyl-butyl)-benzenesulfonamide | — | 447.9 |
| 250 | 4-Chloro-N-(R-1-hydroxymethyl-3-methyl-butyl)-N-[3-(2-nitro-phenyl)-allyl]-benzenesulfonamide | 455 | — |
| 251 | 4-Chloro-N-(2-methyl-cyclohexyl)-N-(3-pyridin-3-yl-allyl)-benzenesulfonamide | 406 | — |
| 252 | N-(6-Bromo-pyridin-3-ylmethyl)-4-chloro-N-(2-methyl-cyclohexyl)-benzenesulfonamide | 459 | — |
| 253 | 4-Chloro-N-(R-1-hydroxymethyl-3-methyl-butyl)-N-(3-m-tolyl-allyl)-benzenesulfonamide | — | 444 |
| 254 | 4-Chloro-N-(R-1-hydroxymethyl-3-methyl-butyl)-N-(3-o-tolyl-allyl)-benzenesulfonamide | — | 444 |
| 255 | 4-Chloro-N-(R-1-hydroxymethyl-3-methyl-butyl)-N-[3-(2-methoxy-phenyl)-allyl]-benzenesulfonamide | — | 460.1 |
| 256 | 4-Chloro-N-(6-chloro-pyridin-3-ylmethyl)-N-(2-methyl-cyclohexyl)-benzenesulfonamide | 414 | — |

-continued

| EX. No. | Name | M + H+ | M + Na+ |
|---|---|---|---|
| 257 | 4-Chloro-N-(6-methoxy-pyridin-3-ylmethyl)-N-(2-methyl-cyclohexyl)-benzenesulfonamide | 410 | — |
| 258 | 4-Chloro-N-cyclopropylmethyl-N-(R-1-hydroxymethyl-3-methyl-butyl)-benzenesulfonamide | 346 | — |
| 259 | 4-Chloro-N-(R-1-hydroxymethyl-3-methyl-butyl)-N-propyl-benzenesulfonamide | 334 | — |
| 260 | 4-Chloro-N-furan-3-ylmethyl-N-(R-1-hydroxymethyl-3-methyl-butyl)-benzenesulfonamide | — | 393.9 |
| 261 | 4-Chloro-N-(R-1-hydroxymethyl-3-methyl-butyl)-N-pentyl-benzenesulfonamide | 362 | — |
| 262 | 4-Chloro-N-(R-1-hydroxymethyl-3-methyl-butyl)-N-naphthalen-2-ylmethyl-benzenesulfonamide | — | 454 |
| 263 | 4-Chloro-N-(R-1-hydroxymethyl-3-methyl-butyl)-N-(1-methyl-3-phenyl-propyl)-benzenesulfonamide | — | 446 |
| 264 | 4-Chloro-N-(2-ethyl-allyl)-N-(R-1-hydroxymethyl-3-methyl-butyl)-benzenesulfonamide | 360 | — |
| 265 | N-(4-Bromo-benzyl)-4-chloro-N-(2,5-dimethyl-cyclohexyl)-benzenesulfonamide | — | 494 |
| 266 | 4-Chloro-N-furan-2-ylmethyl-N-(R-1-hydroxymethyl-3-methyl-butyl)-benzenesulfonamide | — | 393.9 |
| 267 | N-Benzyl-4-chloro-N-(1S,2S-2-hydroxy-cyclohexyl)-benzenesulfonamide | — | 402 |
| 268 | 4-Chloro-N-(2-methyl-cyclohexyl)-N-(3-phenyl-allyl)-benzenesulfonamide | — | 426.1 |
| 269 | 4-Chloro-N-(3-furan-2-yl-2-methyl-allyl)-N-(R-1-hydroxymethyl-3-methyl-butyl)-benzenesulfonamide | 412 | — |
| 270 | 4-Chloro-N-(3,4-dimethoxy-benzyl)-N-(2,5-dimethyl-cyclohexyl)-benzenesulfonamide | — | 475 |
| 271 | 4-Chloro-N-(R-1-hydroxymethyl-3-methyl-butyl)-N-(3-p-tolyl-allyl)-benzenesulfonamide | — | 444 |
| 272 | 4-Chloro-N-(2,5-dimethyl-cyclohexyl)-N-(4-methoxy-benzyl)-benzenesulfonamide | — | 445 |
| 273 | 4-Chloro-N-[3-(4-chloro-phenyl)-allyl]-N-(R-1-hydroxymethyl-3-methyl-butyl)-benzenesulfonamide | — | 464 |
| 274 | 4-Chloro-N-(R-1-hydroxymethyl-3-methyl-butyl)-N-(3-phenyl-butyl)-benzenesulfonamide | 424.1 | — |
| 275 | 4-Chloro-N-(2,5-dimethyl-cyclohexyl)-N-(3-fluoro-4-methoxy-benzyl)-benzenesulfonamide | — | 463 |
| 276 | 4-Chloro-N-(3,4-dimethoxy-benzyl)-N-(1-hydroxymethyl-2-methyl-propyl)-benzenesulfonamide | — | 450 |
| 277 | 4-Chloro-N-(1-methyl-butyl)-N-(3-phenyl-allyl)-benzenesulfonamide | — | 400.1 |
| 278 | 4-Chloro-N-(1,3-dimethyl-butyl)-N-(3-phenyl-allyl)-benzenesulfonamide | — | 414.1 |
| 279 | 4-Chloro-N-(R-1-hydroxymethyl-3-methyl-butyl)-N-(2-methyl-pentyl)-benzenesulfonamide | 376 | — |
| 280 | 4-Chloro-N-(2,5-dimethyl-cyclohexyl)-N-(2-methyl-3-phenyl-allyl)-benzenesulfonamide | — | 455 |
| 281 | 4-[(4-Chloro-benzenesulfonyl)-(R-1-hydroxymethyl-3-methyl-butyl)-amino]-but-2-enoic acid ethyl ester | 404 | — |
| 282 | 4-Chloro-N-(R-1-hydroxymethyl-3-methyl-butyl)-N-(1-methyl-3-phenyl-allyl)-benzenesulfonamide | — | 444 |
| 283 | 4-Chloro-N-(1-chloro-3,4-dihydro-naphthalen-2-ylmethyl)-N-(R-1-hydroxymethyl-3-methyl-butyl)-benzenesulfonamide | — | 490 |
| 284 | 4-Chloro-N-(R-1-hydroxymethyl-3-methyl-butyl)-N-(2-methyl-4-phenyl-pentyl)-benzenesulfonamide | 452.1 | — |
| 285 | 4-Chloro-N-(2,4-difluoro-benzyl)-N-(2,5-dimethyl-cyclohexyl)-benzenesulfonamide | — | 451 |
| 287 | 4-Chloro-N-(2-methyl-cyclohexyl)-N-(3-phenyl-propyl)-benzenesulfonamide | — | 428.1 |
| 288 | 4-Chloro-N-(1-methyl-butyl)-N-(3-phenyl-propyl)-benzenesulfonamide | 380.1 | — |

| EX. No. | Name | M + H+ | M + Na+ |
|---|---|---|---|
| 289 | 4-Chloro-N-(1-ethyl-propyl)-N-(3-phenyl-allyl)-benzenesulfonamide | — | 400.1 |
| 290 | 4-Chloro-N-(2,5-dimethyl-cyclohexyl)-N-(3-phenyl-allyl)-benzenesulfonamide | — | 441 |
| 291 | 4-Chloro-N-[3-(4-dimethylamino-phenyl)-allyl]-N-(R-1-hydroxymethyl-3-methyl-butyl)-benzenesulfonamide | 451 | — |
| 292 | N-[3-(4-tert-Butyl-phenyl)-2-methyl-propyl]-4-chloro-N-(R-1-hydroxymethyl-3-methyl-butyl)-benzenesulfonamide | 480.2 | — |
| 293 | 4-Chloro-N-(1,3-dimethyl-butyl)-N-(3-phenyl-propyl)-benzenesulfonamide | 394.1 | — |
| 294 | 4-Chloro-N-(R-1-hydroxymethyl-3-methyl-butyl)-N-(3-methyl-but-2-enyl)-benzenesulfonamide | — | 382 |
| 295 | 4-Chloro-N-(R-1-hydroxymethyl-3-methyl-butyl)-N-(3-methyl-butyl)-benzenesulfonamide | 362 | — |
| 296 | 4-Chloro-N-(3,4-dimethoxy-benzyl)-N-(2,3-dimethyl-cyclohexyl)-benzenesulfonamide | — | 474.1 |
| 297 | 4-Chloro-N-(4,6-dichloro-2H-chromen-3-ylmethyl)-N-(R-1-hydroxymethyl-3-methyl-butyl)-benzenesulfonamide | — | 526.9 |
| 298 | 4-Chloro-N-(2,5-dimethyl-cyclohexyl)-N-(3-phenyl-propyl)-benzenesulfonamide | — | 443 |
| 299 | N-But-2-enyl-4-chloro-N-(R-1-hydroxymethyl-3-methyl-butyl)-benzenesulfonamide | 346 | — |
| 300 | 4-Chloro-N-(S-1,2-dimethyl-propyl)-N-(3-phenyl-allyl)-benzenesulfonamide | — | 400 |
| 301 | 4-Chloro-N-(R-1-hydroxymethyl-3-methyl-butyl)-N-methyl-benzenesulfonamide | 306.1 | — |
| 302 | 4-Chloro-N-cyclooctyl-N-(3,4-dimethoxy-benzyl)-benzenesulfonamide | — | 474.1 |
| 303 | 4-Chloro-N-(2-methoxy-1-methyl-ethyl)-N-(3-phenyl-allyl)-benzenesulfonamide | — | 402 |
| 304 | 4-Chloro-N-(2-methoxy-1-methyl-ethyl)-N-(3-phenyl-propyl)-benzenesulfonamide | 382.1 | — |
| 305 | 4-Chloro-N-(4-chloro-6-fluoro-2H-chromen-3-ylmethyl)-N-(R-1-hydroxymethyl-3-methyl-butyl)-benzenesulfonamide | — | 510.1 |
| 306 | 4-Chloro-N-(R-1-hydroxymethyl-3-methyl-butyl)-N-(1-methyl-1H-indol-2-ylmethyl)-benzenesulfonamide | 435 | — |
| 307 | 4-Chloro-N-(1-ethyl-propyl)-N-(3-phenyl-propyl)-benzenesulfonamide | 380.1 | — |
| 308 | 4-Chloro-N-(R-1-hydroxymethyl-3-methyl-butyl)-N-(1,2,3,4-tetrahydro-naphthalen-2-yl)-benzenesulfonamide | — | 444 |
| 309 | 4-Chloro-N-(R-1,2-dimethyl-propyl)-N-(3-phenyl-allyl)-benzenesulfonamide | — | 400.1 |
| 310 | 4-Chloro-N-(2-ethyl-butyl)-N-(R-1-hydroxymethyl-3-methyl-butyl)-benzenesulfonamide | 376 | — |
| 311 | 4-Chloro-N-(3,4-dimethoxy-benzyl)-N-(R-2-hydroxy-1-phenyl-ethyl)-benzenesulfonamide | — | 484 |
| 312 | R-N-sec-Butyl-4-chloro-N-(1-methyl-3-phenyl-propyl)-benzenesulfonamide | — | 402.1 |
| 313 | R-N-sec-Butyl-4-chloro-N-(3-phenyl-allyl)-benzenesulfonamide | — | 386 |
| 314 | R-N-Benzofuran-2-ylmethyl-N-sec-butyl-4-chloro-benzenesulfonamide | — | 400 |
| 315 | 4-Chloro-N-(3,4-dimethoxy-benzyl)-N-(4-methyl-cyclohexyl)-benzenesulfonamide | — | 460.1 |
| 316 | 4-Chloro-N-(1-hydroxymethyl-propyl)-N-(3-phenyl-propyl)-benzenesulfonamide | 382.1 | — |
| 317 | N-(2-Benzyl-cyclohexyl)-4-chloro-N-(R-1-hydroxymethyl-3-methyl-butyl)-benzenesulfonamide | — | 486.2 |
| 318 | 4-Chloro-N-(2-hydroxy-propyl)-N-(3-phenyl-propyl)-benzenesulfonamide | 368 | — |
| 319 | 4-Chloro-N-(1-hydroxymethyl-propyl)-N-(3-phenyl-allyl)-benzenesulfonamide | — | 402 |
| 320 | 4-Chloro-N-(R-1,2-dimethyl-propyl)-N-(3-phenyl-propyl)-benzenesulfonamide | 380.1 | — |
| 321 | R-N-sec-Butyl-4-chloro-N-[3-(2-methoxy-phenyl)-allyl]-benzenesulfonamide | — | 416.1 |

-continued

| EX. No. | Name | M + H+ | M + Na+ |
|---|---|---|---|
| 322 | 4-Chloro-N-(3-furan-2-yl-allyl)-N-(R-1-hydroxymethyl-3-methyl-butyl)-benzenesulfonamide | — | 419.9 |
| 323 | 4-Chloro-N-(3,4-dimethoxy-benzyl)-N-(3-hydroxy-2,2-dimethyl-propyl)-benzenesulfonamide | — | 450 |
| 324 | 4-Chloro-N-(2-hydroxy-propyl)-N-(3-phenyl-allyl)-benzenesulfonamide | — | 388 |
| 325 | R-N-sec-Butyl-4-chloro-N-(3-phenyl-propyl)-benzenesulfonamide | — | 388.1 |
| 326 | R-N-sec-Butyl-4-chloro-N-(1-methyl-1H-indol-2-ylmethyl)-benzenesulfonamide | 391.1 | — |
| 328 | R-N-sec-Butyl-4-chloro-N-(1-methyl-3-phenyl-allyl)-benzenesulfonamide | — | 400.1 |
| 329 | 2S,3R-2-[(4-Chloro-benzenesulfonyl)-(3-phenyl-propyl)-amino]-3-hydroxy-N-methyl-butyramide | 426.1 | — |
| 330 | 4-Chloro-N-(R-1-hydroxymethyl-3-methyl-butyl)-N-(2-pentyl-3-phenyl-allyl)-benzenesulfonamide | — | 500.1 |
| 331 | 4-Chloro-N-(3,4-dimethoxy-benzyl)-N-(1R,2S,5R-2-isopropyl-5-methyl-cyclohexyl)-benzenesulfonamide | — | 503 |
| 332 | R-N-sec-Butyl-4-chloro-N-(1-chloro-3,4-dihydro-naphthalen-2-ylmethyl)-benzenesulfonamide | — | 446.9 |
| 333 | 3-[(4-Chloro-benzenesulfonyl)-(3-phenyl-allyl)-amino]-piperidine-1-carboxylic acid tert-butyl ester | — | 513.1 |
| 334 | 4-[(4-Chloro-benzenesulfonyl)-(3-phenyl-allyl)-amino]-piperidine-1-carboxylic acid ethyl ester | — | 485.1 |
| 335 | 4-Chloro-N-(1S,2S-2-hydroxy-cyclopentyl)-N-(3-phenyl-propyl)-benzenesulfonamide | 394.1 | — |
| 336 | 4-[(4-Chloro-benzenesulfonyl)-(3-phenyl-propyl)-amino]-piperidine-1-carboxylic acid ethyl ester | 465.1 | — |
| 337 | 4-Chloro-N-(3,4-dimethoxy-benzyl)-N-(3-hydroxymethyl-bicyclo[2.2.1]hept-2-yl)-benzenesulfonamide | — | 490 |
| 338 | 4-Chloro-N-(S-1-hydroxymethyl-3-methyl-butyl)-benzenesulfonamide | 292 | — |
| 339 | 4-Chloro-N-(R-1-hydroxymethyl-3-methyl-butyl)-benzenesulfonamide | 292 | — |
| 340 | 4-Chloro-N-(3,4-dimethoxy-benzyl)-N-(R-1-hydroxymethyl-2-phenyl-ethyl)-benzenesulfonamide | — | 498 |
| 341 | 4-Chloro-N-(S-1-hydroxymethyl-3-methyl-butyl)-N-(3-phenyl-allyl)-benzenesulfonamide | — | 430 |
| 342 | 4-Chloro-N-(3,4-dimethoxy-benzyl)-N-[1-(4-methanesulfonyl-phenyl)-ethyl]-benzenesulfonamide | 524 | — |
| 343 | 3-[(4-Chloro-benzenesulfonyl)-(3,4-dimethoxy-benzyl)-amino]-piperidine-1-carboxylic acid tert-butyl ester | — | 547.2 |
| 344 | 4-Chloro-N-(3,4-dimethoxy-benzyl)-N-(1-phenyl-ethyl)-benzenesulfonamide | — | 468.1 |
| 345 | 4-Chloro-N-(R-1,2-dimethyl-propyl)-benzenesulfonamide | 262 | — |

Notch Signaling Assay for Selective Inhibitors of Gamma Secretase

A convergence of evidence indicates that the gamma secretase complex, comprised of the presenilin subunits, mediates the intra-membrane cleavage of Amyloid precursor protein (APP), and the Notch family of proteins (De Strooper, B., P. Saftig, K. Craessaerts, H. Vanderstichele, G. Guhde, W. Annaert, K. Von Figura and F. Van Leuven (1998). "Deficiency of presenilin-1 inhibits the normal cleavage of amyloid precursor protein." Nature 391(6665): 387-90; De Strooper, B., W. Annaert, P. Cupers, P. Saftig, K. Craessaerts, J. S. Mumm, E. H. Schroeter, V. Schrijvers, M. S. Wolfe, W. J. Ray et al. (1999). "A presenilin-1-dependent gamma-secretase-like protease mediates release of Notch intracellular domain." Nature 398(6727): 518-22; Mumm, J. S., E. H. Schroeter, M. T. Saxena, A. Griesemer, X. Tian, D. J. Pan, W. J. Ray and R. Kopan (2000). "A ligand-induced extracellular cleavage regulates gamma-secretase-like proteolytic activation of Notch1." Mol Cell 5(2): 197-206; Zhang, Z., P. Nadeau, W. Song, D. Donoviel, M. Yuan, A. Bernstein and B. A. Yankner (2000). "Presenilins are required for gamma-secretase cleavage of beta-APP and transmembrane cleavage of Notch-1." Nat Cell Biol 2(7): 463-5). Cleavage of APP by gamma secretase leads to β-amyloid synthesis. Cleavage of Notch1 by gamma secretase results in release of the Notch intracellular domain (NICD), which translocates to the nucleus and activates gene expression (Jarriault, S., C. Brou, F. Logeat, E. H. Schroeter, R. Kopan and A. Israel (1995). "Signalling downstream of activated mammalian Notch." *Nature* 377(6547): 355-8; Kopan, R., E. H. Schroeter, H. Weintraub and J. S. Nye (1996). "Signal transduction by activated Notch: importance of proteolytic processing and its regulation by the extracellular domain." *Proc Natl Acad Sci USA* 93(4): 1683-8; Schroeter, E. H., J. A. Kisslinger and R. Kopan (1998). "Notch-1 signalling requires ligand-induced proteolytic release of intracellular domain." *Nature* 393(6683): 382-6). In particular, Notch signaling activates transcription of the mammalian homolog of the *Drosophila* transcription factor hairy-enhancer of split (Hes). Transcriptional activation of Hes1 is mediated by de-repression of CBF1/RBPJk upon binding by NICD in the nucleus. These facts have been exploited to develop a reporter gene assay for Notch Signaling Hsieh, J. J., T. Henkel, P. Salmon, E. Robey, M. G. Peterson and S. D. Hayward (1996). "Truncated mammalian Notch1 activates CBF1/RBPJk-repressed genes by a mechanism resembling that of Epstein-Barr virus EBNA2." *Mol Cell Biol* 16(3): 952-9; Lu, F. M. and S. E. Lux (1996). "Constitutively active human Notch1 binds to the transcription factor CBF1 and stimulates transcription through a promoter containing a CBF1-responsive element." *Proc Natl Acad Sci USA* 93(11): 5663-7).

Gamma secretase inhibitors have been observed to block NICD formation, and inhibit Notch signaling (De Strooper, B., W. Annaert, P. Cupers, P. Saftig, K. Craessaerts, J. S. Mumm, E. H. Schroeter, V. Schrijvers, M. S. Wolfe, W. J. Ray et al. (1999). "A presenilin-1-dependent gamma-secretase-like protease mediates release of Notch intracellular domain." *Nature* 398(6727): 518-22). Due to the importance of Notch signaling in cell fate determination, and tissue differentiation during both development and in the adult, inhibition of Notch signaling by gamma secretase inhibitors is postulated to be a limiting factor in their therapeutic utility. In order to identify selective gamma secretase inhibitors, we have employed a reporter gene based Notch signaling assay using a constitutively active rat Notch1 construct (ZEDN1) provided by Dr Gerry Weinmaster, who is at the University of California at Los Angeles (UCLA) as described in Shawber, C., D. Nofziger, J. J. Hsieh, C. Lindsell, O. Bogler, D. Hayward and G. Weinmaster (1996). "Notch signaling inhibits muscle cell differentiation through a CBF1-independent pathway." *Development* 122(12): 3765-73 in combination with the CBF1 repressible Luciferase reporter gene 4xwtCBF1Luc (Hsieh, J. J., T. Henkel, P. Salmon, E. Robey, M. G. Peterson and S. D. Hayward (1996). "Truncated mammalian Notch1 activates CBF1/RBPJk-repressed genes by a mechanism resembling that of Epstein-Barr virus EBNA2." *Mol Cell Biol* 16(3): 952-9).

When 4xwtCBF1 Luciferase is co-transfected with NotchΔE (ZEDN1), γ-secretase cleavage of NotchΔE releases the Notch intracellular domain (NICD), which translocates to the nucleus and de-represses CBF1 mediated transcriptional repression, leading to transcription of the Luciferase reporter gene. Luciferase activity is easily assayed in cell extracts using commercially available kits. The activity of the reporter gene is directly correlated with gamma secretase cleavage of NotchΔE, and as such, a reduction in Luciferase activity provides a convenient measure of inhibition of gamma secretase cleavage of NotchΔE. A comparison of the IC50 values of compounds for inhibition of Notch signaling versus inhibition of β-amyloid production in 293sw cells is employed to guide in the selection of compounds that have the desired property of potent inhibition of β-amyloid synthesis with minimal inhibition of Notch Signaling.

Compounds 84, 91, 139, 147, 237, 244, and 252, exhibit IC50 values within the range of about 0.1 to 25 nM; compounds 2, 9, 22, 28, 80, 110, 149, 151, 256, and 262, exhibit IC50 values within the range of about 25 to 100 nM; an compounds 3, 5, 36, 49, 78, 115, 156, 264, 272, and 292, exhibit IC50 values within the range of about 100 to 1000 nM.

It will be apparent that the starting materials may be varied and additional steps employed to produce the varied compounds encompassed by the present invention. In some cases, protection of reactive functionalities may be necessary to achieve some of the above transformations. In general, such need for protecting groups, as well as the conditions necessary to attach and remove such groups, will be apparent to those skilled in the art of organic synthesis.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:
1. A compound of the formula:

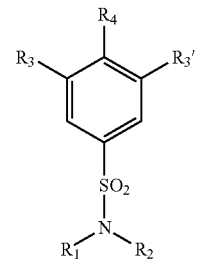

or a pharmaceutically acceptable salt thereof, wherein
$R_1$ is $C_1$-$C_8$ alkyl which is substituted with OH;
$R_2$ is $C_3$-$C_6$ alkenyl, substituted with 1 or 2 groups that are independently phenyl, halogen, 2H-chromenyl, 1,2,3,4-tetrahydronaphthalenyl, indolyl, 3,4-dihydronaphthalenyl, naphthyl, $C_3$-$C_8$ cycloalkyl, benzofuranyl, indolyl, 1,4-benzodioxanyl, 1,3-benzodioxolyl, pyridyl, halogen, —CO$_2$—($C_1$-$C_4$ alkyl), pyrazolyl, imidazolyl, oxazolyl, isoxazolyl, oxadiazolyl, thiazolyl, thiadiazolyl, triazolyl, or pyrimidyl;
wherein the cyclic portions of each of the above are optionally substituted with 1, 2, or 3 groups that are independently halogen, CO$_2$H, $C_1$-$C_4$ alkoxycarbonyl, —C(O)NH$_2$, —C(O)NH($C_1$-$C_4$) alkyl, —C(O)N ($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$R$_{25}$, —($C_1$-$C_4$ alkyl)S (O)$_x$—R$_{25}$, or OH; wherein
x is 0, 1, or 2;
$R_{25}$ is $C_1$-$C_6$ alkyl, OH, NR$_{26}$R$_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl;
$R_3$ is H, halogen, $C_1$-$C_6$ alkyl, $C_1$-$C_6$ alkoxy, CF$_3$, CN;

$R_4$ is halogen; and
$R_3$, is H, or halogen.

2. A compound according to claim 1 wherein
$R_2$ is $C_3$-$C_6$ alkenyl, which is substituted with 1 or 2 groups which are independently halogen, —$CO_2$—($C_1$-$C_4$ alkyl), pyrazolyl, imidazolyl, oxazolyl, isoxazolyl, oxadiazolyl, thiazolyl, thiadiazolyl, pyridyl, triazolyl, or pyrimidyl; wherein the cyclic portions of each of the above are optionally substituted with 1, or 2 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

3. A compound according to claim 1 wherein
$R_2$ is $C_3$-$C_6$ alkenyl, substituted with halogen or —$CO_2$—($C_1$-$C_3$ alkyl).

4. A compound according to claim 1 wherein
$R_2$ is $C_3$-$C_6$ alkenyl, substituted with 1 or 2 groups that are phenyl, halogen, pyrazolyl, imidazolyl, oxazolyl, isoxazolyl, oxadiazolyl, thiazolyl, thiadiazolyl, triazolyl, or pyrimidyl; wherein the phenyl group is optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy optionally substituted with pyridyl, thiazolyl, or methyl thiazol-5-yl, $C_1$-$C_4$ alkyl, —S(O)$_x$—$R_{25}$, —($C_1$-$C_4$ alkyl)-S(O)$_x$—$R_{25}$, or OH; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

5. A compound according to claim 4 wherein
$R_2$ is $C_3$-$C_6$ alkenyl substituted with phenyl; wherein the phenyl group is optionally substituted with 1, 2, or 3 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_4$ alkyl, or OH.

6. A compound according to claim 4 wherein
$R_2$ is $C_3$-$C_5$ alkenyl substituted with phenyl; wherein the phenyl group is optionally substituted with 1 or 2 groups that are independently halogen, $CO_2H$, $C_1$-$C_4$ alkoxycarbonyl, —C(O)$NH_2$, —C(O)NH($C_1$-$C_4$) alkyl, —C(O)N($C_1$-$C_4$)alkyl($C_1$-$C_4$) alkyl, $C_1$-$C_4$ alkoxy, or $C_1$-$C_4$ alkoxy substituted with pyridyl, thiazolyl, methyl thiazol-5-yl, —S(O)$_x$—$R_{25}$, or —($C_1$-$C_4$ alkyl)-S(O)$_x$—$R_{25}$; wherein
x is 0, 1, or 2;
$R_{25}$ is $C_1$-$C_6$ alkyl, OH, $NR_{26}R_{27}$;
$R_{26}$ and $R_{27}$ are independently H, $C_1$-$C_6$ alkyl, phenyl ($C_1$-$C_4$ alkyl), phenyl, or pyridyl; or
$R_{26}$, $R_{27}$ and the nitrogen to which they are attached represent pyrrolidinyl, piperidinyl, piperazinyl, morpholinyl, or imidazolidinyl.

7. A compound according to claim 6 wherein
$R_2$ is $C_3$-$C_5$ alkenyl substituted with phenyl, wherein the phenyl is substituted with 1 or 2 groups that are independently halogen, $CO_2H$, $C_1$-$C_4$ alkoxycarbonyl, or OH.

8. A compound according to claim 6 wherein
$R_2$ is $C_3$-$C_5$ alkenyl substituted with phenyl, wherein the phenyl is substituted with 1 or 2 groups that are independently halogen, —C(O)$NH_2$, —C(O)NH($C_1$-$C_4$) alkyl, —C(O)N($C_1$-$C_4$)alkyl($C_1$-$C_4$) alkyl, or OH.

9. A compound according to claim 4 wherein
$R_2$ is $C_3$-$C_5$ alkenyl substituted with phenyl; wherein the phenyl group is substituted with 1 methoxy group.

10. A compound according to claim 4 wherein
$R_2$ is $C_3$-$C_5$ alkenyl substituted with phenyl, which is unsubstituted.

11. A compound according to claim 4 wherein
$R_2$ is $C_3$-$C_5$ alkenyl substituted with phenyl, wherein the phenyl is substituted with 1 or 2 groups that are independently halogen, $CO_2H$, or $C_1$-$C_4$ alkoxycarbonyl.

12. A compound according to claim 1 that is
(S)-4-chloro-N-cinnamyl-N-(1-hydroxy-4-methylpentan-2yl)benzenesulfonamide;
4-Chloro-N-(1-hydroxymethyl-3-methyl-butyl)-N-(1-methyl-3-phenyl-allyl)-benzenesulfonamide;
4-Chloro-N-(1-hydroxymethyl-3-methyl-butyl)-N-(2-methyl-3-phenyl-allyl)-benzenesulfonamide;
4-Chloro-N-(1-hydroxymethyl-3-methyl-butyl)-N-[3-(2-methoxy-phenyl)-allyl]-benzenesulfonamide;
4-Chloro-N-(1-hydroxymethyl-propyl)-N-(3-phenyl-allyl)-benzenesulfonamide;
4-chloro-N-[(1S)-1-(hydroxymethyl)-3-methylbutyl]-N-[(2E)-2-methyl-3-phenylprop-2-en-1-yl]benzenesulfonamide;
4-chloro-N-[(1S)-1-(hydroxymethyl)-3-methylbutyl]-N-[(2E)-3-phenylprop-2-en-1-yl]benzenesulfonamide;
or a pharmaceutically acceptable salt thereof.

13. A compound according to claim 1 that is
4-Chloro-N—(R-1-hydroxymethyl-3-methyl-butyl)-N-(3-phenyl-allyl)-benzenesulfonamide;
4-Chloro-N—(R-1-hydroxymethyl-3-methyl-butyl)-N-(2-methyl-3-phenyl-allyl)-benzenesulfonamide;
4-Chloro-N-(2-hydroxy-propyl)-N-(3-phenyl-allyl)-benzenesulfonamide;
4-Chloro-N—(R-1-hydroxymethyl-3-methyl-butyl)-N-[3-(2-methoxy-phenyl)-allyl]-benzenesulfonamide;
4-Chloro-N—(R-1-hydroxymethyl-3-methyl-butyl)-N-(1-methyl-3-phenyl-allyl)-benzenesulfonamide;
4-[(4-Chloro-benzenesulfonyl)-(R-1-hydroxymethyl-3-methyl-butyl)-amino]-3-methyl-but-2-enoic acid ethyl ester;
4-Chloro-N—(S-1-hydroxymethyl-3-methyl-butyl)-N-(3-phenyl-allyl)-benzenesulfonamide;
N-(2-Bromo-3-phenyl-allyl)-4-chloro-N—(R-1-hydroxymethyl-3-methyl-butyl)-benzenesulfonamide;
4-Chloro-N—(R-1-hydroxymethyl-3-methyl-butyl)-N-(3-pyridin-3-yl-allyl)-benzenesulfonamide;
4-[(4-Chloro-benzenesulfonyl)-(R-1-hydroxymethyl-3-methyl-butyl)-amino]-but-2-enoic acid ethyl ester;
4-Chloro-N-(2-chloro-3-phenyl-allyl)-N—(R-1-hydroxymethyl-3-methyl-butyl)-benzenesulfonamide;
4-Chloro-N-[3-(3-chloro-phenyl)-allyl]-N—(R-1-hydroxymethyl-3-methyl-butyl)-benzenesulfonamide;
4-Chloro-N—(R-1-hydroxymethyl-3-methyl-butyl)-N-(3-p-tolyl-allyl)-benzenesulfonamide;
4-Chloro-N-[3-(4-fluoro-phenyl)-allyl]-N—(R-1-hydroxymethyl-3-methyl-butyl)-benzenesulfonamide;

4-Chloro-N—(R-1-hydroxymethyl-3-methyl-butyl)-N-(3-m-tolyl-allyl)-benzenesulfonamide;
4-Chloro-N-[3-(3-fluoro-phenyl)-allyl]-N—(R-1-hydroxymethyl-3-methyl-butyl)-benzenesulfonamide;
4-Chloro-N—(R-1-hydroxymethyl-3-methyl-butyl)-N-(3-o-tolyl-allyl)-benzenesulfonamide;
4-Chloro-N-[3-(4-chloro-phenyl)-allyl]-N—(R-1-hydroxymethyl-3-methyl-butyl)-benzenesulfonamide;
4-Chloro-N-[3-(2-fluoro-phenyl)-allyl]-N—(R-1-hydroxymethyl-3-methyl-butyl)-benzenesulfonamide;
4-[(4-Chloro-benzenesulfonyl)-(R-1-hydroxymethyl-3-methyl-butyl)-amino]-but-2-enoic acid ethyl ester;
or a pharmaceutically acceptable salt thereof.

14. A compound according to claim 1 wherein $R_1$ is

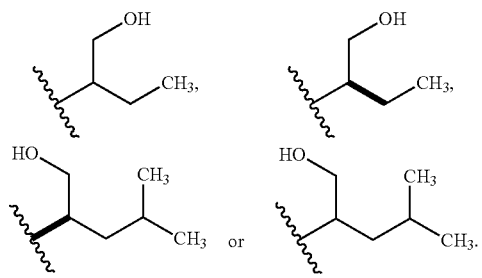

15. A pharmaceutical composition comprising a compound of claim 1 and at least one pharmaceutically acceptable carrier, solvent, adjuvant or excipient, or a combination thereof.

16. A compound of the formula:

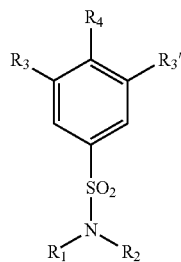

or a pharmaceutically acceptable salt thereof, wherein
$R_1$ is $C_1$-$C_8$ alkyl which is optionally substituted with OH;
$R_2$ is

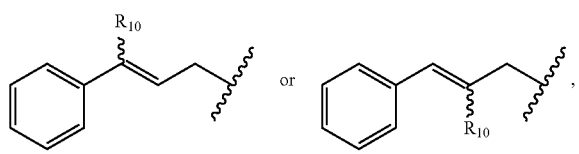

wherein
$R_{10}$ is $C_1$-$C_4$ alkyl, halogen, phenyl, pyridyl, pyrazolyl, imidazolyl, oxazolyl, isoxazolyl, oxadiazolyl, thiazolyl, thiadiazolyl; wherein the phenyl group is optionally substituted with 1, 2, or 3 groups that are independently halogen, $CO_2H$, $C_1$-$C_4$ alkoxycarbonyl, —C(O)NH$_2$, —C(O)NH($C_1$-$C_4$) alkyl, —C(O)N($C_1$-$C_4$)alkyl($C_1$-$C_4$) alkyl, $C_1$-$C_4$ alkoxy, $C_1$-$C_4$ alkyl, or OH;

$R_3$ is H, halogen, $C_1$-$C_6$ alkyl, $C_1$-$C_6$ alkoxy, $CF_3$, CN;
$R_4$ is halogen; and
$R_{3'}$ is H, or halogen.

17. A compound according to claim 16 wherein $R_1$ is $C_1$-$C_8$ hydroxyalkyl.

18. A compound according to claim 17 wherein $R_1$ is

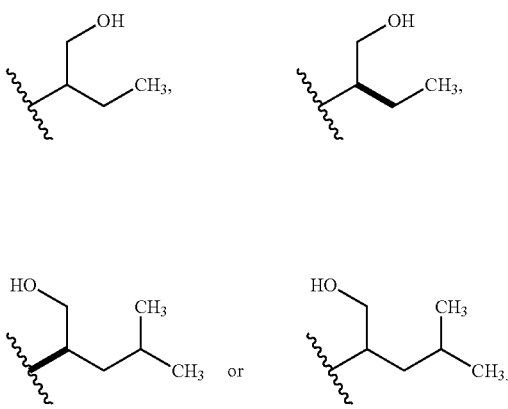

19. A compound according to claim 16 wherein $R_1$ is $C_1$-$C_8$ alkyl.

20. A compound according to claim 16 wherein
$R_3$ is H, halogen, $C_1$-$C_4$ alkyl, $C_1$-$C_4$ alkoxy, $CF_3$, CN; and
$R_{3'}$ is H, or halogen.

21. A compound according to claim 20 wherein
$R_3$ is H, halogen, methyl, methoxy, $CF_3$, or CN; and
$R_{3'}$ is H, or halogen.

22. A compound according to claim 21 wherein
$R_3$ is H, or halogen; and $R_{3'}$ is H, or halogen.

23. A compound according to claim 22 wherein
$R_3$ is H; $R_4$ is Cl; and $R_{3'}$ is H.

24. A compound which is
4-Chloro-N—(R-1-hydroxymethyl-3-methyl-butyl)-N-[3-(2-nitro-phenyl)-allyl]-benzenesulfonamide;
4-Chloro-N-(1-hydroxymethyl-3-methyl-butyl)-N-(2-pentyl-3-phenyl-allyl)-benzenesulfonamide;
4-Chloro-N—(R-1-hydroxymethyl-3-methyl-butyl)-N-(2-pentyl-3-phenyl-allyl)-benzenesulfonamide;
4-Chloro-N-(3-furan-2-yl-2-methyl-allyl)-N—(R-1-hydroxymethyl-3-methyl-butyl)-benzenesulfonamide;
4-Chloro-N-(3-furan-2-yl-allyl)-N—(R-1-hydroxymethyl-3-methyl-butyl)-benzenesulfonamide;
4-Chloro-N-[3-(4-dimethylamino-phenyl)-allyl]-N—(R-1-hydroxymethyl-3-methyl-butyl)-benzenesuflonamide;
4-Chloro-N-(1,2-dimethyl-propyl)-N-(3-phenyl-allyl)-benzenesulfonamide;
4-Chloro-N—(R-1,2-dimethyl-propyl)-N-(3-phenyl-allyl)-benzenesulfonamide;
4-Chloro-N—(S-1,2-dimethyl-propyl)-N-(3-phenyl-allyl)-benzenesulfonamide;
4-Chloro-N-(1,3-dimethyl-butyl)-N-(3-phenyl-allyl)-benzenesulfonamide;
4-Chloro-N-(1-ethyl-propyl)-N-(3-phenyl-allyl)-benzenesulfonamide;
4-Chloro-N-(1-methyl-butyl)-N-(3-phenyl-allyl)-benzenesulfonamide;

N-sec-Butyl-4-chloro-N-(1-methyl-3-phenyl-allyl)-benzenesulfonamide;
R—N-sec-Butyl-4-chloro-N-(1-methyl-3-phenyl-allyl)-benzenesulfonamide;
N-sec-Butyl-4-chloro-N-(3,3-diphenyl-allyl)-benzenesulfonamide;
N-sec-Butyl-4-chloro-N-(3-phenyl-allyl)-benzenesulfonamide;
R—N-sec-Butyl-4-chloro-N-(3-phenyl-allyl)-benzenesulfonamide;
N-sec-Butyl-4-chloro-N-[3-(2-methoxy-phenyl)-allyl]-benzenesulfonamide;
R—N-sec-Butyl-4-chloro-N-[3-(2-methoxy-phenyl)-allyl]-benzenesulfonamide;
4-Chloro-N-(2-methoxy-1-methyl-ethyl)-N-(3-phenyl-allyl)-benzenesulfonamide;
or pharmaceutically acceptable salts thereof.

* * * * *